(12) United States Patent
Duke et al.

(10) Patent No.: US 10,575,791 B2
(45) Date of Patent: Mar. 3, 2020

(54) AUTOMATIC RECOGNITION OF KNOWN PATTERNS IN PHYSIOLOGICAL MEASUREMENT DATA

(71) Applicant: Roche Diabetes Care, Inc., Indianapolis, IN (US)

(72) Inventors: David Duke, Fishers, IN (US); Abhishek S. Soni, Indianapolis, IN (US); Bernd Steiger, Roemerberg (DE); Jürgen Rasch-Menges, Schwetzingen (DE); Michael Brossart, Germersheim (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 218 days.

(21) Appl. No.: 13/923,357

(22) Filed: Jun. 20, 2013

(65) Prior Publication Data

US 2013/0338453 A1 Dec. 19, 2013
US 2019/0192084 A9 Jun. 27, 2019

Related U.S. Application Data

(63) Continuation of application No. PCT/EP2011/073084, filed on Dec. 16, 2011, now Pat. No. 8,774,889.
(Continued)

(30) Foreign Application Priority Data

Dec. 22, 2010 (EP) .................................... 10196379

(51) Int. Cl.
*G01N 33/48* (2006.01)
*A61B 5/00* (2006.01)
(Continued)

(52) U.S. Cl.
CPC ........ *A61B 5/7282* (2013.01); *A61B 5/14532* (2013.01); *A61B 5/486* (2013.01);
(Continued)

(58) Field of Classification Search
None
See application file for complete search history.

(56) References Cited

U.S. PATENT DOCUMENTS

| 6,360,888 B1 | 3/2002 | McIvor et al. |
| 9,247,901 B2 | 2/2016 | Kamath et al. |

(Continued)

FOREIGN PATENT DOCUMENTS

| EP | 1 918 837 A1 | 5/2008 |
| WO | WO 2006/066585 A2 | 6/2006 |
| WO | WO 2007/144419 A2 | 12/2007 |

OTHER PUBLICATIONS

Bentley, Jon, "Multidimensional Divide-and-Conquer", Comm. of the ACM, 23(4), Apr. 1980, 214-229.
(Continued)

*Primary Examiner* — Larry D Riggs, II
(74) *Attorney, Agent, or Firm* — Bose McKinney & Evans LLP

(57) ABSTRACT

A method for analyzing physiological measurement values of a user is proposed. The method comprises at least one data acquisition step, wherein, during the data acquisition step, physiological measurement values of the user are acquired at different measurement times and stored in a measurement data record; at least one pattern selection step, wherein, during the pattern selection step, measurement values acquired during one comparison time interval are selected as at least one comparison pattern; and at least one pattern recognition step, wherein, during the pattern recognition
(Continued)

step, patterns corresponding to the comparison pattern are sought after in the measurement data record.

18 Claims, 22 Drawing Sheets

Related U.S. Application Data

(60) Provisional application No. 12/975,654, filed on Dec. 22, 2010.

(51) Int. Cl.
*A61B 5/145* (2006.01)
*G16H 50/70* (2018.01)
*G06F 19/00* (2018.01)

(52) U.S. Cl.
CPC ............ *A61B 5/7246* (2013.01); *A61B 5/742* (2013.01); *G06F 19/00* (2013.01); *G16H 50/70* (2018.01)

(56) References Cited

U.S. PATENT DOCUMENTS

| | | |
|---|---|---|
| 2003/0125612 A1 | 7/2003 | Fox et al. |
| 2004/0122708 A1 | 6/2004 | Avinash et al. |
| 2007/0294360 A1 | 12/2007 | Ebling et al. |
| 2008/0242962 A1 | 10/2008 | Roesicke et al. |
| 2010/0160740 A1 | 6/2010 | Cohen et al. |

OTHER PUBLICATIONS

Bentley, Jon, "Multidimensional Binary Search Trees Used for Associative Searching", Comm. of the ACM, 18(9), 1975, 509-517.

International Search Report issued by the European Patent Office, Rijswijk, NL, dated Jan. 25, 2012, for International Application No. PCT/EP2011/073084; 6 pages.

AUTOMATIC RECOGNITION OF KNOWN PATTERNS IN PHYSIOLOGICAL MEASUREMENT DATA

RELATED APPLICATIONS

The present application is a continuation of and claims priority to co-pending International Application No. PCT/EP2011/073084, filed Dec. 16, 2011, which claims priority to European Application No. EP 10 196 379.1, filed Dec. 22, 2010, and U.S. application Ser. No. 12/975,654, filed Dec. 22, 2010, the entire disclosures of which being expressly incorporated herein by reference.

FIELD OF THE DISCLOSURE

The invention relates to a method and a device for analysing physiological measurement values of a user. Furthermore, the invention relates to a computer program with program code for carrying out a method according to the invention. Such devices, methods and computer programs can be used in general for acquiring and analysing physiological measurement data of a user, for example in long-term monitoring of human or animal users within the scope of so-called home monitoring or else during hospital stays. The method, the device and the computer program can be used in particular for automatically identifying patterns in a chronological sequence of physiological measurement values. In particular, the method, the device and the computer program can be used for automatically carrying out a retrospective consideration of current patterns in physiological measurement data, e.g. in glucose values or other types of analyte concentrations, by comparison with historical data. In particular, a historical situation of the user can be found in this case, which corresponds best to the current situation of the user in order, accordingly, to take suitable measures.

Further, the following disclosure relates generally to patient monitoring, and in particular to a continuous glucose monitoring system with an efficient pattern matching algorithm, a method, and a computer product thereof.

BACKGROUND OF THE DISCLOSURE

In general, diabetes can be characterized by hyperglycemia and relative insulin deficiency. There are two main types of diabetes, Type I diabetes (insulin-dependent diabetes mellitus) and Type II diabetes (non-insulin-dependent diabetes mellitus). In some instances, diabetes is also characterized by insulin resistance.

Insulin secretion functions to control the level of blood glucose to keep the glucose levels at an optimum level. Healthcare may involve both establishing a therapeutic program and monitoring the progress of the afflicted person. Monitoring blood glucose levels is an important process that is used to help diabetics maintain blood glucose levels as near as normal as possible throughout the day. Monitoring can also allow successful treatment of a diabetic by altering therapy as necessary. Monitoring may allow the diabetic to monitor more closely his or her condition and, in addition, can provide information of value to the healthcare provider in determining both progress of the patient and detecting any need to change the patient's therapy program.

Advances in the field of electronics over the past several years have brought about significant changes in medical diagnostic and monitoring equipment, including self-care monitoring. In controlling and monitoring diabetes, relatively inexpensive and easy-to-use blood glucose monitoring systems have become available that provide reliable information that allows a diabetic and his or her healthcare professional to establish, monitor and adjust a treatment plan.

There are two main types of blood glucose monitoring systems used by patients: single point (or non-continuous) systems and continuous systems. Non-continuous systems consist of meters and tests strips and require blood samples to be drawn from fingertips or alternate sites, such as forearms and legs. An example of a non-continuous system may require a diabetic to apply a blood sample to reagent-impregnated region of a test strip, wipe the blood sample from the test strip after a predetermined period of time, and, after a second predetermined period of time, determine blood glucose level by comparing the color of the reagent-impregnated regions of the test strip with a color chart supplied by the test strip manufacturer. These systems also can rely on lancing and manipulation of the fingers or alternate blood draw sites, which can be extremely painful and inconvenient, particularly for children.

An example of a continuous system is a continuous glucose monitor ("CGM") that can be implanted subcutaneously and measure glucose levels in the interstitial fluid at various periods throughout the day, providing data that shows trends in glucose measurements over a period of time. CGMs can provide large quantities of data that need to be processed to find patterns of similar data. The data can be used to identify harmful patient behaviors or to help optimize therapy based on similar past experiences. It can also be used to monitor glucose over time to determine a blood sugar pattern. Because of the large quantities of data involved, an efficient algorithm may be needed to enable pattern matching on devices with limited processing power.

In addition to the so-called point measurements, which are only carried out once or a couple of times, the prior art has, inter alia, also disclosed long-term monitoring of one or more physiological parameters. In the following text, the invention will substantially be described with reference to physiological parameters in the form of analyte concentrations of one or more analytes in a bodily fluid of the user, e.g. a human or animal patient, independently of whether a disease is actually present or whether there should merely be monitoring of healthy users. Without restricting further possible applications, the invention will be described in the following text with reference to blood-glucose monitoring. However, in principle, the invention is also transferable to other types of analytes and/or monitoring other types of physiological parameters.

In recent times, a so-called continuous glucose measurement, which is also referred to as continuous monitoring (CM), in the interstitium of the user is becoming ever more established. This method is suitable for managing, monitoring and controlling e.g. a diabetes status. By now, the prior art has in this case disclosed directly implanted electrochemical sensors, which are often also referred to as needle-type sensors (NTS). Here, the active sensor region is brought directly to a measurement location, which is generally arranged in the interstitial tissue and converts glucose into electric charge, for example by using an enzyme (e.g. glucose oxidase, GOD), which charge is proportional to the glucose concentration and can be used as a measurement variable. Examples of such transcutaneous measurement systems are described in U.S. Pat. No. 6,360,888 B1 or in US 2008/0242962 A1. Continuous monitoring systems generally acquire measurement values, e.g. glucose measurement values, at regular or irregular time intervals. By way of example, glucose measurement values can be acquired at intervals of 5 min or less in the case of implanted sensors.

In contrast to so-called point measurements, which merely acquire an instantaneous body state of the user, measurement data records of a long-term measurement of physiological parameters, such as e.g. a long-term measurement of an analyte concentration in the body tissue, thus comprise a multiplicity of further items of information, which, in principle, are available for evaluation. In particular, it is possible to follow developments over time, follow the influences of external effects on the body of the user and maybe even propose likely future profiles of the measurement values and derive recommendations for the user from this. However, a technical challenge consists of the fact that the measurement data record reaches a technical time resolution that is confronted with a huge data volume and hence requires novel methods of data preparation, data aggregation and data reuse. Otherwise, the increase in the data volume can even lead to a reduction in the user-friendliness of the methods and devices for the user, and to a lacking overview for the treating medical practitioner.

EP 1 918 837 A1 has disclosed a method for processing a chronological sequence of measurement values of a time-dependent parameter. A method is described of how a patient can himself select relevant portions from a time profile of measurement values of the glucose concentration, which portions represent the isolated influence of individual events and make said profile transparent, comprehensible and predicable. The knowledge in respect of the metabolic state overall can be improved on the basis of a collection of such portions. To this end, the profile of a glucose concentration over time after an isolated event, e.g. a specific meal, is stored for later comparisons, for example under a reference corresponding to this meal. The patient can create a personal archive of such event-specific CM profiles for himself and use it for comparisons in respect of a current situation. This option of comparing is valuable to patients and treating medical practitioners for increasing the depth of knowledge in respect of personalized effects of meals, sport, travel, stress or hormonal states. Here, it is proposed to generate a portion from a curve profile by fixing a start time and an end time. This portion is assigned to a specific event, e.g. a specific meal, and is optionally stored under a specific reference that characterizes the event. If the patient is once again in a comparable situation, he can search his archive for corresponding previous events. Such a search is generally oriented towards the names, which were given by the patient himself. Possible finds can be compared to the current profile, and the patient can thus prepare for the current situation.

WO 2006/066585 A2 has also disclosed methods and devices for pattern recognition in physiological measurement data. Here, patterns are identified in a measurement data record, which patterns correspond to at least one physiological state of the user. Measurement values are stored in conjunction with user actions and allow a targeted search for patterns in the measurement data record in conjunction with thresholds for the user action.

Thus, the known methods in principle are very time-consuming and are possibly too complicated for potential users, in particular for children, elderly patients or patients with dementia. For example, the assignment of names to particular events, such as naming a specific meal, or a qualification and quantification of certain user events by the user himself is subject to very subjective criteria, and so, possibly, finding a corresponding pattern may not be possible or may even be misleading as a result of initial naming or storing that was not thought through by inexperienced or overburdened patients. A manual method is not efficient, particularly for large data stocks, as are already expected for a measurement period spanning a couple of days. Moreover, many methods presuppose smoothing of the generally noisy measurement value profiles. Furthermore, there are technical challenges in quantifying the similarity of portions. Moreover, manual methods in principle are time-consuming and generally inefficient. Furthermore, there has not yet been a satisfactory solution to technical challenges that occur in the processing of found patterns, particularly if a number of possible patterns have been identified.

Accordingly, it is an object of the present invention to specify a method, a computer program and a device that at least largely avoid the disadvantages of known methods, computer programs and devices. In particular, a method should be specified for analysing physiological measurement values, which can easily be carried out online and in an automatic fashion, preferably in real-time, and which is able to find historical situations of the user that are as similar as possible to the current situation of the user in order to provide him with the option of reacting in an ideal fashion to the current situation. It should preferably be possible to establish a probable future profile of the physiological measurement values, and it should preferably be possible to specify boundary conditions that had a positive effect in similar situations in the past and which could also constitute expedient measures in a current situation.

SUMMARY OF THE DISCLOSURE

In a first aspect of the present invention, a method is proposed for analysing physiological measurement values of a user. Physiological measurement values and physiological data are equivalent terms for the same subject-matter. A user can, in general terms, be a patient or can be one or more persons and/or animals, independently of whether or not a disease state is present. The user or, in the case of a group of users, at least one of the users can carry out the method himself, or the method can be carried out by at least one third person, e.g. a medical practitioner or care staff. In the following text, no distinction is made between both options, which should be comprised by the invention, and so, for example, the case should also be comprised, in which the physiological measurement values originate from at least one first user, while one or more method steps of the method are carried out by at least one second user, e.g. a medical practitioner or care staff.

The term "analysis" can be taken very broadly in this case and can, in principle, comprise any treatment, acquisition, storage, pre-processing, processing or transferring of the measurement values. Physiological measurement values are, in general, understood to mean any parameters that directly characterize one or more body states of a user. The physiological measurement values can directly be measurement values, which are acquired by at least one measurement device, or, this should have the same meaning within the scope of the present invention, measurement values derived from these measurement values, for example measurement values that have already been subjected to pre-processing, filtering, amplification, smoothing or similar pre-processing steps. Measurement device and physiological input device are equivalent terms for the same subject-matter. In particular, as will be explained in more detail below, the physiological measurement values can be concentrations of at least one analyte in a bodily fluid of a user. However, in principle, the use of other types of physiological measurement values is also feasible as an alternative or in addition thereto. In particular, the method can, in general, be used to identify a presence of a physiological body state of the user.

The method comprises the method steps illustrated below. The method steps can be carried out in the illustrated sequence. However, in principle, a different sequence to the illustrated sequence is also possible. Thus, in particular, individual or multiple method steps can be carried out parallel in time, overlapping in time or repeatedly, either on their own or in groups. Furthermore, the method can comprise additional method steps that are not illustrated in the following text. Independently of the fact that the term method step is used in the following text, the reference "step" basically says nothing about the duration of the method steps listed in the following text. Thus, the specified method steps can, individually or in groups, be carried out briefly, but can also be carried out over a longer time period, for example over time intervals of a number of minutes, hours, days, weeks or even months, for example continuously or repeatedly.

In one embodiment, the present method comprises at least one data acquisition step, wherein, during the data acquisition step, physiological measurement values of the user are acquired at different measurement times and stored in a measurement data record. As illustrated above, the physiological measurement values can, in particular, be any parameters that in some way characterize the body state of the user. In particular, these may be parameters that characterize at least one concentration of at least one analyte, for example at least one concentration of at least one analyte in a bodily fluid, for example at least one metabolite, more particularly glucose. In general, the physiological measurement values can be primary measurement values, for example directly after acquisition, or else they can be measurement values which are derived from these measurement values and, for example, have already been pre-processed. By way of example, the measurement times can be fixedly prescribed or else be variable. The measurement times can follow one another continuously such that a measurement-time continuum is created, but can, in principle, also be discontinuous. The measurement times can be arranged equidistantly from one another or measurement times can be selected at irregular intervals. Data acquisition steps in which physiological measurement values are acquired at regular time intervals, for example at time intervals of 5 min, are particularly preferred. By way of example, the measurement times can be prescribed in absolute terms, but they can also be prescribed in a relative way, for example by defining a time interval from a particular event, for example one or more preceding measurement times. The measurement times preferably correspond to a time window data set as given further below. In an embodiment, the measurement values are input by a user as a query. The physiological measurement values and physiological data acquired within intervals of the measurement times can be denoted as time window data set. Preferably, the time interval, measurement-time continuum or time points corresponds to the term "time window" as used herein.

Within the scope of the present invention, a measurement data record should be understood to mean a data record that at least comprises the measurement values but which can preferably also comprise one or more additional parameters. By way of example, these further parameters can comprise the measurement times; however, this is not mandatory because measurement times, for example, can also be established by another way. By way of example, data pairs can be stored in the measurement data record, which data pairs each comprise at least one measurement value and at least one associated measurement time, specified as an absolute measurement time or else as a relative measurement time, for example specified as a time from a specific event. Moreover, the measurement data record may, as will be explained in more detail below, comprise further parameters such as e.g. one or more boundary conditions. Alternatively, or in addition thereto, the measurement data record can also comprise the physiological measurement values in a chronological sequence, without needing to store the measurement times for this, for example if the measurement times can easily be calculated for each measurement value, particularly if fixed time intervals are prescribed between the measurement times. The data acquisition step can be carried out continuously or discontinuously over, in particular, a relatively long period of time, for example within the scope of continuous monitoring, for example, as will be explained in more detail below, by means of at least one sensor that, continuously or discontinuously, supplies physiological measurement values over a relatively long period of time, for example at regular or else irregular time intervals.

In one embodiment the present method further comprises at least one pattern selection step, wherein, during the pattern selection step, measurement values acquired during at least one comparison time interval are selected as at least one comparison pattern. Within the scope of the present invention, a comparison time interval is understood to mean a time interval that is, or could be, of interest for the analysis of the physiological measurement values. In this respect, this comparison time interval can for example be a so-called "region of interest" on a time axis. Like other time intervals or intervals within the scope of the present invention, the comparison time interval can also for example be specified as a closed interval, an open interval or as an interval closed on one side. Time interval and time window are equivalent terms for the same subject-matter. Further, the comparison time interval preferably corresponds to the reference pattern.

Within the scope of the present invention, a pattern is, in general, understood to be a sequence of measurement values. Accordingly, a comparison pattern should be understood to be the sequence of measurement values that were acquired during the comparison time interval. The comparison time interval can, as will be explained in more detail below, in particular be or comprise a current time interval. In this case, the comparison pattern, can in particular, be or comprise a current pattern.

Alternatively, or in addition thereto, the comparison time interval can also be or comprise a selectable time interval, for example a time interval that can be selected by the user. If the comparison time interval is a selectable time interval or if the former comprises a selectable time interval, the comparison pattern can, in particular, be or comprise a pattern of interest. In general, "of interest" or "interesting" is, in the following text, understood to mean a property, in which a specific element is assigned a possible meaning, either subjectively or according to prescribed criteria, which meaning may still have to be verified. By way of example, a pattern of interest can be a pattern that has specific characteristics that may be relevant according to physiological aspects or medical aspects, or a pattern that is temporally linked to one or more boundary conditions. In particular, pattern of interest and reference pattern are equivalent terms for the same subject-matter. Further, the reference pattern or the pattern of interest can be inputted as a query via a user interface as given further below.

In principle, in the case of a selectable time interval, the comparison time interval can be selected in various ways.

By way of example, the selection can be brought about by entering boundaries of the selectable time interval, for example a lower boundary and an upper boundary. Alternatively, or in addition thereto, the selection can also be effected in a different fashion, for example by a graphical selection, for example by the user selecting a time interval on a display element, for example by means of an appropriate input device and/or selection device, for example one or more keys and/or a mouse and/or a cursor and/or a touchscreen. The time interval can be selected directly, for example by the user making a selection on a time axis, or indirectly, for example by the user selecting the comparison pattern, for example by marking on a screen or in another way, and by the comparison time interval belonging to this comparison pattern being selected accordingly. Other types of selection are also feasible.

In general terms, the term "current" is used within the scope of the present invention for a time, for example a measurement time, that in terms of time is situated so close to the now-time, i.e. the actual time at which the relevant method step is carried out and/or at which a measurement is carried out, that the time interval is negligible within the scope of conventional time intervals that take place on macroscopically perceivable physiological changes in the body of the user. In particular, these can be time intervals that are preferably no longer than 1 h, more particularly no longer than 30 min and particularly preferably no longer than 10 min or even no longer than 5 min. Accordingly, a current time, for example a current measurement time, need not necessarily correspond to the now-time, but can in principle also lie in the past by an amount of time that preferably does not exceed the aforementioned times. If the term "current" is used in conjunction with a number of continuous times, e.g. time intervals, this is understood to be a time interval that comprises at least one time that should be characterized as "current" within the scope of the aforementioned definition. The terms current and real-time are equivalent terms for the same subject-matter.

By way of example, in order to carry out the pattern selection step, the comparison time interval, e.g. the current time interval or the selectable time interval, can be prescribed and/or be selectable by the user. By way of example, the comparison time interval can be a time interval with a prescribed duration or a selectable duration, which is for example arranged in a prescribed fashion to a reference time, e.g. to a current time. By way of example, the time interval can be defined or prescribed by one or two time intervals from interval boundaries in one or two directions from the reference time, e.g. the current time. The comparison time interval, more particularly the current time interval, can for example be a time interval that extends from the now-time into the past by a prescribed amount, e.g. at least 1 h, preferably 1 h to 10 h and particularly preferably 4 h to 8 h. Other definitions or prescriptions of the comparison time interval, which can be prescribed in a fixed or adjustable fashion, are also feasible.

The comparison pattern, for example the current pattern and/or the pattern of interest thus comprises the measurement values acquired during the comparison time interval, for example during the current time interval and/or during the selectable time interval, or at least part of these measurement values, for example selected measurement values during this comparison time interval. Furthermore, the comparison pattern can contain additional information, for example once again, as explained above in conjunction with the measurement data record, the associated measurement times of the measurement values acquired during the comparison time interval, for example once again as measurement value pairs, comprising the measurement value and the respectively associated measurement time. Merely storing the measurement values, without the associated measurement times thereof, is also feasible, for example if the associated measurement times are known or derivable in a simple fashion, for example by having equidistant measurement times. Moreover, the comparison pattern can once again comprise further information, for example once again, as will be explained in more detail below, one or more boundary conditions. Thus, in particular, the comparison pattern can comprise a time-contiguous portion, in particular a current portion and/or a portion of interest, of the measurement data record, for example the most recent entries of the measurement data record, which extend into the past from the now-time by a prescribed amount. Other embodiments are also possible.

In one embodiment, the present method further comprises at least one pattern recognition step, wherein, during the pattern recognition step, patterns corresponding to the comparison pattern are sought after in the measurement data record. In principle, one or more pattern recognition methods can be used in the pattern recognition step, for example pattern recognition methods known from the prior art. In particular, it is possible to use methods that carry out a point-by-point comparison between the comparison pattern, e.g. the current pattern and/or the pattern of interest, and historical data in the measurement data record. Here, a point-by-point comparison is understood to mean a comparison in which respectively one measurement value in the comparison pattern is compared to one measurement value in the measurement data record, the latter being recorded e.g. at a different measurement time, more particularly at an earlier measurement time. The pattern recognition step can be carried out such that corresponding patterns are merely sought after outside of the comparison time interval. However, alternatively the comparison time interval itself can also be included in the search because, for example, repeating patterns can also occur within the comparison time interval. However, measurement values acquired at different measurement times should be compared to one another during the pattern recognition step in any case. Pattern recognition and pattern matching are equivalent terms for the same subject-matter.

It is preferably also possible to quantify deviations during the pattern recognition step, particularly during the comparison of the measurement values, and, as will still be explained in more detail below, it is possible to prescribe tolerances and/or undertake weightings.

By way of example, a point-by-point comparison can be carried out by virtue of the fact that at least one candidate point, more particularly at least one candidate time and/or candidate value, is identified in the measurement data record, starting from which candidate point the point-by-point comparison is carried out. In general, a "candidate" is understood to mean an element in a set, which element comes into consideration for a comparison and which can or must be subjected to a closer examination. By way of example, a candidate pattern can be understood to mean a pattern in the measurement data record which may correspond to the comparison pattern, although this should or must be examined more closely. Accordingly, a candidate time interval can be understood to mean a time interval during which the measurement values of the candidate pattern were acquired. A candidate time can be understood to mean a possible time that comes into consideration as a reference point for localizing the candidate time interval— however, this should or must be examined more closely—for example a measurement time at which a candidate value is acquired, which candidate value may correspond to an anchor value, which was acquired at an anchor time, which in turn serves as a reference time for localizing the comparison time interval.

By way of example, it is possible to carry out a step-by-step measurement value comparison, starting from a candidate value, wherein, for example, there may also be a termination of a continued comparison if a preceding value comparison did not lead to a correspondence. By way of example, comparisons can be carried out at equidistant time steps. However, in principle, non-equidistant steps are also possible.

By way of example, a pattern recognition step and a search for corresponding patterns can be brought about by virtue of the fact that, starting from a candidate value and/or candidate time, there is, step-by-step, a comparison between further measurement values and measurement values in the comparison pattern, for example by virtue of the fact that there is a query after every comparison step as to whether or not the preceding comparison yielded correspondence. If no correspondence was determined, a further comparison can be terminated in order to accelerate the method. If a correspondence was determined, it is possible to carry out a further comparison step with a next measurement value. This will, in an exemplary fashion, still be explained in more detail below.

Thus, within the scope of the present invention, correspondence should be understood to mean identical patterns or correspondence within the scope of one or more prescribed tolerance thresholds. Here, one or more tolerance thresholds can for example be prescribed in respect of the measurement values. Alternatively, or in addition thereto, tolerance thresholds can also be prescribed in respect of the measurement times, particularly if non-equidistant measurement times are selected. By way of example, in respect of the measurement points, tolerance neighbourhoods can thus be plotted around the measurement points, which are respectively plotted in a coordinate system with a measurement time axis and a measurement value axis, for example circular tolerance neighbourhoods and/or elliptic tolerance neighborhoods.

By way of example, a correspondence can be quantified point-by-point or for the entire pattern, for example, as will still be explained in more detail below, by one or more correlations, for which, in turn, thresholds may be provided. However, it is particularly preferred if, as described above, there is a point-by-point comparison taking into account one or more predetermined tolerance thresholds.

The proposed method can be advantageously developed in various ways. Thus, as described above, it is particularly preferred if the physiological measurement values comprise concentrations of at least one analyte in a bodily fluid of the user or are at least derived from measurement values that quantify such concentrations. In principle, the at least one analyte can be at least one arbitrary analyte, which is preferably detected specifically. In particular, this can be glucose, for example blood glucose. However, alternatively or additionally, other analytes are also detectable, for example cholesterol, lactate or other analytes. However, in another alternative to detecting an analyte, or in addition thereto, it is also possible to use other physiological measurement values.

In particular, the physiological measurement values can be acquired by means of at least one long-term measurement method, i.e. a measurement method in which measurement values are acquired at regular or irregular intervals over a time period of preferably at least 1 min, in particular at least 10 min, preferably at least 1 h, particularly preferably at least 10 h, at least 1 day, at least 1 week, or even over a plurality of months or years. In particular, the long-term measurement method can be carried out by means of at least one sensor element, e.g. an electrochemical sensor element for analyte detection, which was inserted into body tissue of the user. By way of example, reference can be made to the aforementioned prior art in this respect. Thus, for example, the method can be carried out using at least one continuous monitoring sensor, for example a sensor that comprises a patch, which is applied to the skin surface of the user and has actuation and evaluation electronics, and an insertable sensor connected to this patch. However, in principle, other types of measurement value acquisition are also possible.

In a further advantageous embodiment, the comparison time interval can, as already explained above, in particular be or comprise a current time interval, wherein the comparison pattern comprises a current pattern. In the pattern recognition step, it is possible to search for patterns that correspond to the current pattern, for example in the measurement data record prior to the current time interval, in which, however, as explained above, the current time interval can itself in principle also be included in the search.

Alternatively, or in addition thereto, the comparison time interval can comprise a selectable time interval, for example a time interval that is selectable by a user according to one or more of the above-described options and can also be referred to as "region of interest". In particular, the comparison pattern can then comprise a pattern of interest. The selectable time interval can be situated completely before e.g. the optionally fixable current time and/or before the optionally fixable current time interval; however, in principle it may also overlap therewith. Alternatively, it is also possible to dispense with fixing a current time and/or a current time interval if a selectable time interval is used. The selectable time interval can, in particular, be arranged in the past and can for example be selected in a subsequent analysis of the measurement data record, in particular historical measurement data, for example by the user, for example using a data processing instrument such as e.g. a computer. This fixing can for example also be brought about by a medical practitioner as a user. Various other options are feasible.

In a further advantageous embodiment of the method, at least one data reduction step is carried out for generating at least one reduced measurement data record from the measurement data record. This at least one data reduction step can be carried out for the entire measurement data record, preferably the raw data or the raw data vector as mentioned further below, or else for merely part thereof, for example for the current pattern. In particular, the reduced measurement data record can be used in at least one of the pattern selection step and/or the pattern recognition step, preferably in both steps. In the process, in the pattern selection step and the pattern recognition step, use can be made of the same at least one reduced measurement data record or else use can be made of different reduced measurement data records. Furthermore, in the pattern selection step and/or the pattern recognition step, use can optionally be made in each case of a plurality of different reduced measurement data records, for example, in the pattern selection step, at least a first reduced measurement data record and at least a second reduced measurement data record that differs from the first and/or, in the pattern recognition step, at least a third reduced measurement data record and at least a fourth reduced measurement data record that differs from the third measurement data record. Various combinations are possible. Hence, the at least one reduced measurement data record can comprise a single reduced measurement data record; however, it may also comprise a plurality of reduced measurement data records. Thus, for example, as illustrated above, use can be made of a plurality of different reduced measurement data records in the pattern selection step and/or the pattern recognition step. Preferably the data reduction step corresponds to the data compression mentioned further below and vice versa. Reduced data record and compressed data are equivalent terms for the same subject-matter.

In particular, it is possible to generate at least one reduced comparison pattern, for example at least one reduced current pattern and/or at least one reduced pattern of interest, from the comparison pattern, for example the current pattern and/or the pattern of interest, wherein, during the pattern recognition step, the reduced comparison pattern can be used to search for one or more patterns corresponding to the comparison pattern. By way of example, it is possible, during a coarse pattern recognition step, firstly to use a reduced comparison pattern, for example a reduced current pattern and/or a reduced pattern of interest, for searching for possible candidate patterns, which correspond to the comparison pattern, before, optionally, at least one refined pattern recognition step is then carried out, for example using at least one non-reduced comparison pattern and/or using at least one less-reduced comparison pattern. This transition to the optional at least one refined pattern recognition step can be carried out in different ways and over different gradations, and so, for example, it is possible to carry out one or more coarse pattern recognition steps with different degrees of data reduction and/or one or more refined pattern recognition steps with different degrees of data reduction. Thus, for example, at least one coarse pattern recognition step can transition into at least one refined pattern recognition step, in particular with virtually no noticeable transition, during which a degree of data reduction is reduced, for example by nesting intervals.

As an alternative to using the data reduction step for generating a reduced comparison pattern, or in addition thereto, the data reduction step can also be used for generating a reduced candidate pattern in the measurement data record, for example in the historical measurement data of the measurement data record. Various combination options are feasible.

In principle, the data reduction step can in this case comprise any data reduction and/or data compression designed to generate a data stock of the measurement data record or part thereof, for example of the comparison pattern, in particular the current pattern and/or the pattern of interest, and/or of the candidate pattern. In particular, the data reduction can be brought about by selecting representative measurement data from the data of the measurement data record and not considering the remaining measurement data. In another alternative or in addition thereto, a plurality of measurement data can also be replaced during data compression by respectively representative measurement data, which has a lower data depth and/or consists of fewer numbers. Various methods for data compression are known in principle from the prior art and can also be utilized within the scope of the present invention.

By way of example, data reduction can easily be achieved by modifying a temporal grid, for example by only assigning measurement values to the reduced measurement data record at specific times, for example at specific time intervals. However, within the scope of the present invention, an indexing method is particularly preferred; it will still be explained in more detail in an exemplary fashion below. Within the scope of the present invention, the reduced measurement data record can be stored, in particular in addition to the non-reduced measurement data record. Thus, for example, as explained above, at least one reduced comparison pattern can be generated from the comparison pattern as a result of the data reduction step, for example by a reduced current pattern being generated from the current pattern and/or by at least one reduced pattern of interest being generated from the pattern of interest as a result of the data reduction step. This reduced comparison pattern can be stored in addition to the comparison pattern and can, for example, firstly be used for a coarse search for candidate patterns before, if suitable candidate patterns are identified, the non-reduced comparison pattern can then be used for a refined comparison.

In particular, the data reduction can be brought about continuously in the data reduction step, for example in the background. By way of example, there can be online data reduction and/or real-time data reduction by, for example, checking each newly added measurement value in respect of satisfying specific criteria and then discarding or using it for the reduced measurement data record or, optionally, using it in a modified fashion.

If a reduced measurement data record is generated, with complete or partial data reduction of the measurement data record or parts thereof, this reduced measurement data record can optionally be stored. By way of example, it can be stored in a volatile data buffer and/or a non-volatile data buffer.

There can preferably be a data reduction that, in the following text, is also referred to as indexing. In this type of data reduction that can be used as an alternative to other forms of data reduction, or in addition thereto, a plurality of measurement value levels are prescribed in the data reduction step. By way of example, in the case of a blood-glucose measurement these can be concentration levels that can usually occur, for example a blood-glucose mesh in steps of 10 mg/dl or 20 mg/dl. In principle, other types of meshes are also possible. This makes it possible to subject the data in the measurement data record to a temporal grid and/or a measurement-value level grid.

The measurement value levels can be used for data reduction in various ways, which can be used alternatively or cumulatively. By way of example, those measurement values that are closest to the measurement value levels can be assigned to the reduced measurement data record. Here, use can be made of precisely these measurement values, or else use can also be made of modified measurement values, which are generated by virtue of the fact that the measurement values lying closest to the measurement value levels are rounded up or down to the measurement value levels.

As another alternative, or in addition thereto, it is, in particular, possible to identify in the data reduction step when a measurement value level is crossed between two measurement values adjacent in time. By way of example, if a measurement value at a time t lies below a prescribed measurement value level and a subsequent measurement value at a time $t+\Delta t$ lies above a measurement value level, or vice versa, it is possible to identify a crossing of the measurement value level. By way of example, in this case the data reduction step can be carried out such that, of the temporally adjacent measurement values, merely the measurement value that is closer to the measurement value level is assigned to the reduced measurement data record. By way of example, measurement values between which no measurement value level is crossed and in which a measurement value level is not crossed either during the transition to further adjacent measurement values can be discarded and not assigned to the reduced measurement data record.

Furthermore, it is particularly preferred for local extremals to be excluded from the reduced measurement data record. In particular, this is justified by virtue of the fact that extremals can more easily lead to erroneous assignments during coarse pattern recognition than measurement values that do not constitute local extremals.

As described above, the data reduction step can relate to the entire measurement data record or merely to part thereof, and can optionally take place in addition to a complete or partial retention of the non-reduced measurement data record. In particular, as illustrated above, the comparison pattern can, in the data reduction step, be reduced to at least one reduced comparison pattern, and at least part of the pattern recognition step can be carried out using the reduced comparison pattern. In particular, this can be carried out in such a way that the pattern recognition step comprises at least one coarse pattern recognition step carried out using the reduced comparison pattern. The coarse pattern recognition step can be used to identify candidate patterns that potentially correspond to the comparison pattern. As described above, the coarse pattern recognition step can in particular be carried out point-by-point, for example starting from an initial point, wherein, point-by-point, there is a measurement value comparison between the reduced comparison pattern and points of the candidate pattern. This point-by-point measurement value comparison can optionally be terminated if there is no correspondence in one or more comparisons, and so no more comparisons are carried out and the candidate pattern can, for example, be discarded. At least one refined pattern recognition step can optionally be carried out if a candidate pattern is successfully identified in the coarse pattern recognition step, wherein the candidate pattern can be compared to the comparison pattern, i.e. the non-reduced comparison pattern, in the refined pattern recognition step. This comparison can, in turn, also be effected point-by-point. Instead of a simple division into a coarse pattern recognition step and a refined pattern recognition step, it is also possible to insert further intermediate steps of pattern recognition steps, for example by successively carrying out more refined pattern recognition steps with smaller time steps and/or with larger data records.

As explained above, the coarse pattern recognition step can, in particular, be carried out step-by-step, wherein the coarse pattern recognition step can be terminated if a non-correspondence is determined. There can also be an analogous procedure during the refined pattern recognition step and/or during other pattern recognition steps.

In particular, as described above, at least one tolerance can be prescribed in the pattern recognition step, wherein correspondence within the scope of the tolerance is identified as sufficient. By way of example, the at least one tolerance can be prescribed in respect of the measurement times and/or in respect of the measurement values. As illustrated above, the tolerances can be prescribed fixedly or else variably for individual measurement values or measurement points, and the individual measurement values can also be included in the check for correspondence in a weighted fashion. By way of example, the tolerances can be prescribed point-by-point for the measurement values in the comparison pattern and/or the reduced comparison pattern and/or the candidate pattern. By way of example, the tolerances can be prescribed by one or more tolerance thresholds and/or one or more confidence intervals, which may be arranged symmetrically or else asymmetrically around the measurement values, or in another fashion. In particular, a plurality of tolerances can be prescribed for different measurement values at different measurement times, wherein, preferably, measurement values of the comparison pattern, e.g. the current pattern and/or the pattern of interest, and/or the reduced comparison pattern and/or the candidate pattern that lie further back in time are provided with greater tolerances than more recent measurement values.

A further possible embodiment of the proposed method consists of it being possible to store one or more boundary conditions in addition to the measurement values and, optionally, to the measurement times. By way of example, these boundary conditions can be stored in the measurement data record and be part of the measurement data record; this is assumed in the following text without restricting further possible embodiments. However, alternatively, or in addition thereto, the one or more boundary conditions can also be stored independently of the measurement data record, for example at a different buffer location or in a different buffer. In general terms, reference is made to the fact that the measurement data record can also be stored in a single buffer and/or contiguously; however, in principle storage can also take place in a plurality of parts, which, for example, can be stored in a plurality of different buffers.

The boundary conditions can, in particular, characterize events that have a potential physiological influence on the body of the user. The events can be punctiform, i.e. have a negligible duration compared to the overall measurement, but can in principle also extend over a relatively long period of time. By way of example, the boundary conditions can likewise be assigned to one or more specific times or time periods, which can correspond to one or more of the measurement times but which can also be selected independently of the measurement times of the measurement data record. In particular, the boundary conditions can be or comprise one or more of the following boundary conditions: a type and/or amount of medication, in particular an insulin bolus; a type and/or amount of food intake; an illness; a time of day; a stress load on the user; bodily well-being of the user; at least one further physiological parameter, for example at least one hormone concentration and/or a blood pressure; a specific bodily situation, e.g. a monthly period; a type and/or duration and/or intensity of physical exertion; at least one specific bodily situation; fever; headache; backache; a specific mental situation.

In particular, the at least one boundary condition can also be taken into account in the pattern recognition step. By way of example, if the current pattern contains at least one boundary condition, patterns that correspond to the current pattern and likewise comprise the at least one boundary condition, preferably at corresponding times, can for example be sought after in the pattern recognition step. By way of example, the one or more boundary conditions can even be taken into account during the coarse pattern recognition step, for example by primarily searching for candidate patterns that likewise have the at least one boundary condition.

In particular, at least one measurement value acquired at an anchor time can be specified as an anchor value during the pattern selection step. By way of example, the anchor time can be a current measurement time and/or a measurement time of interest. If the anchor time is a current measurement time, the anchor value can for example be a current measurement value. By way of example, the current measurement value can be a current measurement value that satisfies at least one anchor value condition. By way of example, this anchor value condition may emerge from the data reduction step. Hence, for example, the at least one anchor value can be the most recent current measurement value that satisfies the optional data reduction condition used in the data reduction. By way of example, the above-described indexing can be used such that, when a measurement curve crosses one or more prescribed measurement value levels, the measurement value closer to this measurement value level is respectively assigned to the reduced measurement data record. By way of example, the respectively most recent measurement value that satisfies this indexing condition can, preferably provided this measurement value does not form a local extremum, be selected as anchor point, in particular automatically and/or online, in particular real-time. However, in principle, other selection criteria for an anchor value are also possible. Thus, for example, the anchor value can be a measurement value of interest recorded at a measurement time of interest. By way of example, the measurement time of interest can be selectable by the user. Other embodiments are also possible.

In particular, the anchor value can be a measurement value of the reduced measurement data record, for example the most recent measurement value in this reduced measurement data record and/or a measurement value, selected by the user, in the reduced measurement data record. By way of example, the most recent measurement value at which the curve of the measurement values cuts one of the measurement value levels can be used as anchor value and the time at which this happens can be used as current time. Alternatively, or in addition thereto, the anchor time and/or the anchor value can also be selectable by the user, for example as per one or more of the above-described selection methods.

The at least one anchor value can be used in the pattern selection step and/or in the pattern recognition step. Thus, the comparison time interval in the pattern selection step can for example be a time interval that comprises the anchor time, adjoins the anchor time or is defined relative to the anchor time in any other way. By way of example, the comparison time interval can be defined as time interval that starts at a prescribed time interval before the anchor time begins and/or ends, in a prescribed fashion, before or after the anchor time. In particular, the comparison time interval can comprise the anchor time, adjoin the latter or be defined relative thereto in any other fashion. The comparison pattern can comprise the measurement values, which were recorded during the comparison time interval, and, optionally, the measurement times assigned thereto. In particular, the comparison pattern can comprise the anchor value itself; however, this is not mandatory.

Furthermore, the at least one anchor value can, alternatively or additionally, be utilized in the at least one pattern recognition step. In particular, candidate values that correspond to the anchor value and are respectively recorded at candidate times can be sought after in the measurement data record during the pattern recognition step. Thus, for example, candidate values that correspond to the anchor value can be sought after step-by-step into the past, or by another fashion. Once again, correspondence should be understood to mean identity or else correspondence within the scope of one or more prescribed tolerances, and so, for example, candidate values can also be measurement values that may lie within a tolerance interval around the anchor value. As described above, one or more boundary conditions can also be taken into account during this search for possible candidate values, and so, for example, there can primarily be a search for candidate values that were, for example, like-wise stored in the measurement data record under one or more boundary conditions or in conjunction with one or more boundary conditions. Here, for example, the one or more boundary conditions can be included in the search such that candidate values are sought after in which, for example, one or more identical or similar boundary conditions were recorded within a temporal tolerance interval like, for example, within a temporal tolerance interval about the anchor time.

In particular, the search for candidate values can once again be performed step-by-step, for example step-by-step into the past. If one or more candidate values, with respectively assigned candidate times, were identified, it is in particular possible to define a candidate time interval about these candidate values, which candidate time interval corresponds to the current time interval, for example in terms of its duration and/or its relative alignment with respect to the candidate time. Thus, for example, the candidate time interval can be defined such that the latter begins at the same time from the candidate time as the current time interval does from the current measurement time. Alternatively, or in addition thereto, the end of the candidate time interval can be fixed such that this has the same time from the candidate time as the end of the comparison time interval to the anchor time. In this and/or another fashion, it is possible to determine at least one time interval, more particularly respectively at least one time interval, in respect of the at least one established candidate time, which at least one time interval is to the established candidate time like the comparison time interval is to the anchor time. The measurement values acquired during the candidate time interval and, optionally, the associated measurement times, can be identified as candidate pattern. The candidate pattern can be compared to the comparison pattern during the pattern recognition step, e.g. once again in a single step or else in a plurality of steps, for example first in a coarse pattern identification step and, optionally, subsequently in at least one refined pattern recognition step. In particular, the pattern comparison between the candidate pattern and the comparison pattern can, once again, as described above, be carried out point-by-point and/or can be subjected to termination criteria in order optionally to be able to accelerate the pattern comparison and terminate it prematurely. One or more boundary conditions in the measurement data record can, once again, also be taken into account during the search for candidate values, as described above. In particular, the pattern recognition step can, once again, be carried out step-by-step, wherein, starting from the candidate time, there is preferably firstly a coarse pattern recognition step and subsequently, if the coarse pattern recognition step has led to correspondence, at least one refined pattern recognition step. In particular, the pattern recognition step can, starting from the candidate time, go step-by-step back into the past. However, in principle, other search directions or search schemes are also possible.

In particular, the proposed method in one or more of the above-described embodiments can be carried out online, preferably real-time. In particular, the measurement data record can be updated, for example continuously or else discontinuously, by newly added measurement values. The pattern selection step and the pattern recognition step can then, respectively or together, be repeated with the newly added measurement values, preferably with each newly added measurement value. In particular, this repetition can take place automatically, without this requiring a user action;

it can for example be triggered by the addition of a new measurement value and/or by the addition of a new boundary condition.

In order to avoid too significant increases in the data stock of the measurement data record and, optionally, an increase in the method duration required for the method connected to this, the measurement data record can also be modified at regular or irregular intervals by deleting individual or a number of data entries and/or by overwriting this data. Thus, for example, the method can be carried out such that if new measurement values are added, the oldest measurement values in the data record are deleted and/or overwritten. By way of example, use can be made of a circular buffer and/or a first in, first out (FIFO) buffer for this purpose. By way of example, the measurement data record can always comprise measurement values of a measurement period of equal length, in particular a length of between 1 week and 6 months, preferably between 1 month and 5 months, and particularly preferably 3 months. However, in principle, other measurement periods are also possible. In particular, as described above, measurement values can, during the data acquisition step, be acquired at regular or irregular time intervals. In particular, data acquisition is possible in which measurement values are acquired at time intervals from 1 min up to 10 min, preferably at time intervals of 5 min. The data record can be provided by a data base as mentioned further below.

In particular, the pattern recognition step can be carried out repeatedly. The pattern recognition step can be provided by a pattern matching algorithm as mentioned further below. In particular, this can be brought about by virtue of the fact that, in the case of repetitions, measurement values of the measurement data record that in each case further back in time are taken into account. Thus, for example, the pattern recognition step can be carried out point-by-point and step-by-step into the past, for example starting from the anchor time, for example the current time, and/or the candidate time. If provision is made for a plurality of pattern recognition steps, for example in the form of at least one coarse pattern recognition step and at least one refined pattern recognition step, these pattern recognition steps can each be carried out point-by-point into the past, for example with the above-described termination criteria if a non-correspondence of one or more measurement values is determined.

Further possible embodiments of the proposed method relate to the case in which one or more patterns are established that correspond to the comparison pattern. Thus, in one possible method variant, the method can be carried out such that if at least one pattern corresponding to the comparison pattern is found, a correspondence is quantified, in particular by means of at least one correlation. By way of example, discrete or continuous correlation functions may be applied in order to quantify the correspondence between the comparison pattern, e.g. the current pattern and/or the pattern of interest, and the corresponding pattern, for example by means of at least one correlation value. However, in principle, other quantifications of the degree of correspondence may also be used as an alternative or in addition thereto, for example a mean value of the deviations of the individual measurement values or similar quantifications. In particular, the result of this quantification can be flagged to the user and/or a treating medical practitioner or be processed in other means, for example by transmission to one or more instruments or instrument components, for example to at least one medical-practitioner computer.

According to a first alternative, the quantification of the correspondence relates to the candidate values and the measurement data record including a bias. The bias represents the absolute level of the candidate values and the measurement data record. The bias is substantially constant over time. In particular, the bias relates to a base level which is constant over time or varies slowly, wherein the variation is substantially slower variations defined by the pattern. Further, the bias can vary according to drifts occurring to a sensor due to aging. A bias being substantially constant over time includes both, a bias being constant over time as well as a bias, which varies slowly. This slow variation is substantially slower than the variations of the pattern, i.e. the variations reflected by a dynamic representation of the candidate values and/or the measurement data record.

According to a second alternative, the quantification of the correspondence relates to a dynamic representation of the candidate values and/or the measurement data record. The dynamic representation excludes the bias. The dynamic representation reflects variations due to metabolism processes of the patient and/or due to changes in the metabolism of the patient, e.g., due to boundary conditions as given herein. Again, the bias not included by the dynamic representation reflects the absolute level of the candidate values and the measurement data record.

Thus, in the first alternative, the bias, is also addressed when providing the correspondence, in addition to the dynamic representation. In the second alternative, only dynamically varying components of the candidate values and the measurement data record are addressed. The dynamic variation reflects the shape of a pattern and does not include constant or only slowly varying components reflected by the bias. The second alternative provides a full correspondence, if the dynamic variation, i.e. the development or progression of the candidate values, corresponds to the development or progression of the measurement data record. In the first alternative, a full correspondence is given, if additionally the constant or only slowly varying bias or level of the candidate values corresponds to the bias or level of the measurement data record. The anchor value as given herein can be seen as bias. A variation rate limit or a corresponding limit frequency can be predefined in order to distinguish the dynamic representation from the bias.

According to the invention, the quantification of the correspondence relates to the candidate values and the measurement data record including the bias. The bias is substantially constant over time. Alternatively, the quantification of the correspondence relates to a dynamic representation of the candidate values and a dynamic representation of the measurement data record excluding the bias. In particular, the bias represents the absolute level of the candidate values and the measurement data record.

The method can comprise the above-described method steps in the illustrated sequence or else in another sequence. In particular, one or more method steps can be carried out iteratively or repeatedly. In particular, the method can be carried out in such a way that the pattern selection step and the pattern recognition step are carried out iteratively, for example by carrying out the pattern selection step and, subsequently, the pattern recognition step with each newly added measurement value or, respectively, with selected newly added measurement values.

The method or part thereof, in particular the pattern selection and/or pattern recognition steps can be initiated in various ways. By way of example, there may be an automatic start as an alternative to a manual start or in addition thereto. By way of example, the method and/or one or both of the pattern selection and pattern recognition steps can be started automatically when a new measurement value was acquired. In another alternative, or in addition thereto, there may for example be an automatic start of the method and/or one or both of the pattern selection and pattern recognition steps when a new boundary condition is recorded, for example if a new electronic diary entry is recorded, for example a food intake, and/or if another type of boundary condition is recorded by automatic acquisition and/or manual entry. In another alternative or in addition thereto, other events can act as method-triggering events.

Furthermore, the method can in particular comprise at least one interaction step, wherein, during the interaction step, at least one result of the pattern recognition step is processed and/or flagged to the user. In this respect, the term "processing" should be considered quite broad and in principle comprises every possible automatic, semiautomatic or manual action that can be carried out using the result of the pattern recognition step. In particular, processing can comprise storing, transmitting, displaying, combining with other results or other method steps.

If the result of the pattern recognition step is flagged to the user, this can be brought about in different ways, for example electronically, visually, acoustically, haptically or by combining the aforementioned and/or other options. In particular, there can be a display on a display element. In particular, at least one pattern, identified during the pattern recognition step and corresponding to the comparison pattern, can be displayed by means of at least one display element during the interaction step.

Furthermore, at least one possible future profile of the measurement values can, alternatively or additionally, be established and/or displayed in the interaction step, for example by means of at least one display element. In general, the at least one possible future profile can for example be displayed, stored, transmitted or used in any other fashion.

By way of example, the method can be carried out such that the comparison pattern, in particular the current pattern and/or the pattern of interest, and at least one pattern that was established in the pattern recognition step and corresponds to the comparison pattern are displayed in the interaction step. Optionally, at least one error corridor can furthermore be displayed in the interaction step.

Furthermore, at least one boundary condition, which correlates in time with the corresponding pattern, can alternatively or additionally be displayed in the interaction step. By way of example, a boundary condition correlating in time can be understood to mean a boundary condition that was recorded within the time interval within which the corresponding pattern was acquired or a boundary condition which is in close temporal context with this time interval, for example by being recorded outside of this time interval by no more than a prescribed time tolerance. By way of example, time tolerances of a few minutes up to an hour can be prescribed as boundary condition in the case of food intake.

Furthermore, at least one possible future profile of the measurement data record can be displayed in the interaction step. In particular, a possible future profile of the measurement values, which profile has joined the pattern that corresponds to the comparison pattern, in particular the current pattern and/or the pattern of interest, can, during the interaction step, be displayed in graph-form on the display element, superposed on the current pattern. In place of displaying a single established corresponding pattern, or in addition thereto, it is also possible to create an overall pattern established from a plurality of corresponding patterns, for example an averaged pattern. In general terms, during the interaction step, it is possible, for example, to subject one or more patterns, identified in the pattern recognition step and corresponding to the comparison pattern, to an analysis, in particular a statistical analysis, preferably under formation of an averaged pattern and/or an error corridor. In the process, at least one averaged pattern in particular can be created and, optionally, be displayed.

By way of example, a future profile of the measurement values can be calculated on the basis of one or more prescribed algorithms. By way of example, such algorithms may comprise an averaging of the profile of the pattern established in the pattern recognition step and/or another method for predicting the future profile. By way of example, the future profile can be established starting from the current time and/or the now-time. By way of example, the future profile can, as illustrated above, be displayed, stored, transmitted (for example to another device, for example to a computer or a further computer) or used in any other way. Further, the comparison pattern corresponding to the candidate pattern can be displayed or can be provided as an output in another way. Preferably, a boundary condition associated to the comparison pattern can be displayed or can be provided as an output in another way.

The at least one algorithm, which can be utilized to calculate a future profile in advance, can, in principle, also be wholly or partly identical to at least one algorithm that is also used in the at least one pattern identification step. In principle, the at least one algorithm can be fixedly prescribed or else can be embodied in a variable fashion, for example it can be updated with new discoveries. The at least one algorithm and/or the possible future profile of the measurement values predicted by means of this algorithm can for example also be modifiable dependent on behaviour of the user and/or therapy. By way of example, it is possible for a plurality of probable future profiles to be established, dependent on different behaviours and/or different therapies. By way of example, different therapy suggestions can lead to different predicted future profiles of the measurement values. By way of example, these different profiles may also be displayed during the interaction step or be used in a different fashion.

Alternatively, or in addition thereto, at least one instruction for the user can be generated in the interaction step and, optionally, output, for example by a graphical and/or acoustic and/or haptic representation. In particular, this instruction may be selected from one or more of the following instructions: a warning in respect of the presence of a critical physiological body state; a warning in respect of a possible critical physiological body state coming up in the near future; a suggestion to consult a medical expert, in particular a medical practitioner, a suggestion in respect of medication; a behavioural suggestion, in particular in respect of food intake and/or physical exertion.

As explained above, one, more or all method steps can be carried out, even repeatedly, on their own or in groups, Thus, for example, repeated selection of a comparison time interval can finally cover all the time, or some of the time, during which measurement values were acquired, and/or a plurality of comparison time intervals and/or a plurality of possible comparison patterns can be selected, for example in succession, in order to search for corresponding patterns in the respective pattern recognition steps. Thus, in a preferred embodiment of the method, the aforementioned pattern selection and pattern recognition steps and, optionally, the interaction step are carried out repeatedly, wherein a plurality of comparison patterns of the measurement data record are selected, preferably in succession, and wherein at least one pattern recognition step is carried out using each of the selected comparison patterns. The term "a plurality of comparison patterns" in this case comprises at least two comparison patterns, preferably more than two and e.g. at least 10%, in particular at least 50% or even at least 80% or at least 90% of all possible comparison patterns that are selectable from the measurement data record, wherein even all possible comparison patterns are selectable, i.e. 100% of the possible comparison patterns. However, methods are also feasible in which it is not the case that all possible comparison patterns that are selectable from the measurement data record are selected, but merely e.g. a subset of these possible comparison patterns, e.g. the possible comparison patterns that are respectively acquired at a particular day of the week or similar subsets.

The correspondences respectively optionally resulting from the pattern recognition steps can optionally be combined in groups. In a preferred embodiment, the method is thus carried out such that corresponding patterns established during the pattern recognition steps are combined into groups of respectively corresponding patterns. Thus, for example, one or more groups of corresponding patterns can be formed, which can respectively comprise one or more patterns that correspond to one another. By way of example, a first group may be formed, wherein a first type of patterns is contained in the first group, wherein the patterns in the first group correspond to one another, wherein, preferably, at least a second group is formed, wherein a second type of patterns is contained in the second group, which patterns correspond to one another, wherein, preferably, further groups with further types of patterns are formed, which patterns correspond to one another. By way of example, the groups can be formed such that it is respectively recognized during the pattern selection step whether the respectively selected comparison pattern has already been assigned to a group. If this is the case, those patterns that correspond to the comparison pattern and are established in the associated pattern recognition step are likewise assigned to this group. If this is not the case and if the respectively selected comparison pattern does not yet belong to a group, a new group may be formed, the comparison pattern can be assigned to this new group and those patterns that correspond to the comparison pattern and are established in the associated pattern recognition step can be assigned to the new group.

In general, it is possible to form one or more groups of corresponding patterns. The groups of corresponding patterns can be subjected to at least one analysis, in particular a statistical analysis, in particular by comparing the found groups. Thus, for example, frequency distributions of the groups and/or other statistical analyses may be formed. Furthermore, it is alternatively or additionally possible for e.g. at least one result of this group formation also to be used in the at least one optional interaction step. Thus, for example, the established groups can be flagged to a user and/or to another instrument, for example by flagging the groups and/or at least one result of at least one analysis to a user by means of at least one display element.

A computer program is proposed in a further aspect of the present invention, which computer program has program code for carrying out the method as per one or more of the above-described embodiments when the program is executed on a computer and/or a processor and/or a computer network. Here, in principle, a computer can be understood to mean any electronic data processing device that can be embodied to carry out a program. The data processing device can comprise one or more processors and, optionally, one or more volatile and/or non-volatile data buffers. The data processing device can also, wholly or partly, be integrated in at least one instrument that, in addition to data processing, can serve at least one further purpose, for example a mobile telephone like e.g. a smartphone. Here, a computer network should be understood to mean a collection of at least two computers that can interact and that can interchange data or instructions, for example, via one or more wireless or wired connections such as the Internet or a local area network for example. In particular, the computer program can be stored on a machine-readable carrier.

The computer program can, in particular, comprise program code means for carrying out one configuration of the method according to the invention. In particular, the program code means can be stored on a computer-readable data medium. Furthermore, a data medium is proposed, on which a data structure is stored, which, after being loaded into random access memory and/or main memory of a computer or computer network, can execute one configuration of the method according to the invention.

A computer program product is furthermore proposed, with program code means, stored on a machine-readable medium, for carrying out one configuration of the method according to the invention when the program is executed on a computer or computer network. Here, within the scope of a computer program product the program is understood to mean a tradable product. In principle, it can be present in any form, for example on paper or a computer-readable data medium, or it can in particular be distributed over a data transmission network.

A device for analysing physiological measurement values of a user is proposed in a further aspect of the present invention. In particular, the device can be embodied to carry out a method as per one or more of the above-described embodiments. Accordingly, in respect of possible embodiments of the device, reference can largely be made to the above description of optional embodiments of the method. In particular, the device can comprise at least one data processing device, in particular a microcontroller, which can be configured in terms of programming to carry out the method steps as per one or more of the above-described embodiments. Device for analysing physiological measurement values of a user and patient monitoring system are equivalent terms for the same subject-matter.

In one embodiment, the device comprises: at least one data acquisition device for acquiring physiological measurement values of the user and storing these in at least one measurement data record. Here, the data acquisition, as described above, should be considered in very broad terms and can, in principle, comprise the actual measurement, but may also comprise adopting derived data, which is derived from the actual measurement data, and/or adopting data from another device. Accordingly, the data acquisition device may for example comprise a measurement device and/or an interface for adopting physiological measurement values from another device, for example an external sensor. The function of data acquisition can also be provided by a physiological data input device as mentioned further below.

In one embodiment, the device also comprises: at least one pattern selection device, wherein the pattern selection device is designed to select measurement values acquired during at least one comparison time interval as at least one comparison pattern. The pattern selection device may, in particular, wholly or partly be a component of a data processing device, for example a computer, microcomputer or similar data processing devices. In particular, the pattern selection device can comprise a data processing device, configured in terms of programming for implementing the above-described pattern selection step in one or more of the above-described embodiments.

In one embodiment, the device also comprises: at least one pattern recognition device, wherein the pattern recognition device is designed to search for patterns corresponding to the comparison pattern in the measurement data record. This pattern recognition device can also wholly or partly be implemented as a component of a data processing device, in particular of a data processing device configured in terms of programming for carrying out a pattern recognition step as per one or more of the above-described embodiments. This data processing device may be wholly or partly identical, in terms of components, to the data processing device in which the pattern selection device may be wholly or partly comprised such that, for example, components b) and c) can be wholly or partly implemented as an identical component. The pattern recognition device can be implemented by the processor mentioned further below.

The device can furthermore comprise at least one measurement device for measuring physiological measurement values, in particular at least one sensor, for example a long-term sensor for long-term analyte acquisition as per one or more of the above-described embodiments. Other embodiments are also feasible.

The device for analysing physiological measurement values can have an integral or else a multipart design, i.e. it can be embodied as a central system or else, for example, as a decentralized device with a plurality of individual components, which can preferably communicate with one another. Accordingly, the at least one measurement device can also, for example, be integrated into one or more other components of the device for analysing physiological measurement values; however, it can also be connected to these components to form e.g. a system and communicate with one or more of these components, for example via one or more interfaces, which may for example have a wired or wireless design.

In particular, the device for analysing physiological measurement values may comprise at least one hand-held instrument. By way of example, this hand-held instrument can be embodied such that it can be carried along in a pocket, e.g. a jacket pocket or a trouser pocket, by a user. The hand-held instrument can accordingly for example comprise dimensions, which are no more than 20 cm in any dimension, in particular no more than 15 cm in any dimension. By way of example, the hand-held instrument can also be wholly or partly integrated into other types of hand-held instruments, for example mobile telecommunication instruments such as mobile phones, in particular smartphones, into mobile data processing instruments such as personal digital assistants (PDAs) or other mobile hand-held instruments. In particular, the data acquisition device, the pattern selection device and the pattern recognition device can each be a component of the hand-held instrument, at least in part.

The proposed method, the computer program and the device have a number of advantages over known methods, computer programs and devices of the aforementioned type. In particular, the invention provides the option of automatic, e.g. retrospective, consideration of measured measurement values, e.g. current glucose measurement values or glucose measurement values of interest, and historical data and/or other data in a measurement data record. Here, particular attention can be given to the earlier profile of this measurement value, for example in order to find a historical situation of the user that is as identical as possible to the current situation of the user, in order for example to give the user the option of reacting in an ideal fashion to the current situation. To this end, use can be made not only of the measurement values and their profiles, but also of other values and/or boundary conditions such as e.g. the insulin bolus, the time of day, stress levels or other events such as e.g. meals, physical activities or physical sensitivities, in order to be able to find and display the ideal historical measurement time. The optionally proposed method of data reduction in particular allows subjecting the measurement data to a temporal grid, which offers a quick option for comparing measurement profiles to one another. Accordingly, it is also easy to implement the proposed method online and preferably as a real-time method, in small hand-held instruments. Furthermore, the method generally does not require any user interaction, in contrast to the described methods from the prior art discussed above. The method can in particular run in real-time, online and, preferably, completely in the background.

In particular, the method can be carried out such that a possible further profile is established from one or more of the patterns in the measurement data record, which patterns were established to correspond to the comparison pattern. By way of example, a current profile and a possible or probable further profile of the measurement data record can be displayed. By way of example, the further profile can be made to be dependent on a degree of correspondence between the comparison pattern and the established pattern. Furthermore, one or more boundary conditions may optionally also be established, which boundary conditions, for example, have shown a positive effect in the past and could also constitute expedient measures within the scope of the current profile of the physiological measurement data.

The comparison pattern, for example the current pattern, can in particular form a portion, more particularly a current portion, from continuous monitoring data. The search for the portions fitting to the portion, for example for historical portions fitting to the current portion, which is often also referred to as pattern matching, can be carried out in an automated fashion and, in particular, in an optimized fashion by using the above-described indexing method in the current data stock or in the archive of historical data of a patient who uses continuous monitoring measurements. If a search request is made, this search can at that time analyse the data stock, in particular based on the aforementioned indexing, which can be undertaken in the background, in particular when new measurement values are stored.

In respect of possible boundary conditions, knowledge about the history collected in e.g. diary entries, which are available in parallel, can be set in relation to the then and current profile of the measurement data. In particular, by comparing the currently current profile, i.e. the current pattern, to the earlier profile, in particular identified candidate patterns, in particular at all possible times, preferably taking into account the earlier boundary conditions (e.g. diary information in respect of time of day, meals, therapy, movement, individual factors such as illness or stress or similar boundary conditions) can lead to in-depth understanding about the metabolic situation and about regularities and observable deviations. Moreover, a potential wrong development can be indicated by a warning message such that the user has more time for appropriate corrective measures. Preferably, other values and/or boundary conditions as exemplarily listed above on one hand and data tags or relevant data tags concern the same feature. In particular, the other values and/or boundary conditions can be used as data tags and the data tags can be used as other values and/or boundary conditions as listed herein. The data tags, other values and/or boundary conditions can be associated to physical measurement values, to a time interval at which physical measurement values are acquired, to a data set, in particular a time window data set as given herein, or to a feature similar to a data set or to a time window data set.

Furthermore, additional information can be provided to the user as to how he can influence possible future developments. This method can assist with reacting in a current situation as a result of a fast reaction time, and can alternatively retrospectively support the evaluation of historical data.

In the following, the invention is disclosed by general examples, which can be combined with embodiments or features given throughout the description, the claims and the figures and, in particular, given in FIGS. 4-20 and the description passages referring thereto.

In one example, a patient monitoring system is disclosed. The system may comprise: a physiological data input device which acquires a plurality of physiological measurements of the patient within a time window thereby generating at least one time window data set; a memory storing a pattern matching algorithm; a database to store the at least one time window data set; and a processor in communication with said input device to receive said generated at least one time window data set, and in communication with said memory in order to execute said pattern matching algorithm. The pattern matching algorithm when executed by said processor causes said processor to compress the at least one time window data set, store the compressed at least one time window data set, and perform a pattern match between a reference pattern and the stored at least one time window data set using a distance metric provided by the pattern matching algorithm.

In another example, a non-transitory computer-readable medium is disclosed that stores a program that, when executed by a processor, causes the processor to perform at least a pattern match between a reference pattern and at least one stored time window data set collected via a patient monitoring system using a distance metric.

In still another example, a method for identifying a diabetes-related event in a patient using a patient monitoring system comprising a physiological data input device and a processor is disclosed. The method comprises receiving automatically from the physiological data input device at least one time window data set indicative of a physiological measurement related to the diabetes-related event; associating automatically using the processor the at least one time window data set with a data tag; transforming automatically using the processor the associated at least one time window data set into a normalized at least one time window data set, wherein the normalized at least one time window data set has a mean of zero and a standard deviation of one, compressing automatically using the processor the normalized at least one time window data set into a compressed at least one time window data set, and pattern matching, automatically using the processor, between a reference pattern and the compressed at least one time window data set using a distance metric.

In still another example, a method for real-time identification of a diabetes-related event in a patient using a patient monitoring system comprising a physiological data input device, a user input device and a processor is disclosed. The method comprises receiving automatically from the user input device at least one reference pattern and associated alert signal; receiving automatically from the physiological data input device at least one time window data set indicative of a physiological measurement related to the diabetes-related event; associating automatically using the processor the at least one time window data set with a data tag; transforming automatically using the processor the associated at least one time window data set into a normalized at least one time window data set, wherein the normalized at least one time window data set has a mean of zero and a standard deviation of one; compressing automatically using the processor the normalized at least one time window data set into a compressed at least one time window data set; storing automatically using the processor the compressed at least one time window data set; and pattern matching automatically using the processor between the reference pattern and the stored at least one time window data set using a distance metric, wherein when the distance metric is less than $\varepsilon$, the processor automatically triggers the alert.

BRIEF DESCRIPTION OF THE FIGURES

While the specification concludes with claims, which particularly point out and distinctly claim the invention, it is believed the present invention will be better understood from the following description of certain examples taken in conjunction with the accompanying drawings.

Further details and features of the invention emerge from the following description of exemplary embodiments. Here, the respective features can be implemented on their own or a number of them can be implemented together in combination. The invention is not restricted to the exemplary embodiments. The exemplary embodiments are illustrated schematically in the figures. In the drawings, like numerals represent like elements throughout the several views. In particular, the same reference signs in the individual figures denote equivalent or functionally equivalent elements, or elements that correspond to one another in terms of their functions.

Figure 1:
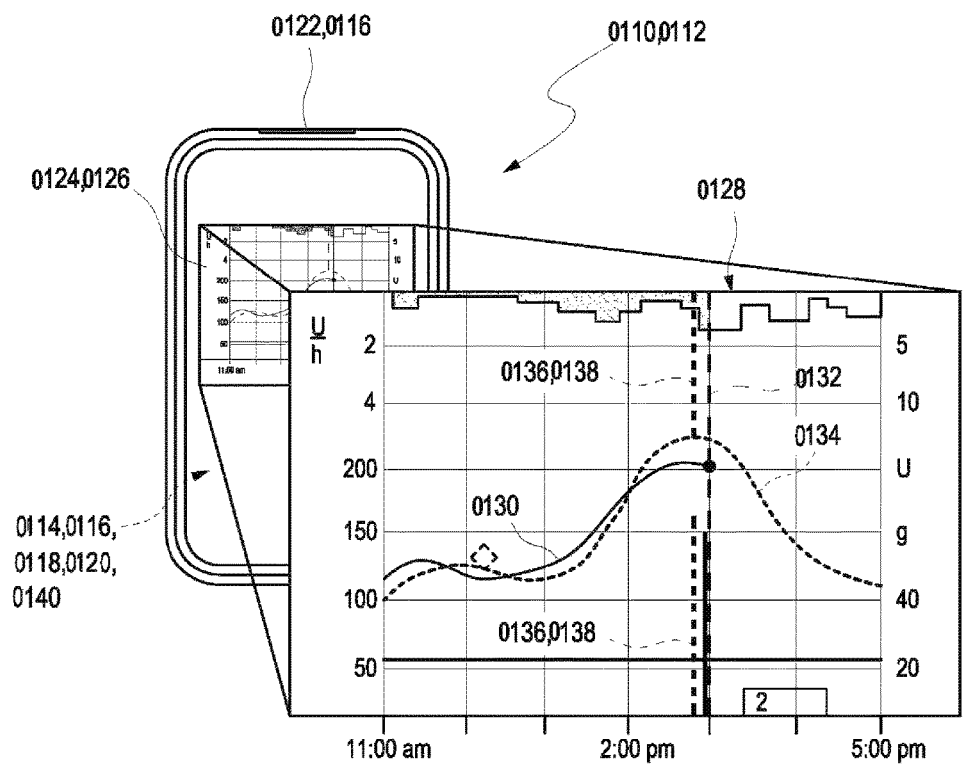
FIG. 1 shows an exemplary embodiment of a device according to the invention for analysing physiological measurement values of a user.
Figure 2:
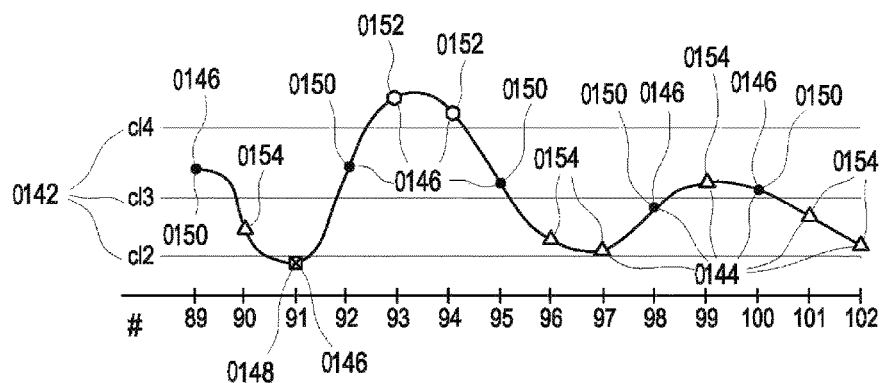
FIG. 2 shows a method for data reduction of a measurement data record.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

The following description of certain examples should not be used to limit the scope of the present invention. Other features, aspects, and advantages of the versions disclosed herein will become apparent to those skilled in the art from the following description, which is by way of illustration. As will be realized, the versions described herein are capable of other different aspects, all without departing from the invention. Accordingly, the drawings and descriptions should be regarded as illustrative in nature and not restrictive.

DETAILED DESCRIPTION OF EXEMPLARY EMBODIMENTS

FIG. 1 illustrates, in an exemplary fashion, an exemplary embodiment of a device 0110, according to the invention, for analysing physiological measurement values of a user. In the illustrated exemplary embodiment, the device 0110 is embodied as a hand-held instrument 0112, which can for example comprise at least one data processing device 0114, which is merely indicated in FIG. 1. By way of example, this data processing device can also act as data acquisition device 0116, as pattern selection device 0118 or as pattern recognition device 0120 or as part of one or more of the aforementioned devices. Furthermore, the hand-held instrument 0112 can comprise one or more interfaces 0122, likewise merely indicated in FIG. 1, for example one or more wireless interfaces, which can likewise act as a component of the data acquisition device 0116. By way of example, the hand-held instrument 0112 can communicate with a sensor element via the interface 0122, which can for example be a wireless interface, and comprise measurement values. Furthermore, the hand-held instrument 0112 can itself optionally comprise—this is not illustrated in FIG. 1—at least one measurement device, for example a spot measurement device, for example in the form of a test-strip measurement device, in particular for carrying out calibration measurements.

The hand-held instrument 0112 can furthermore comprise one or more user interfaces 0124. In particular, the user interfaces 0124 can comprise one or more display elements 0126, as illustrated in FIG. 1, in particular one or more displays and/or touchscreens. FIG. 1 furthermore illustrates, in an enlarged illustration 0128, possible screen contents of the display element 0126. Here blood glucose concentrations are plotted, on a vertical axis in steps of 50 mg/dl, as a function of measurement time, illustrated on the horizontal axis. Here, FIG. 1 shows, in an exemplary fashion, an exemplary embodiment on the display element 0126, in which a curve 0130 of a current profile of the measurement values is illustrated up until a now-time 0132. Furthermore—this is likewise shown in FIG. 1—a possible curve 0134 may optionally be shown, which for example illustrates a reference profile, which can for example be established using a method according to the invention. By way of example, this reference profile 0134 can also be illustrated beyond the now-time 0132 and can for example thus also illustrate a probable future profile. Furthermore, one or more events 0136 can be marked; by way of example, these characterize boundary conditions 0138, for example food intake. Further details will not be discussed here in any more detail; rather, reference can for example be made to the following exemplary embodiments of a method according to the invention.

Using FIGS. 2 and 3A to 3G, an example of a method, according to the invention, for analysing physiological measurement values of a user, in particular for analysing glucose measurement values, should be explained in the following text, which method can also be implemented as a computer program, for example in the hand-held instrument 0112. The hand-held instrument 0112 can, beyond the scope of the data processing device 0114 or as a part thereof, furthermore comprise one or more data buffers 0140 for storing a measurement data record. This is also indicated symbolically in FIG. 1.

The example described in the following text can, in particular, be based on the use of a mobile continuous monitoring system. The data buffer 0140 can, in particular, be embodied as a circular buffer or FIFO buffer, and measurement values can be recorded in data acquisition steps that are carried out repeatedly or continuously. The measurement values, for example the respectively current measurement values of the last measurement periods, can optionally be collected in the data buffer 0140, for example for a period of three months. Here, the method can be embodied such that new data always overwrites the oldest entries. Alternatively, or in addition thereto, the data stock can also be wholly or partly swapped-out, for example by being transferred to a computer, e.g. a PC system, and added to a data stock there. In principle, such an overall data stock on an external instrument can also be processed using the method described here.

Figure 3:
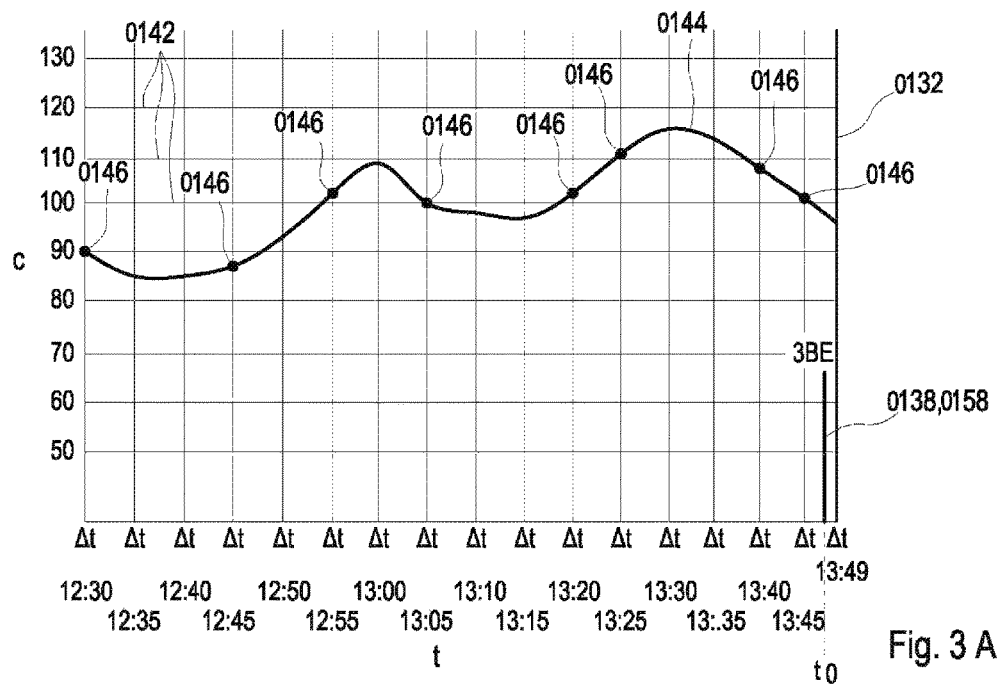
FIGS. 3A to 3G show method steps of a method according to the invention for analysing physiological measurement values of a user.
Figure 3:
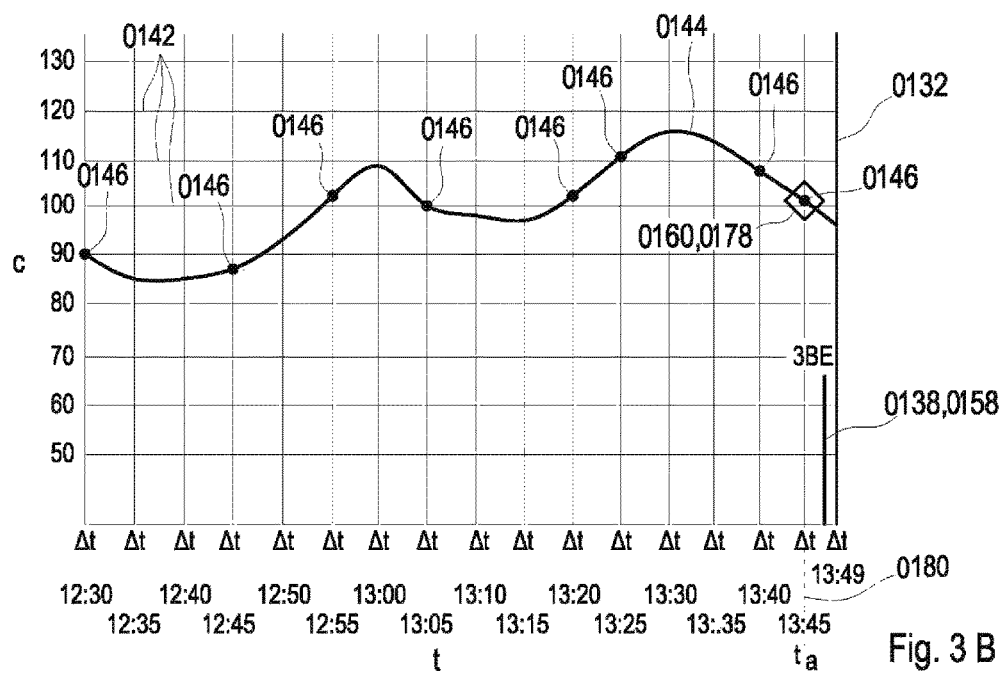
Figure 3:
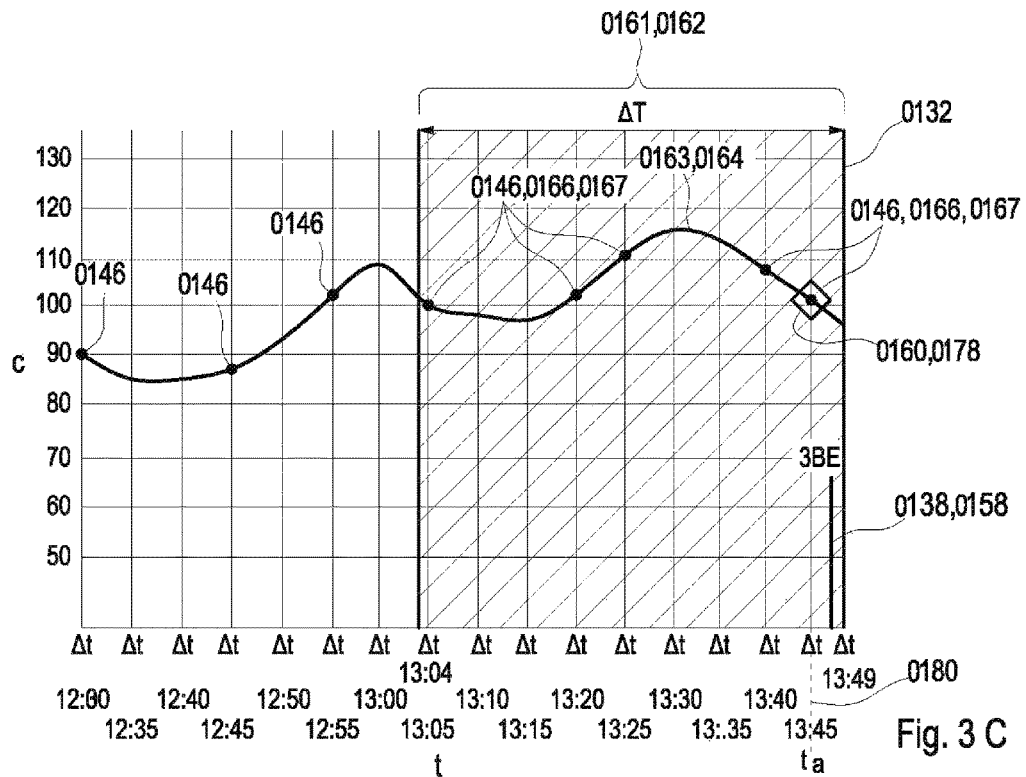
Figure 3:
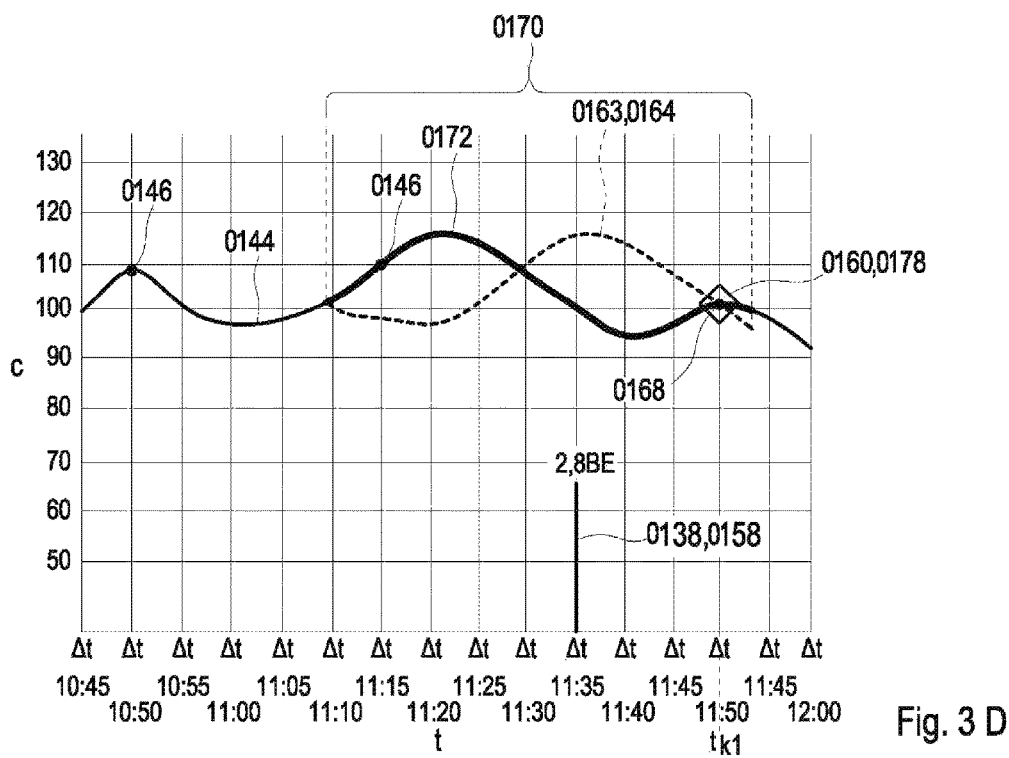
Figure 3:
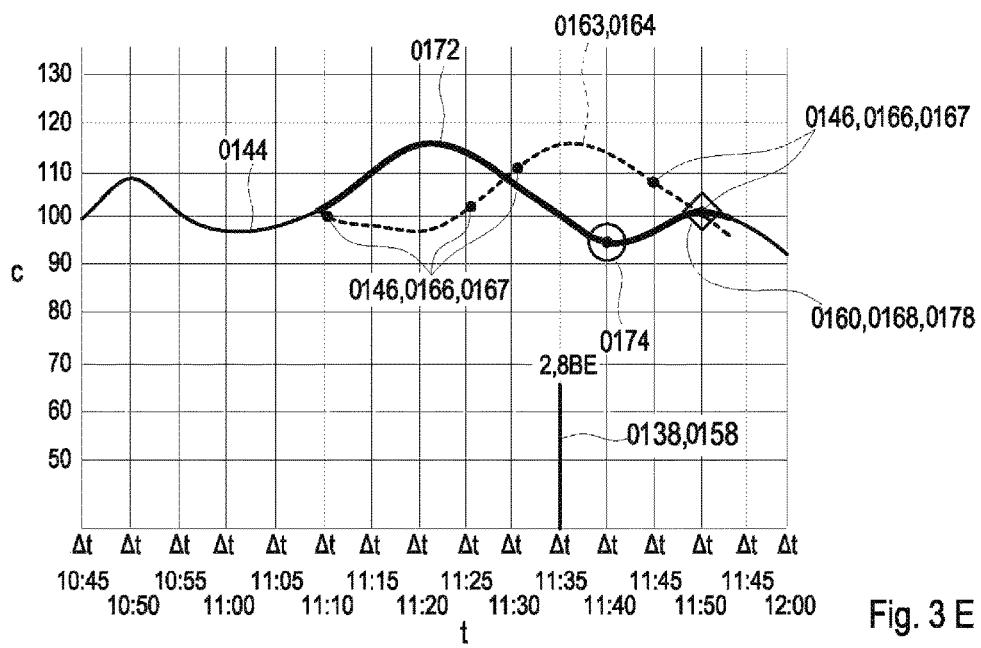
Figure 3:
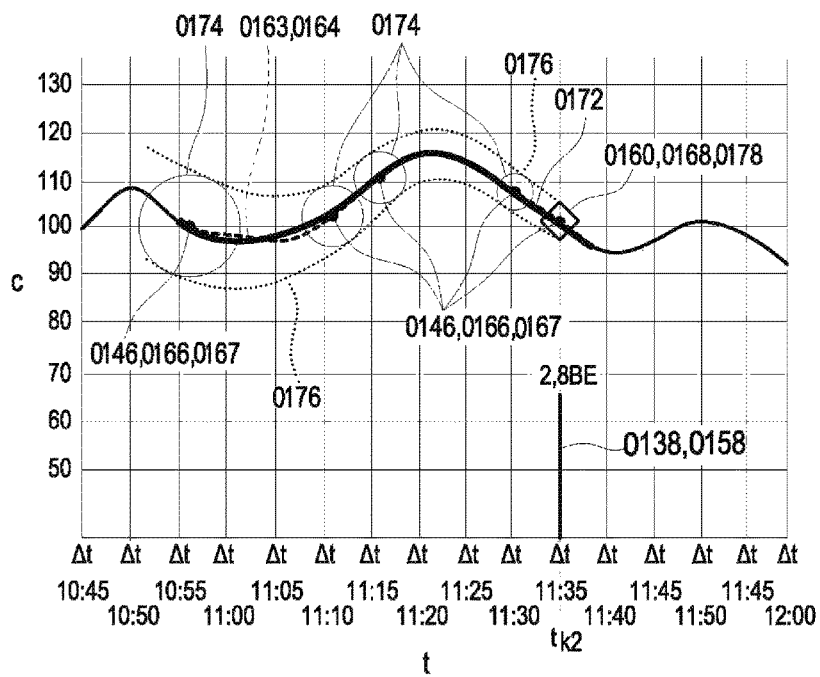
Figure 3:
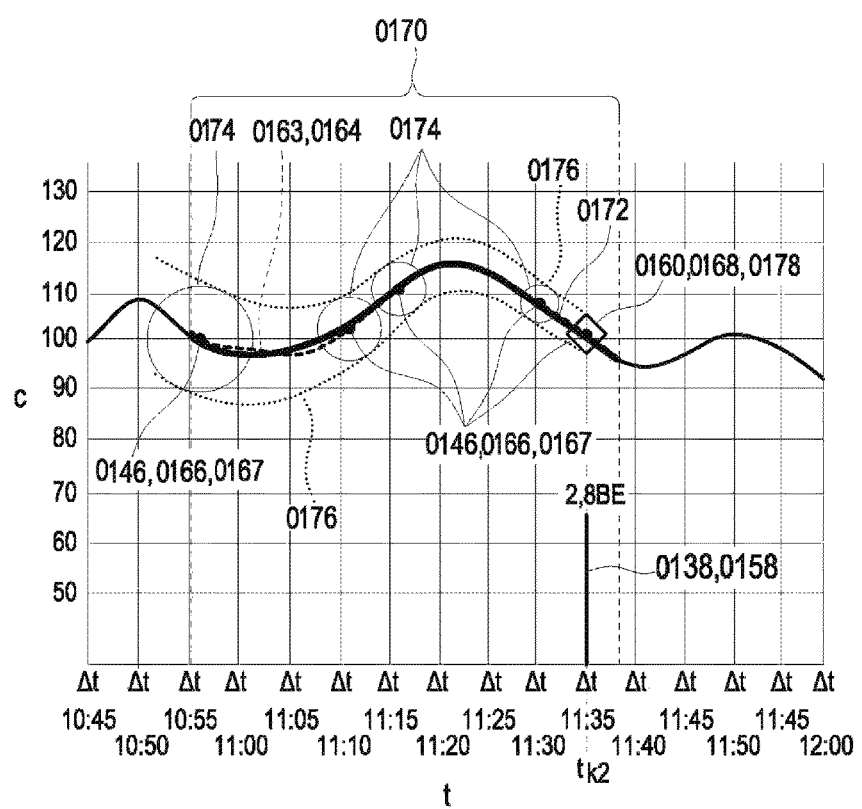

FIG. 3A shows an acquisition of measurement data, which, in an exemplary fashion, occurs up until a now-time 0132 in this example. However, in principle, other acquisitions are also possible, for example processing of purely historical measurement data within the scope of the present method. In FIG. 3A, the measurement values are plotted on the vertical axis, which measurement values in this case are the concentration c, for example in units of mg/dl, and the time t is plotted on the horizontal axis. Here, the axis origin of the time t is, for example, a time of 12:30 in FIG. 3A. The assumption is made that the measurement values, e.g. the CM data, are preferably calibrated. By way of example, the measurement values can be available with a time resolution $\Delta t$, e.g. 5 min, for the subsequent pattern selection and pattern recognition (pattern matching). The curve illustrated using a solid line in FIG. 3A and representing the measurement data record 0144 is, in this respect, not necessarily a continuous curve, but may simply be, for example, a set of measurement points, respectively with a measurement time and measurement value. However, a continuous measurement may also be carried out, or the method can also make use of, for example, interpolation curves or similar secondary measurement data records 0144, which are derived from the measurement data.

Furthermore, FIG. 3A illustrates an optional data reduction step, by means of which a reduced measurement data record 0146 can be generated from the data record shown in FIG. 3A. So-called indexing or online indexing is shown here in an exemplary fashion, in which each current measurement value is compared to a plurality of measurement value levels in a data reduction step. Preferably, indexing is carried out in real-time. In FIG. 3A, these measurement value levels are denoted by the reference sign 0142 and illustrated as horizontal lines. By way of example, these measurement value levels 0142 can in this case be prescribed in a blood glucose grid in 10 mg/dl steps. The data reduction step will be explained in more detail below in an exemplary fashion.

As explained above, measurement values are acquired at different measurement times, or else continuously, in the proposed method and stored in a measurement data record 0144. In FIGS. 3A to 3G, this measurement data record has been plotted symbolically as a curve and symbolically denoted by the reference sign 0144, wherein the concentration c, specified in mg/dl, has been respectively plotted as a function of time t. A reduced measurement data record 0146 or a portion of a reduced measurement data record 0146 can optionally be used instead of the complete measurement data record 0144 in one or more of the method steps described below. To this end, it is possible, as described above, to carry out at least one data reduction step, which should be described in an exemplary fashion on the basis of FIGS. 2 and 3A. Here use can, in principle, be made of at least one arbitrary data reduction method or data compression method, with no distinction being made between the two terms in the following text. In particular, use can be made of an online and/or real-time indexing method, in which each newly added measurement value or point of the measurement data record is, in the background, compared to correspondence with the blood glucose grid prescribed by the measurement value levels 0142 and marked in the case of correspondence, i.e. assigned to the current data record. Here, points lying on the grid prescribed by the measurement value levels 0142 are assigned to a reduced measurement data record 0146. In the process, certain, prescribed deviations from the grid can be tolerated. If the deviation from the grid is too large, no value is highlighted for this time.

By way of example, measurement data acquisition and data reduction can be brought about by means of a method illustrated in Table 1:

TABLE 1

Example of data reduction

| Measurement data record | | | | Reduced measurement data record | | |
|---|---|---|---|---|---|---|
| mg/dl | hh:mm | DD.MM.YY | | mg/dl | hh:mm | DD.MM.YY |
| 90 | 12:30 | 01.04.2010 | → | 90 | 12:30 | 01.04.2010 |
| 85 | 12:35 | 01.04.2010 | | | | |
| 85 | 12:40 | 01.04.2010 | | | | |
| 88 | 12:45 | 01.04.2010 | → | 88 | 12:45 | 01.04.2010 |
| 94 | 12:50 | 01.04.2010 | | | | |
| 102 | 12:55 | 01.04.2010 | → | 102 | 12:55 | 01.04.2010 |
| 108 | 13:00 | 01.04.2010 | | | | |
| 100 | 13:05 | 01.04.2010 | → | 100 | 13:05 | 01.04.2010 |
| 98 | 13:10 | 01.04.2010 | | | | |
| 97 | 13:15 | 01.04.2010 | | | | |

TABLE 1-continued

Example of data reduction

| Measurement data record | | | | Reduced measurement data record | | |
|---|---|---|---|---|---|---|
| mg/dl | hh:mm | DD.MM.YY | | mg/dl | hh:mm | DD.MM.YY |
| 102 | 13:20 | 01.04.2010 | → | 102 | 13:20 | 01.04.2010 |
| 111 | 13:25 | 01.04.2010 | | 111 | 13:25 | 01.04.2010 |
| 116 | 13:30 | 01.04.2010 | | | | |
| 114 | 13:35 | 01.04.2010 | | | | |
| 107 | 13:40 | 01.04.2010 | | 107 | 13:40 | 01.04.2010 |
| 101 | 13:45 | 01.04.2010 | | 101 | 13:45 | 01.04.2010 |
| 96 | 13:49 | 01.04.2010 | | | | |

In Table 1, the left partial table captioned "measurement data record" displays the complete set of measurement values, which were recorded at an interval of Δt=5 min and which are part of the measurement data record, optionally together with the assigned measurement times. The right partial table captioned "reduced measurement data record" lists the selected data of the reduced measurement data record, which was selected in accordance with the superposition with the grid of the blood glucose levels. The measurement values are respectively listed in the columns captioned mg/dl, the measurement times are listed in the columns hh:mm and the associated dates are listed in the columns DD.MM.YY.

As an alternative to this data reduction method, or in addition thereto, use can also be made of other data reduction methods. An example of a further data reduction method that can be used alternatively or additionally is described in FIG. 2. By way of example, in this data reduction method, the measurement values can once again be plotted as a function of time or, as is the case in FIG. 2 in an exemplary fashion, can be plotted as a function of an index number. A check can in each case be carried out between two adjacent measurement values of the measurement data record 0144 as to whether a measurement value level 0142 was crossed. Should this be the case, the measurement value respectively situated closer to this measurement value level can be assigned to the reduced measurement data record 0146. This is how, in the example illustrated in FIG. 2, mesh points 0148 of the measurement value level class 2 (denoted "cl2" in FIG. 2), mesh points 0150 of the class 3 (denoted "cl3" in FIG. 2), mesh points 0152 of the class 4 (denoted "cl4" in FIG. 2), and measurement values 0154 that are not assigned to the reduced measurement data record 0146 emerge.

As an alternative to the two aforementioned examples of data reduction, or in addition thereto, one or more other data reduction methods can also be used in the exemplary embodiment of the method according to the invention described below, or else in other embodiments of the method according to the invention.

In a method described in FIG. 3A, at least one pattern selection step and at least one pattern recognition step are furthermore carried out. In the following text, pattern selection step and pattern recognition step can be combined under the term "pattern matching". This pattern matching can be triggered in different ways. On the one hand, pattern matching can for example be triggered in the case of every newly added measurement value, in particular automatically, in real-time or "online". Alternatively, or in addition thereto, the pattern selection step and/or the pattern recognition step can also be triggered by certain events in this or else in other exemplary embodiments, for example by a conscious action by the user and/or by the user entering boundary conditions, for example an entry into a diary, for example an entry relating to food intake. In FIG. 3A, this is illustrated symbolically by an entry of a boundary condition 0138 in the form of a diary entry 0158 relating to food intake, for example a food intake of 3 bread units (3 BE) at a time $t_0$=13:47. In particular, examples of boundary conditions 0138, which can be accounted for in the measurement data record 0144 in the form of diary entries 0158, can include: food intake, an amount of carbohydrates, a dose of insulin or another type of medication, physical activity including a specification in respect of intensity, illness, fever, stress, menstruation, pregnancy, but also time of day, day of the week, weekend, holiday, shift work or similar boundary conditions. Combinations of different boundary conditions may also be noted.

As described above, the pattern selection step can be brought about in different ways, in particular triggered and/or carried out in different ways. In general, measurement values acquired during at least one comparison time interval are selected as comparison pattern in the pattern selection step. In the following text, the comparison time interval is, in general terms, denoted by the reference sign 0161, and the comparison pattern is denoted by the reference sign 0163 (see e.g. FIG. 3C).

As explained above, there is the possibility in this case that the comparison time interval 0161 is or comprises a current time interval 0162, wherein the comparison pattern 0163 is a current pattern 0164. This option will be explained in an exemplary fashion below, without restricting further options.

However, alternatively or additionally, the comparison time interval 0161 could for example also comprise a selectable time interval, for example a time interval that is selectable by a user, for example a time interval in a historical measurement data record, preferably a freely selectable time interval. In this case, the comparison pattern 0163 would, for example, be a pattern of interest, for example a portion from the measurement data record or the measurement values, which portion displays particular physiological characteristics or which may be of particular interest as a result of other circumstances, e.g. boundary conditions. By way of example, a user could select a region of interest in the measurement data record 0144 illustrated in FIG. 3A, for example on the display element 0126 of the hand-held instrument 0112 and/or on a monitor of a computer that has access to the measurement data record 0144. By way of example, this could be brought about by displacing and/or modifying a rectangle or a selection field with a different embodiment within a display of the measurement data record 0144, for example by means of a cursor. The measurement points, which lie within the selection field, are selected in the process, the measurement values thereof are assigned to the pattern of interest or comparison pattern 0163 and the measurement times thereof are assigned to the selectable time interval or comparison time interval 0161. A person skilled in the art in principle also knows of other options for selecting a so-called "region of interest" and these can be used within the scope of the present invention.

However, as explained above, it is merely the first-mentioned option that is shown in the following text, i.e. the option that the comparison time interval 0161 is or comprises a current time interval 0162 and that the comparison pattern 0163 is a current pattern 0164. By way of example, the pattern matching can be triggered directly at the time $t_0$, or else, for example, with a slight, e.g. prescribed, time offset, for example to the now-time 0132, for example at 13:49. As described above, the pattern matching can, as an alternative to being triggered by a diary entry, or in addition thereto, also be triggered by one or more other types of triggers, preferably in an automatic form.

This triggering of the pattern matching can, for example, firstly trigger a pattern selection step. This pattern selection step is illustrated in an exemplary fashion in FIGS. 3B and 3C. As explained above, the figures show a method variant in this case in which there is no selection by a user of a selectable time interval and/or a pattern of interest, but rather a method variant in which the comparison time interval 0161 is a current time interval 0162, and the comparison pattern 0163 is a current pattern 0164. However, in principle, other embodiments are also possible.

In particular, the pattern selection step can firstly comprise a step, illustrated in FIG. 3B, in which a start point is determined for the pattern selection, which start point is used as an anchor value 0178, acquired at an anchor time 0180, for the subsequent pattern recognitions. In the illustrated exemplary embodiment, the anchor time 0180 is a current measurement time, which is denoted by $t_a$ in FIG. 3B and at which a current measurement value 0160 is determined as anchor value 0178, which measurement value can, in particular, be selected from the reduced measurement data record 0146. Hence, in particular, the anchor value 0178 and, particularly preferably, the current measurement value 0160 can be a most recent measurement value that belongs to the reduced measurement data record 0146. By way of example, the current measurement time $t_a$ can be the time in the most recent past at which the curve of the measurement data record 0144 crossed one of the measurement value levels 0142. In the example, this current measurement value 0160 or anchor value 0178 could for example have been acquired at an anchor time 0180 or a current time $t_a$=13:45.

In a further sub-step of the pattern selection step, illustrated in FIG. 3C, measurement values, acquired during a current time interval 0162, of the measurement data record 0144 are selected as current pattern 0164. Hence the current time interval 0162 constitutes an example of a comparison time interval 0161 in this exemplary embodiment. The current time interval 0162, which can also be referred to as base time interval, can be determined in different ways. Thus, the current time interval 0162 can, in this or else in other exemplary embodiments, be defined relative to the current time $t_a$ or the anchor time 0180. Alternatively, or in addition thereto, this current time interval 0162 can also be defined as a time interval retroactive from the now-time 0132, as indicated in FIG. 3C. Thus, for example, the current time interval 0162 from the now-time 0132 can be calculated into the past by a fixed amount of time $\Delta T$. However, other options for determining the current time interval 0162 are also possible. As a further alternative, or in addition thereto, it is also possible, as described above, to select the comparison time interval 0161 in another way, for example by being embodied as time interval that is selectable by a user, for example by a user selecting a region from a measurement value curve by means of an appropriate selection element, for example a cursor.

In the illustrated example, the current time interval 0162 is illustrated as a 45 min time interval, which extends between 13:04 and 13:49. However, in practice this comparison time interval 0161 or current time interval 0162 can in general also be much longer, for example with a duration of 4 hours during the day and with a duration of e.g. 8 hours during the night. The part of the curve situated in the comparison time interval 0161, i.e. the part of the curve situated in current time interval 0162 or the measurement values thereof in the current exemplary embodiment, is defined as comparison pattern 0163, here as current pattern 0164, and hence as search pattern. In the subsequent method steps, use can be made of the comparison pattern 0163 or the current pattern 0164 and/or a reduced comparison pattern 0163 and/or a reduced current pattern 0166, which are composed of the measurement values of the reduced measurement data record 0146 comprised in the comparison pattern 0163 or current pattern 0164.

As explained above, it is also optionally possible for one or more boundary conditions 0138, particularly in the form of diary entries 0158, to be contained in the measurement data record 0144 as well, for example in the comparison pattern 0163 or the current pattern 0164. By way of example, a food intake of between 2.5 and 3.5 bread units in the last 10 min relative to the current time $t_a$ and/or to the now-time 0132, for example spaced 10 min from the right edge of the base interval, can be specified as a further boundary condition 0138.

The duration of the comparison time interval 0161, for example of the current time interval 0162, can, as explained above, be selected to be much longer in practice than the 45 min illustrated in FIG. 3C. The time duration ΔT can typically be selected as the time interval since the last meal and thus for example be 4 h during the day and e.g. 8 h at night. However, in principle, other durations of the current time interval are also possible. However, the aforementioned durations are in principle expedient for aligning a possible candidate in time. Here, additional boundary conditions can be linked to the subsequent search, for example comparable food intake, comparable physical exertion, an illness, medication or similar boundary conditions.

A pattern recognition step is carried out in the subsequent method steps, described with the aid of FIGS. 3D to 3G. Here, the anchor value 0178 is first of all displaced along the time axis in a virtual fashion. By way of example, in the illustrated exemplary embodiment, the anchor value 0178, in this case the current measurement value 0160, is displaced to the left in terms of time in a virtual fashion, and candidate values 0168 corresponding to the current measurement value 0160 are sought after. Within the scope of a coarse search, this search can firstly take place in the reduced measurement data record 0146 and/or in a measurement data record 0146 reduced in a different fashion, or else in the non-reduced measurement data record 0144.

The candidate values 0168 are preferably sought after into the past such that more recent times are considered first, and times lying further back in time are subsequently considered.

FIG. 3D shows, in an exemplary fashion, how to find a possible candidate value 0168 (in this case not necessarily the first candidate value 0168 back in time, which is adjacent to the anchor time 0180). The candidate value 0168, which was acquired at a candidate time $t_{k1}$=11:50, corresponds to the anchor value 0178 within the scope of prescribed tolerances. Starting from this possible candidate value 0168, a candidate time interval 0170 is determined, which, at the candidate time $t_{k1}$, behaves like the comparison time interval 0161 at the anchor time 0180, for example like the current time interval 0162 at the current time $t_a$. By way of example, the current pattern 0164 is, to this end, displaced, in terms of time, to earlier times such that the current time $t_a$ coincides with the candidate time $t_{k1}$, and the current pattern 0164 displaced thus is compared to a candidate pattern 0172 during the candidate time interval 0170. The displaced current pattern 0164 has been illustrated in FIG. 3D using a dashed line. The current time $t_a$ of 13:45 was in the process displaced to the candidate time $t_{k1}$=11:50, and all values of the current pattern 0164 were displaced with this value, such that the times thereof were each shifted backward by 1 h and 55 min.

Subsequently there is a comparison between the comparison pattern 0163 displaced thus, in this case the current pattern 0164, and the candidate pattern 0172. This is illustrated in FIG. 3E.

The correspondence between the candidate pattern 0172 and the comparison pattern 0163 or current pattern 0164 in the candidate time interval 0170 can be checked in different ways and can be brought about in a single stage or a number of stages. By way of example, there can firstly be a coarse comparison of the patterns 0164, 0172 in a coarse pattern identification step. To this end, use can for example be made of reduced patterns. By way of example, a check can be carried out as to whether there is point-by-point correspondence between these patterns, for example by using a reduced comparison pattern 0167 or a reduced current pattern 0166 and/or a reduced candidate pattern for a comparison. The case where a reduced comparison pattern 0167 is compared to the non-reduced candidate pattern 0172, as illustrated in FIG. 3E as well, is considered in the following text in an exemplary fashion. However, alternatively, or in addition thereto, there may also be data reduction or a reduction in the comparison steps to the extent that, for example, there is a point-by-point comparison merely at fixedly prescribed time intervals, for example at equidistant time intervals of 30 min. Here there may be a point-by-point comparison, for example starting from the candidate time $t_{k1}$, for example in the aforementioned steps with equidistant time intervals, for example 30 min. By way of example, this allows a coarse correlation to be carried out.

One or more tolerances may also be prescribed in this or else in other exemplary embodiments when comparing the comparison pattern 0163, more particularly the current pattern 0164, to the candidate pattern 0172. This is illustrated symbolically in FIG. 3E by a tolerance 0174. By way of example, it is possible to prescribe a tolerance interval about one, more or all points of the candidate pattern 0172 and/or one, more or all points of the comparison pattern 0163, in particular the current pattern 0164. By way of example, tolerances of ±5% can be prescribed, for example as illustrated in FIG. 3E using the example of the measurement value that was acquired at 11:40. The tolerances 0174 can relate to the measurement values or else to the measurement times, or even to both options, as illustrated symbolically in FIG. 3E by a circle (or, in the general case, by a preferably closed curve around the measurement point).

If a coarse correlation or a coarse pattern comparison is carried out, this can subsequently be adjoined by at least one refined pattern comparison, particularly if a correspondence is determined in the coarse pattern comparison, which refined pattern comparison for example has finer time intervals in an examination and/or uses all measurement values of the measurement data record 0144 within the candidate time interval 0170. Other methods for checking the correspondence of the patterns 0172, 0164 are also possible.

If the coarse correlation or the coarse pattern comparison yields a negative result, for example if there is a lack of correspondence within the scope of the prescribed tolerances 0174 for at least one point in the candidate time interval 0170, then the candidate time interval 0170 and the candidate value 0168 are discarded. Preferably, the at least one point in the candidate time interval is a predefined point or a predefined set of points or comprises a predefined number of points. By way of example, this is the case in FIG. 3E; this is clearly visible. In this case, it is possible to select a new candidate time and a new candidate value 0168, for example by proceeding further into the past. By way of example, the search can be into the past or else in a different search direction or with a different search profile. During the search into the past, a new candidate value 0168, which corresponds to the anchor value 0178 (in this case the current measurement value 0160), is found, in an exemplary fashion, at 11:35 as next possible candidate time tk2. Accordingly, the comparison time interval, in this case the current time interval 0162 from FIG. 3C, is displaced into the past by a value of 13:45-11:35=2 h 10 min. Subsequently, a point-by-point correspondence is once again, analogously to FIG. 3E, carried out between the new candidate pattern 0172 and the displaced current pattern 0164, for example in one step or else, once again, in a plurality of steps, for example a coarse pattern recognition step and at least one refined pattern recognition step.

A coarse pattern recognition step is firstly carried out in FIG. 3F in the form of a coarse comparison between the patterns 0164, 0172, for example once again on the basis of equidistant points of the patterns 0172, 0164, for example once again proceeding from the candidate time $t_{k2}$ into the past. By way of example, the check can once again be carried out at time intervals of 10 min. Once again, a tolerance can also be taken into account in this or else in other exemplary embodiments. Here, FIG. 3F shows that the tolerance can also be embodied in a variable fashion, for example by placing tolerance bands 0176 about the points of the comparison pattern 0163, more particularly the current pattern 0164, and/or the candidate pattern 0172, which points should be used in the coarse comparison. By way of example, these tolerance bands can take into account that measurement points further in the past have a higher measurement uncertainty, and so the tolerances 0174 can for example increase in measurement points situated further in the past. Measurement points can have a higher measurement uncertainty, regardless of their age, i.e. regardless whether they are further in the past or not. In particular, these tolerance bands can take into account that measurement points further in the past have a lower relevance, regardless of their uncertainty, and so the tolerances can for example increase in measurement points situated further in the past and a weight for the analysis of the measurement points can decrease with their relevance. Alternatively, or in addition thereto, further criteria, for example medical criteria, quality criteria, safety aspects or similar criteria, can also be included in these tolerances 0174 and/or tolerance bands 0176, which can be arranged symmetrically or else asymmetrically around the measurement values.

If, as in FIG. 3F, there is a successful coarse correlation in the coarse pattern recognition step, i.e. if the patterns 0163, or 0164, and 0172 correspond within the scope of the coarse correlation, then at least one fine correlation can optionally be carried out in a refined pattern recognition step. Here, use can for example be made of a finer pattern and/or every available data point of the current pattern 0164 can be compared to corresponding data points of the candidate pattern 0172, for example once again taking account of tolerances 0174, for example within the scope of tolerance bands 0176. This is shown in FIG. 3G. Furthermore, boundary conditions 0138 can be taken into account during this comparison, or else already during the coarse comparison, for example on the basis of rules. By way of example, if a possible corresponding candidate pattern 0172 was established during the pattern recognition step, for example during the coarse correlation and/or the refined correlation, which candidate pattern corresponds to the comparison pattern 0163, more particularly the current pattern 0164, within the scope of the tolerances 0174, there can furthermore be a check of the boundary condition or boundary conditions 0138. By way of example, it is determined in FIG. 3G that there was food intake of 2.8 bread units within a time interval of approximately 5 min from the right edge of the candidate time interval 0170. Since this boundary condition 0138 substantially corresponds to the boundary condition in FIG. 3A, correspondence in respect of the boundary conditions can also be determined between the comparison pattern 0163, or current pattern 0164, and the candidate pattern 0172. Alternatively, or in addition thereto, it is also possible to check the correspondence between the boundary conditions before or during a pattern comparison, for example by already searching for corresponding boundary conditions before or during the coarse correlation and/or by already selecting the candidate value 0168 taking account of boundary conditions.

By contrast, if the fine correlation is not satisfied, possible candidate values 0168 can continue to be sought after, analogously to the transition between FIGS. 3E and 3F, for example once again with a search direction into the past or with another search direction.

If one or more candidate patterns 0172 are identified in the measurement data record 0144, these can be utilized further in different ways. In particular, as shown in FIG. 1, these can be used to display a reference profile 0134. By way of example, this reference profile 0134 can comprise the candidate pattern 0172 that was established as corresponding, and optionally time portions before and/or after the candidate time interval 0170, and so the reference profile 0134 can for example also display a possible future development. Here, the best pattern match can be displayed and/or all pattern matches can be displayed. Furthermore, it is also possible to display a statistical analysis of all pattern matches, i.e. of all candidate patterns 0172 that were established as corresponding to the current pattern 0164. Alternatively, or in addition to this simple illustration and/or statistics, it is possible to carry out one or more additional interaction steps with the user and/or another instrument and/or medical staff trained in the art. Thus, for example, options for action can be displayed, in particular recommendations in respect of medication and/or food intake and/or physical exertion and/or the recommendation to consult a medical practitioner skilled in the art.

Figure 4:
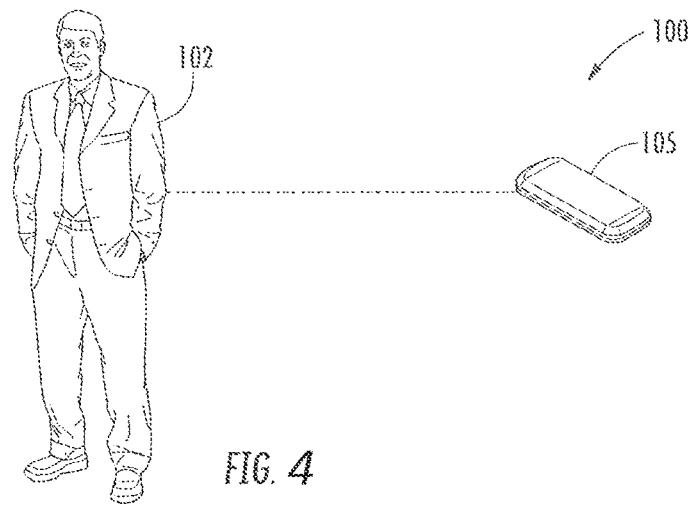
FIG. 4 depicts a diagram of an exemplary version of a patient monitoring system associated with a diabetic patient.

FIG. 4 depicts an exemplary configuration of a patient monitoring system 100 in association with a patient 102. The patient 102 may be a diabetic patient, or a patient with a physiological condition which requires routine or continuous monitoring. The monitoring system 100 comprises hardware and software components that may be utilized for implementing a pattern matching feature as described further herein. As illustrated, the monitoring system 100 comprises a device 105. Device 105 may be a handheld system with limited processing power, such as a PDA, mobile phone, glucose meter, etc. Device 105 may also be a personal computer. As further shown in FIG. 5, device 105 may comprise a physiological data input device(s) 110, a data interface 115, a processor 120, a database 130, a memory 135 along with analysis logic 132, and a display 140. These components are "operably connected" to each other, which may include one or more components connected to one or more other components, either directly or through one or more intermediate components such that they may communicate and pass information as needed to perform at least the hereinafter described processes and functions. The connection may be mechanical, electrical connection, or a connection that allows transmission of signals between the components, e.g., wired or wirelessly. The device 105 may further include an input mechanism or user interface 145 to input information and/or make data/output requests. Exemplary input mechanisms or user interfaces 145 may include a touch screen, input buttons, a keyboard, a mouse, a microphone, and combinations thereof. In one embodiment, the patient monitoring system 100 enables continuous glucose monitoring in which device 105 is operable to take multiple measurements of a concentration of glucose or a substance indicative of the concentration or presence of glucose via the physiological data input device 110, and process that dataset using the processor 120 to find similar patterns. As used herein, continuous (or continual) glucose monitor (or monitoring) may include the period in which monitoring of glucose concentration is continuously, continually, and/or intermittently (e.g., regularly or irregularly) performed.

Figure 5:
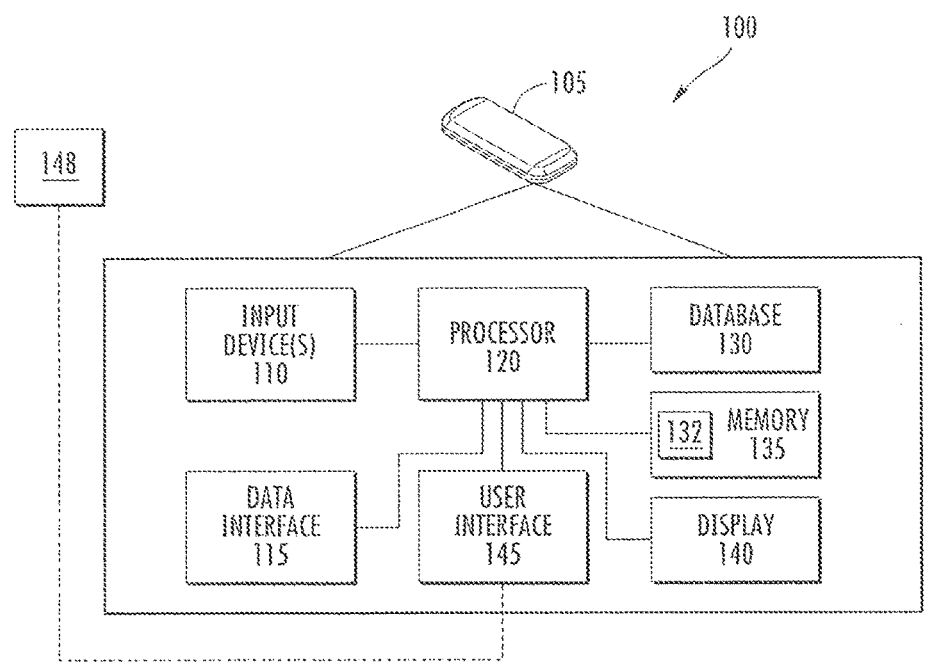
FIG. 5 depicts a block diagram of the exemplary version of the patient monitoring system of FIG. 4.

Referring to FIG. 5, the physiological data input device 110 may be, e.g., in one embodiment one or more sensors which gather automatically patient-specific physiological data such as, e.g., blood glucose, blood viscosity or other information concerning the blood chemistry of the patent 102, physical activity, temperature, heart rate, blood pressure, breathing pattern, other patient-specific physiological parameters, and combinations thereof. In one embodiment, the physiological data input device 110 can be a component or region of a patient monitoring system 100 by which glucose can be quantified and configured to produce a signal indicative of a glucose concentration of the patient 102. In operation, the physiological data input device 110 may by a glucose sensor which measures and acquires a detectable signal (e.g., a chemical signal, electrochemical signal, etc.), either directly or indirectly, from glucose or derivatives thereof that are indicative of the concentration or presence of glucose and then may transmit the signal to the processor 120 for further processing and/or storage in database 130. The physiological data input device 110 may be in communication with processor 120.

As used herein, the physiological data input device 110 may be a continuous device, for example, a subcutaneous, transdermal (e.g., transcutaneous), or intravascular device. However, it should be understood that the devices and methods described herein can be applied to any device (including external devices) capable of detecting a concentration of glucose and providing an output signal that represents the concentration of glucose. The physiological data input device 110 in another embodiment can be hardware and/or software which can analyze a plurality of intermittent biological samples, for example, blood, interstitial fluid, other desired biological fluid, etc. The physiological data input device 110 can use any method of glucose-sensing, including enzymatic, chemical, physical, electrochemical, spectrophotometric, polarimetric, calorimetric, radiometric, etc. The physiological data input device 110 may use any method, including invasive, minimally invasive, and non-invasive sensing techniques, to provide an output signal indicative of, e.g., the glucose concentration or other physiological data. The output signal can be a raw data measurement that is used to provide a useful value of glucose to a user, such as a patient or physician, who may be using the device. Smoothing, evaluation methods, etc. may be applied to the raw data measurement to provide transformed data measurements to the user.

Data measurements may be derived from the intermittent collection of data comprising measurements made by a device, such as e.g., the physiological data input device 110, (for example, a current measurement that ultimately corresponds to a glucose amount or concentration). The data measurements may be further associated with relevant data tags. By way of example only, a data tag may include when a meal was eaten, insulin was given, exercise took place, etc. Additionally, a data tag may include the amount of nutritional content in a meal, insulin, oral medication, exercise, etc. The data measurements may further comprise determining transformed data measurements from one or more raw data measurements and associating those transformed data measurements with relevant data tags.

The data measurements are obtained from a particular biological system (e.g., blood, interstitial fluid, etc.) using a device, such as e.g., the physiological data input device 110, maintained in operative contact with the biological system over a time window. The time window may be a defined period of time (e.g., hour(s), day(s), etc.) to obtain a series of data measurements (e.g., second(s), minute(s), hour(s), etc.) resulting in at least one time window dataset. The time window may be started and stopped by the diabetic patient 102 as well. By way of example only, the diabetic patient 102 may start the time window at the beginning of a meal and stop the time window at some later date after the meal. The at least one time window data set (or data measurements) may be collected from a single individual. Alternatively, the at least one time window data set (or data measurements) may be collected from multiple individuals and compiled into a database, at either the time the at least one time window data set (or data measurements) was collected or subsequently. The at least one time window data set may include raw data measurements, transformed data measurements, raw or transformed data measurements associated with data tags, or a combination thereof from the sensor.

The physiological data input device 110 may be capable of measuring only glucose in one embodiment. Alternately, in other embodiments, the physiological data input device 110 may be capable of measuring any other physiological analyte of interest that is a specific substance or component that is being detected and/or measured by chemical, physical, enzymatic, or optical analysis. The data measurements for each physiological analyte is collected and compiled into a multi-analyte database such as, e.g., database 130. In another example, the database 130 can also be formulated by compiling data measurements collected using multiple monitors, each of which measures a single substance, resulting in the multi-analyte database.

Examples of physiological analytes can include any specific substance, component, or combinations thereof that one is desirous of detecting and/or measuring in a chemical, physical, enzymatic, or optical analysis. Such physiological analytes include, but are not limited to, urate/uric acid, glucose, urea (blood urea nitrogen), lactate and/or lactic acid, hydroxybutyrate, cholesterol, triglycerides, creatine, creatinine, insulin, hematocrit, and hemoglobin), carbonate, calcium, potassium, sodium, chloride, bicarbonate, blood gases (e.g., carbon dioxide, oxygen, etc.), heavy metals (e.g., lead, copper, etc.), lipids, amino acids, enzyme substrates or products indicating a disease state or condition, other markers of disease states or conditions, etc. In the case of multi-analyte data databases, all of the physiological analytes may be related to a single physiologic state or condition; alternatively, in other embodiments, each physiological analyte may be relevant to a different physiological state or condition.

In still other embodiments, one or more of the above described physiological data/information may be entered manually by the patient 102, as well as requested for output (e.g., displayed on display 140, sent to another external device via data interface 115, etc.), via the user interface 145. In still other embodiments, the input device 110 may also include, for example, a controller, microcontroller, processor, microprocessor, etc. that is configured to receive and/or process signals, communicate with processor 120, and generate a reference pattern. The reference pattern can be the most recent data set (e.g., the most recent at least one time window data set gathered by the input device 110, a data set from the current day, hour(s), minute(s), etc. provided in memory 135 and/or database 130) and/or for any other data set of interest, e.g., historical data (previous day(s), week(s), month(s), year(s), etc.) of the patient 102. The data set can be provided from the input device 110, the database 130, the memory 135, the user interface 145, and/or from any another external source of patient data that the device 105 may communicate with via the data interface 115. It is to be appreciated that as such the reference pattern can be generated from any of the data available to the device 105, and by any method performed by the processor 120, the input device 110 (if provided with processing means), or an external device(s) operating on the data (and provided to the device via the data interface 115), in which to provide a pattern of interest, such as e.g., a glucose curve. Exemplary methods for generating a glucose curve may include: having the processor 120 draw a glucose curve using glucose data measurements provided by the physiological data input device 110, having the processor 120 draw a glucose curve using glucose data measurements read from database 130 and/or memory 135 for the at least one time window or other time periods, having the processor 120 draw a glucose curve using input received via the user interface 145, having the processor 120 select a glucose curve that represents a common behavior or condition (e.g., falling blood glucose during exercise, rise of blood glucose after a meal, etc.) that may be detected in the data of the patient 102, and combinations thereof. In other embodiments, the glucose curve need not be selected from actual glucose data measurements as discussed above in regard to historical and/or external data. The reference pattern can also be generated from data resulting from a query inputted via the user interface 145 and run by the processor 120 on recent data gathered by the input device 110 or stored data provided in database 130, memory 135 and/or in other external sources that were queried by the processor 120 via data interface 115. The reference pattern may also include any relevant data tags or multi-analyte data, and the generated and/or received reference pattern may be stored in the database 130 and/or memory 135 until needed by the processor 120 for a pattern matching process discussed hereafter in a later section.

The data interface 115 may be hardware and/or software which provides the device 105 with the ability to communicate wired and/or wirelessly with other devices and components as discussed hereafter in some embodiments, as well as to read from and write to non-transitory computer-readable products or storage medium, such as non-transitory computer-readable medium 148, in other embodiments. For the purposes of this description, a non-transitory computer readable product or storage medium can be any apparatus that can contain or store, programs and/or code for use by or in connection with processor, apparatus or devices. Examples of a non-transitory computer readable product or storage medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

Still referring to FIG. 5, the processor 120 may include any general purpose processors or any processing component configured to provide, receive and execute a sequence of instructions (such as from the memory 135). For example, processor 120 may perform calculations using at least one time window data set (or data measurements) from the physiological data input device 110 and/or the reference pattern from input device 110 (when provided with processing means), which may also be viewed as a time window data set that is generated by the input device 110. In another example, processor 120 may also compress the at least one time window data set (or data measurements) to a reduced-rank basis as will be described further herein. In another example, processor 120 may perform pattern matching with at least one time window data set (or data measurements) in a reduced-rank space as will be described further herein. Processor 120 may be implemented as a single computing device or a combination of computing devices, e.g., a combination of a digital signal processor and a microprocessor, a plurality of microprocessors, one or more microcontrollers, one or more microprocessors in conjunction with a digital signal processor core, or any other such configuration.

Still referring to FIG. 5, the display 140 may comprise a liquid crystal display ("LCD"), a touch sensitive screen, a web interface, etc. A touch screen or web interface can provide a convenient way to enter various commands and/or select various programmable options. In operation, display 140 can display information, for e.g., at least one time window data set (or data measurements), pattern match results, labeled regions to identify areas of interest, data tag information, reference patterns, etc. By way of example only, the displayed information may comprise at least one time window data set (or data measurements) that may or may not require processing by the display device prior to display. The at least one time window data set (or data measurements) displayed may be raw data, real-time data, transformed data, etc. The display 140 may comprise hardware and/or software including display instructions (e.g., software programming comprising instructions) configured to enable display of the information on display 140 and/or to obtain the information from database 130. The data in the database 130 may be queried and/or displayed by the processor 120 on the display 140.

Figure 6A:
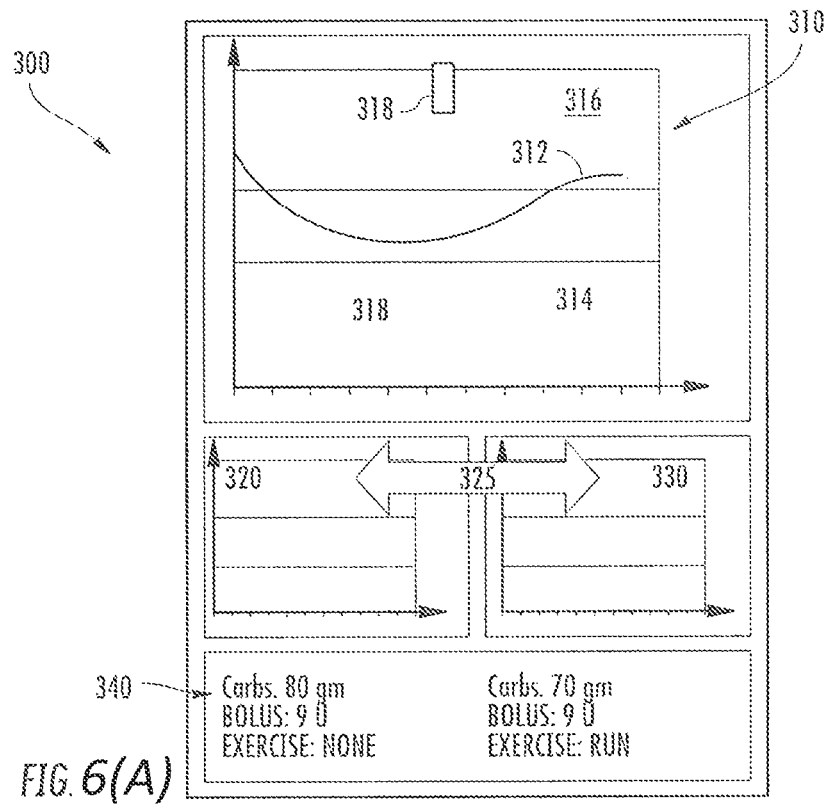
FIGS. 6(*a*)-6(*e*) depict exemplary ways of displaying various data of a pattern matching process.

Exemplary displays 140 in FIGS. 6(a)-6(e) depict various ways of displaying the different components and/or various data of a pattern-matching process. FIG. 6(a) depicts an exemplary display 300 having a reference pattern plot 310. The reference pattern plot 310 includes a plotted reference pattern 312 generated and displayed by the processor 120 from data of the patient 102 provided from the input device 110, memory 135, database 130, and/or external sources via data interface 115 as discussed previously above, which may be at least one time window data set (or data measurements) or results from a query as also discussed previously above. The reference pattern plot 310 may also include a region labeled to identify hypoglycemia 314, hyperglycemia 316, or other areas of interest. Data tags 318 may also be provided, which are shown and provide additional data relevant to the plotted reference pattern 312, for example, meal information, insulin information, exercise information, etc. Shown below reference pattern plot 310 are two pattern match plots 320, 330. Pattern match plots 320, 330 depict the closest pattern matches plotted on individual plots adjacent to reference pattern plot 310. The pattern match plots 320, 330 can be displayed by scrolling through the plots or by performing a dragging operation 325 on a touch sensitive display. The dragging operation 325 can be performed by touching the screen with a finger and then moving the finger in the desired direction on the screen. Additional data 340 can be displayed in a tabular format. The additional data 340 may be relevant to the reference pattern and match, which may include meal information, carbohydrates data, insulin dose data, exercise information, or any other data that may help in evaluating the match.

Figure 6B:
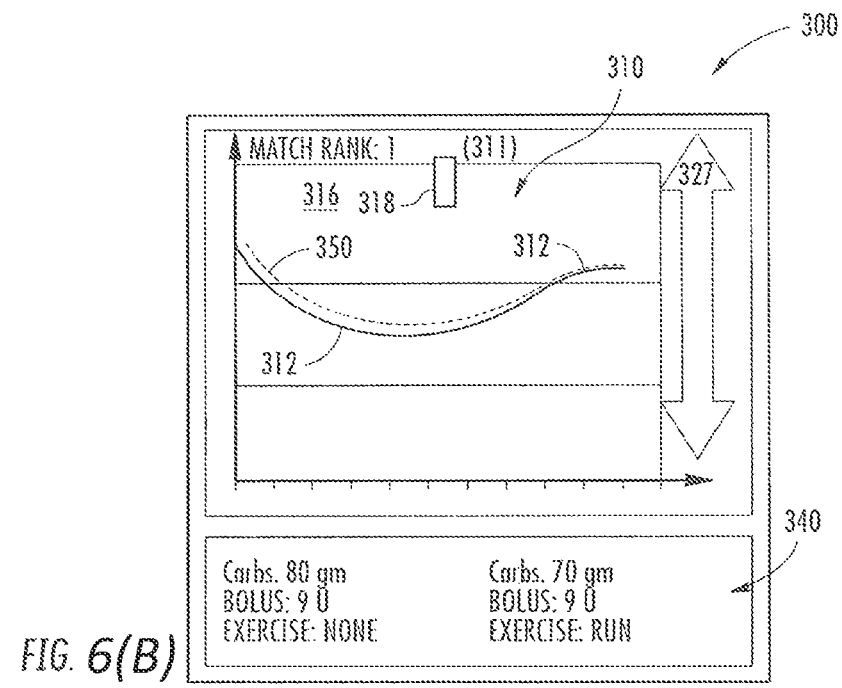

FIG. 6(b) depicts an exemplary display 300 having a reference pattern plot 310. The reference pattern plot 310 includes a plotted reference pattern 312 that may be for at least one time window data set (or data measurements) or for results of a query, and a closest pattern match plot 350 plotted on the same axis as plotted reference pattern 312. The width of the closest pattern match plot 350 and plotted reference pattern 312 are shown identical. Similar to FIG. 3(a), a hypoglycemia region 314, a hyperglycemia region 316, data tags 318 and additional data 340 are shown. Also depicted is label 311, which identifies the rank of the current match. The rank is based on how well it compares to the reference pattern 312. The next closest match plot (not pictured) can be displayed by scrolling through the plots or by performing a dragging operation 327 on a touch sensitive display. The dragging operation 327 can be performed by touching the screen with a finger and then moving the finger in the desired direction on the screen.

Figure 6C:
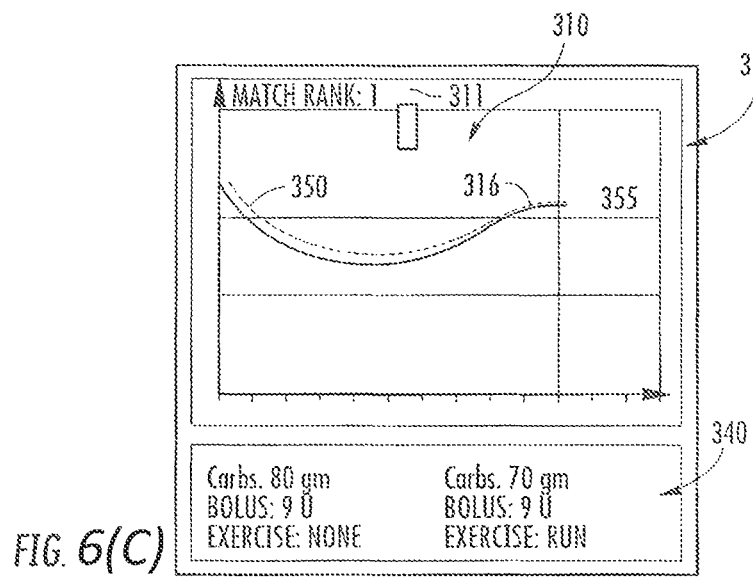

FIG. 6(c) depicts an exemplary display 300 having a reference pattern plot 310. Similar to FIG. 6(b), a hypoglycemia region 314, a hyperglycemia region 316, data tags 318 and additional data 340 are shown. As described above, the reference pattern plot 310 includes a plotted reference pattern 312 that may be for at least one time window data set (or data measurements) or for results of a query, and a closest pattern match plot 350 plotted on the same axis as the plotted reference pattern 312. The closest pattern match plot 350 may be extended to display glucose match data 355 immediately after the plotted reference pattern 312 or similarly extended to display glucose match data immediately before the plotted reference pattern 312 or both. The query can be performed as data acquisition step as mentioned further above.

Figure 6D:
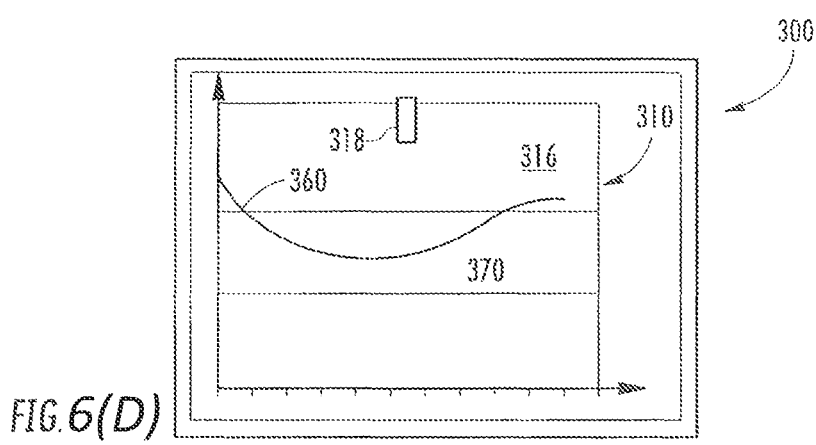

FIG. 6(d) depicts an exemplary display 300 having a raw data plot 360 and a smooth plot 370. Similar to FIG. 6(b), a hypoglycemia region 314, a hyperglycemia region 316, and data tags 318 are shown. The raw data plot 360 comprises raw, noisy data that may be at least one time window data set (or data measurements) from the sensor. The smooth plot 370 displays the compressed version of the raw data from raw data plot 360. The compressed data, which forms a smooth plot 370, may be compressed using the pattern matching or initialization algorithm described herein.

Figure 6E:
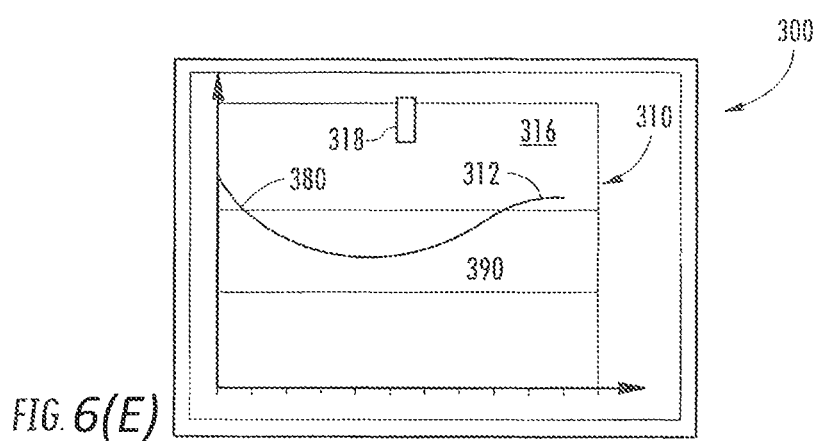

FIG. 6(e) depicts an exemplary display 300 having a reference pattern plot 310. The reference pattern plot 310 includes a plotted reference pattern 312 for data that may be for at least one time window data set (or data measurements) or for results of a query, and multiple pattern match plots 380, 390 plotted on the same axis as plotted reference pattern 312. Similar to FIG. 6(b), a hypoglycemia region 314, a hyperglycemia region 316, and data tags 318 are shown. Of course, other suitable ways in which different components of a pattern match may be depicted will be apparent to those of ordinary skill in the art in view of the teachings herein.

Referring back to FIG. 5, memory 135 may be any type of memory known in the art including, but not limited to, hard disks, magnetic tape, optical disc, semi-conductor memory, a floppy diskette, a CD-ROM, a DVD-ROM, RAM memory, a remote site accessible by any known protocol, or any other memory device for storing algorithms and/or data. In operation, memory 135 may include hardware and software for compressing sensor data to a reduced-rank basis and/or for performing pattern matches, such as e.g., via included analysis logic 132. The analysis logic 132 may be suitably configured to store, interpret and process incoming information and/or to configure the processor 120 to perform such storing, interpreting, and processing of the incoming information, which, e.g., may be the at least one time window data set, raw or transformed, etc. received from the input device 110, the user interface 145, and/or resulting from a query on available data from the input device 110, the database 130, memory 135 and/or external sources via the data interface 115. As will be discussed in greater detail below, the analysis logic 132 may include a pattern-matching algorithm for performing a pattern match of a compressed dataset to past patient data in a reduced-rank space, one or more storage algorithms, one or more data pre-processing algorithm, and/or an initialization algorithm.

Referring to FIG. 5, database 130 may comprise memory capable of receiving and storing the measured and/or detected and/or identified characteristic information, e.g., at least one time window data set, raw data measurements (e.g., numeric values which correspond to a physical measurement), compressed data measurements, transformed data measurements, and may include additional related information, e.g., data tags, pointers, etc. as described above, and/or one or more storage algorithms. When the one or more storage algorithms are executed by the processor 120, it causes the processor 120 to store at least one time window data set, raw data measurements, compressed data measurements, transformed data measurements, a single numeric result calculated or derived from one or more raw data points, etc., in database 130. The processor 120 may also be caused to read at least one time window data set, raw data measurements, compressed data measurements, transformed data measurements, etc. from database 130. The processor 120 may also be caused to index the at least one time window data set, raw data measurements, compressed data measurements, transformed data measurements, etc. from the input device 110 as a function of the time and/or date. The database 130 may collect and receive data measurements automatically via the input device 110 over the window of time, thereby generating and storing the time window data set. The data may be stored in a specialized data structure format for organizing and storing data. Exemplary data structure types may include the array, the file, the record, the table, the tree, etc. The data structure may be designed to organize data to suit a specific purpose so that it can be accessed and worked with.

As noted above, the data structure of database 130 can take on a number of different forms or be structured in a variety of ways. For example, a Kd-tree (K-dimensional tree) may be used. A Kd-tree is a space-partitioning data structure similar to a binary search tree that may be useful for the rapid search and retrieval of multidimensional data. The structure is examined in detail in J. L. Bentley, "Multidimensional divide-and-conquer," Comm. of the ACM, 23(4), (April 1980), 214-229 and J. L. Bentley, "Multidimensional Binary Search Trees Used For Associative Searching," Comm. of the ACM, 18(9), 1975, which are herein incorporated by reference.

The Kd-tree splits the data having K dimensions at each node using a hyper-plane perpendicular to one of the dimensions. Each internal node has two children, representing a partition along a given dimension of the K-dimensional hyper-plane. Data may be represented in the Kd-tree by their K-dimensional compressed vector and a time parameter that links the compressed vector to a location in the saved raw data. This structure can be used to find: the nearest neighbour to a point or reference pattern, at, the nearest d neighbours, where d is the number of neighbours of interest, at least one data point within some range r of the reference pattern, at, where r is the desired distance from the reference pattern. The data structure includes standard methods for performing both n-nearest-neighbor searches and searches for similar data within a specific range that were utilized in this algorithm.

Data may further be stored in database 130 in a queue. In operation, at least one time window data set (or data measurements) received and collected from the input device 110 may be compressed using processor 120 and added to a queue. The queue contains the most recent compressed vectors waiting to be added to the Kd-tree. The compressed vectors are moved from the queue to the kd-tree when they are older than N, where N is the length of the current time window. Thus, the compressed vectors are moved to the kd-tree when they are no longer overlapping with the current time window. The time windows are represented in the Kd-tree by their k-dimensional compressed vector, any relevant data tags, and a time parameter that links the compressed vector to a location in the saved raw sensor data.

Figure 7:
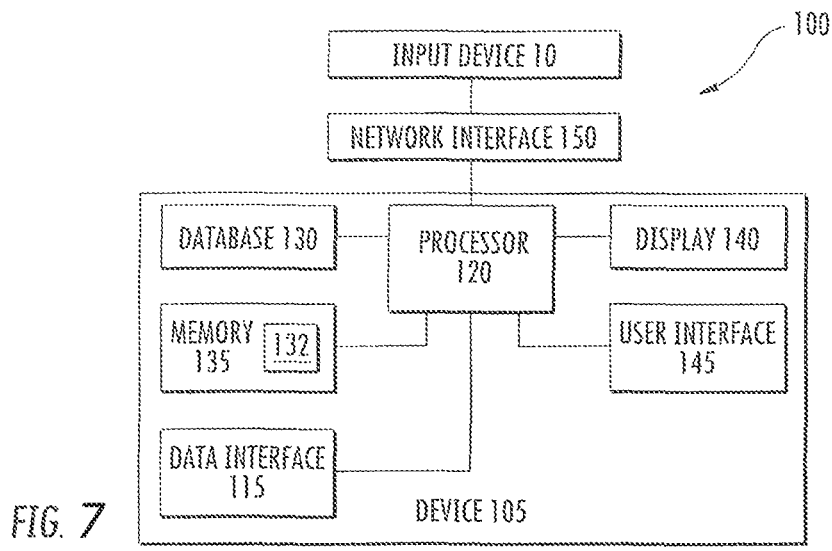
FIG. 7 depicts a block diagram of an exemplary version of a patient monitoring system.

FIG. 7 depicts another exemplary configuration of a patient monitoring system 100, and which hereafter only the difference from the configuration depicted by FIG. 5 are discussed hereafter for purposes of brevity. In this embodiment, the patient monitoring system 100 comprises device 105, input device 110 as a separate component from device 105, and a network interface 150. Device 105 comprises data interface 115, processor 120, database 130, memory 135 along with analysis logic 132, display 140, and user interface 145. The input device 110 is coupled to device 105 via the network interface 150. The network interface 150 may include a wired or wireless connection, and any wired or wireless networking hardware, such as a modem, LAN port, wireless fidelity (Wi-Fi) card, WiMax card, mobile communications hardware, and/or other hardware for communicating with other networks and/or devices. Device 105 may carry out the data storage, pattern matching and display of the results.

Figure 8:
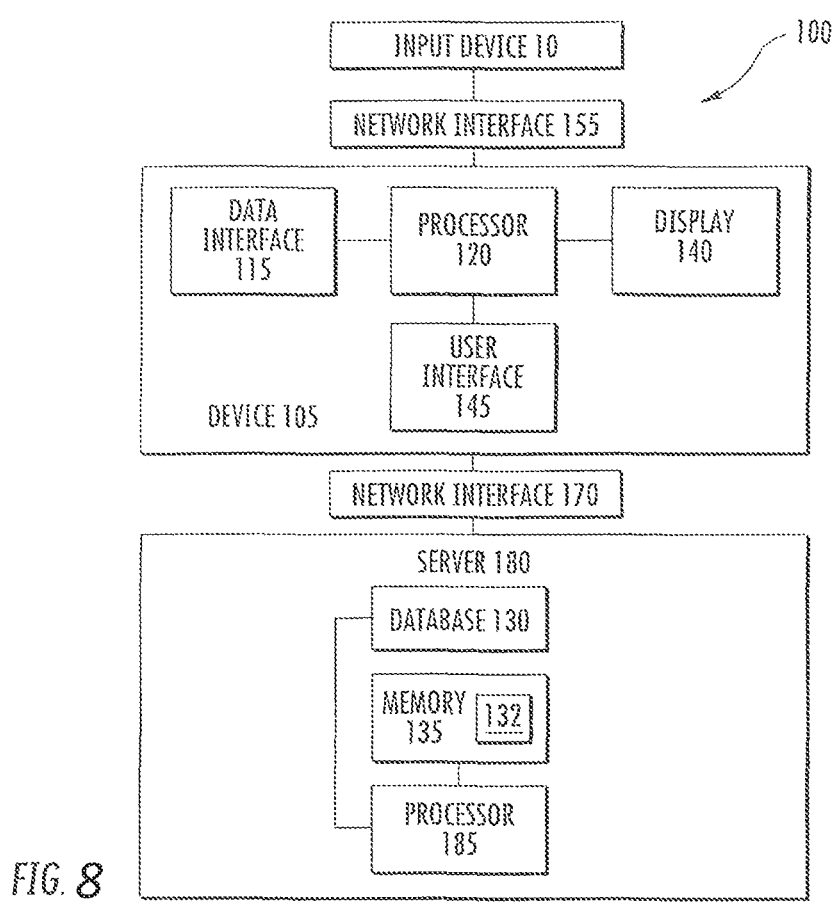
FIG. 8 depicts a block diagram of an exemplary version of a patient monitoring system.

FIG. 8 depicts another exemplary configuration of a patient monitoring system 100, and which hereafter only the difference from the configuration depicted by FIG. 7 are discussed hereafter for purposes of brevity. In this embodiment, the patient monitoring system 100 comprises device 105, the input device 110 as a separate component from device 105, a first network interface 155, a second network interface 170, and a server 180. The input device 110 may provide input to device 105 via the first network interface 155. Device 105 may be coupled to server 180 via a second network interface 170. As noted above with the network interface of FIG. 7, the first and second network interfaces may also include a wired or wireless connection, and any wired or wireless networking hardware for communicating with networks and/or devices. Device 105 comprises data interface 115, processor 120, display 140, and user interface 145. Device 105 may handle data pre-processing, inputting of data request, inputting of data queries, and display of data results. Server 180 comprises the database 130 and memory 135 along with analysis logic 132. In one example, server 180 may also comprise a processor 185 that may be configured to store data measurements into database 130 and perform pattern matching via use of the analysis logic 132.

Figure 9:
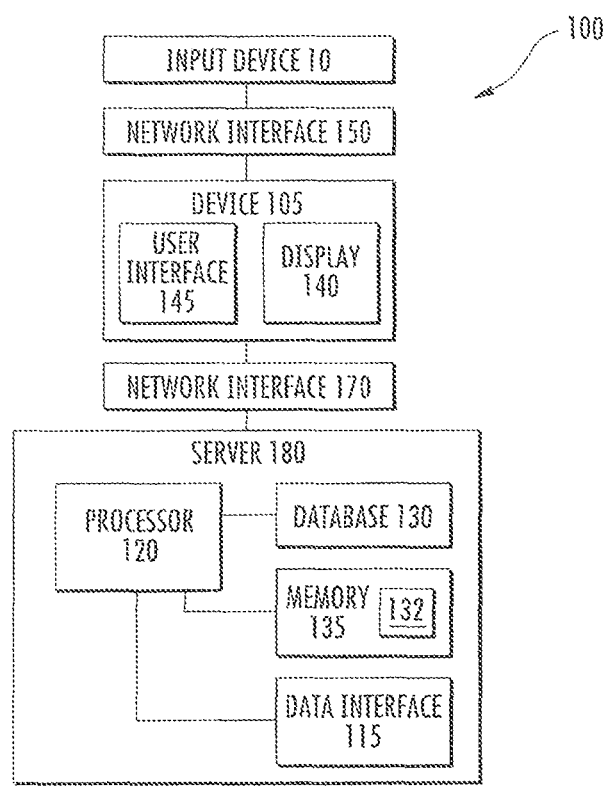
FIG. 9 depicts a block diagram of an exemplary version of a patient monitoring system.

FIG. 9 depicts another exemplary configuration of a patient monitoring system 100, and which hereafter only the difference from the configuration depicted by FIG. 8 are discussed hereafter for purposes of brevity. In this embodiment, the patient monitoring system 100 comprises device 105, input device 110 as a separate component from device 105, a first network interface 155, a second network interface 170, and a server 180. Device 105 comprises a display 140 and user interface 145, and is configured to send raw data to server 180. Server 180 comprises data interface 115, processor 120, database 130, and memory 135 along with analysis logic 132. Server 180 is configured to compress the raw data measurements, store data into database 130 and perform pattern matching.

Figure 10:
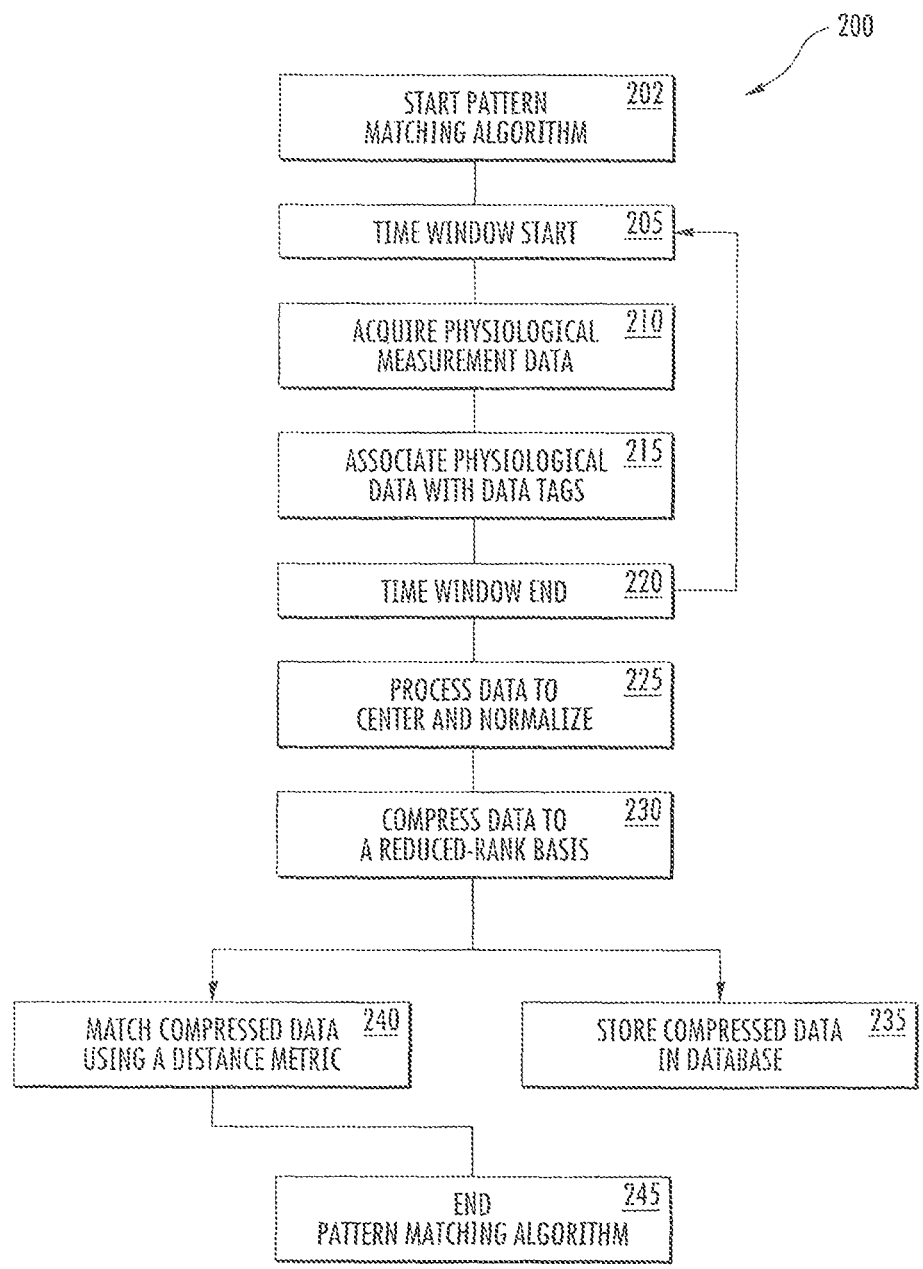
FIG. 10 depicts a flowchart of an exemplary pattern matching process using a patient monitoring system.
Figure 11:
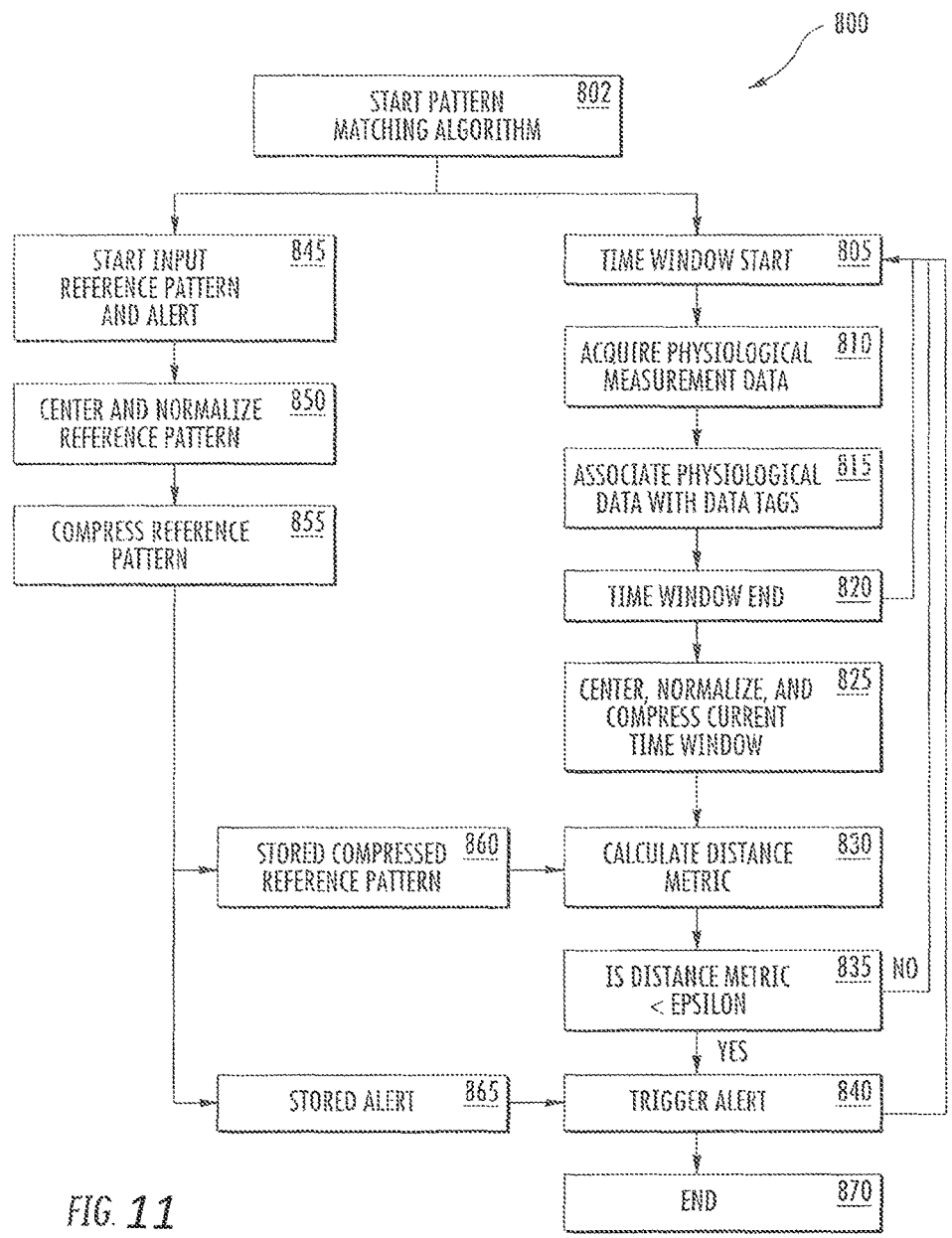
FIG. 11 depicts a flowchart of an exemplary real-time pattern matching process using a patient monitoring system.

FIGS. 10 and 11 depict flowcharts illustrating the general logic of a pattern-matching algorithm 200, 800 for efficiently finding the best match to a reference pattern. FIG. 11 depicts the general logic of a real-time pattern matching algorithm 800 for efficiently identifying a current, or most recent, time window data set that substantially matches the reference pattern. The algorithms 200, 800 are stored in a memory 135, and executed by processor 120 or 185 of the patient monitoring system 100.

Referring to FIGS. 10 and 11, blocks 202, 802 represent the start of the algorithm 200, 800. The input device 110 of a patient monitoring system 100 takes one or more glucose measurements. As noted above, other analyte and/or physiological measurements may also be taken. Blocks 205, 805 represent the start of a time window period for acquiring the one or more glucose and/or physiological measurements. The start of a time window period may be triggered by one or more of the following: user input received via the user interface 145, where the user tells the processor 120 or 185 when a new window is to begin; by a detected or scheduled event; or where a time period has elapsed and a new time period is to automatically begin.

Blocks 210, 810 represent the acquiring physiological measurement data where glucose concentration and/or other physiological data is detected by the input device 110 of the patient monitoring system 100. At least one glucose measurement, physiological measurement, or patient input, received via the user interface 145, is taken during the time window. Alternatively, a plurality of such measurements and patient input may be taken. By way of example only, measurements can be taken in increments of second, minute, hour, day, etc. Each raw data measurement is stored in database 130. Additionally, data maybe inputted by the patient 102 using the user interface 145 to answer questions displayed by the processor 120 or 185 on display 140 during the current time window period.

Blocks 215, 815 represent the association of the glucose and/or physiological measurement data with one or more data tags. As mentioned above, the data tags may include when a meal was eaten, when insulin was given, when exercise took place, the amount of nutritional content in a meal, amount of insulin, the amount and/or type of oral medication, what kind of exercise performed, etc. Of course, other data tags that can be associated with the glucose and/or physiological measurement data will be apparent to those of ordinary skill in the art in view of the teachings herein.

Blocks 220, 820 represent the end of the time window period where the processor determines whether the end has been reached. The data from the most recent time window period may be sent to a processor for further processing or alternatively may be sent to the database and held for further processing until two or more time windows of data are available. Then the two or more time windows may be further processed together. As depicted by the arrow, a new time window may be started at the end of the previous time window period, where the process for acquiring glucose and/or physiological measurement data is repeated.

Blocks 225, 825 represent the processing of data to normalize and center the data by the processor to a scale where the distribution of glucose and/or physiological measurements has a mean of zero and standard deviation of one. Blocks 230, 825 represent the compression of raw data to a reduced-rank basis performed by the processor 120. In reduced rank processing, the data may be projected on a set of basis vectors. When glucose and/or physiological measurements are correlated, a small set of basis vectors can explain most of the measurements. The input data is submitted for compression where an Eigen-decomposition is performed on the data to determine the Eigen values and Eigen vectors for the matrix $\hat{X}^T\hat{X}$. The set of K eigenvectors becomes the basis set. This set of K Eigen vectors represents the compressed equivalent of the input data. K is determined using the initialization algorithm, which is further described in FIG. 12.

As basis set, basic functions of a transformation into the frequency domain can be used. In particular, such basic functions are cosine or sine functions, wavelets or similar. Generally, lossless or lossy audio compression algorithms can be used, preferably adapted or scaled to a frequency range of the glucose and/or physiological measurements, with or without involvement of an eigen value decomposition. The compression algorithm can be a lossy compression algorithm involving a transformation into the frequency domain, wherein data reduction is provided at the transformation or within a representation of the transformed data. As a compression involving transformation into the frequency domain, an MPEG algorithm, Audio Layer III can be used. Alternatively or in combination therewith, an entropy optimization or maximization can be carried out, e.g. using a Lempel-Ziv compression method.

Figure 12:
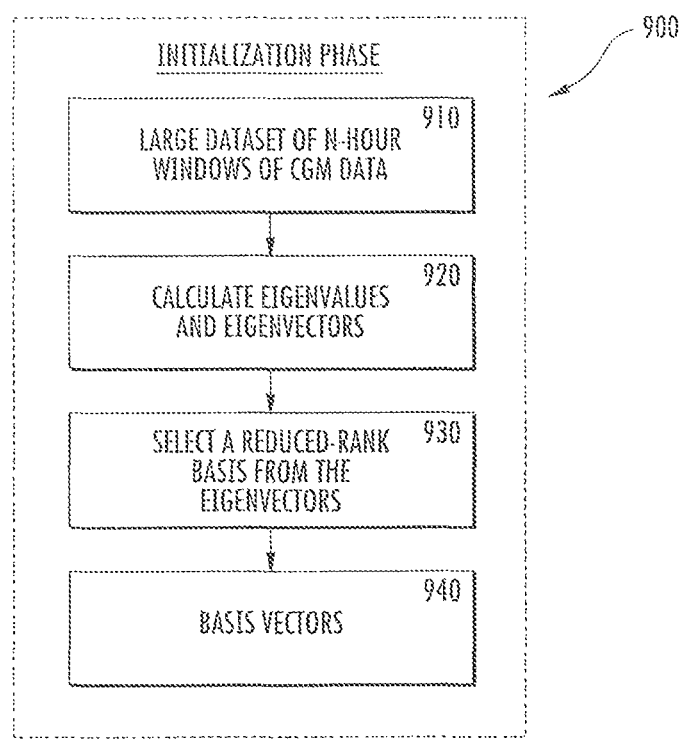
FIG. 12 depicts a flowchart of an initialization algorithm process for compressing data.

FIG. 12 depicts the initialization algorithm 900, which is the process used to find a transformation matrix to convert raw data vectors into compressed reduced-rank vectors. The initiation algorithm may occur one time to find the transformation matrix, and then the transformation matrix may be hard-coded into the pattern-matching algorithm 200, 800 running on the device 105 or system 100. Alternatively, the transformation matrix may be a separate compression algorithm from the pattern-matching algorithm 200, 800. The initiation algorithm may be run on a device separate from the device or system running the pattern-matching algorithm. By way of example only, the initiation algorithm may be run on a PC or other kind of computer. The initialization algorithm is optional and is preferably carried out in case that the method involves the use of eigen basis functions. In case that other basis functions are involved, the initialization algorithm can be skipped.

As depicted, Block 910 represents the step of collecting a large representative sample of time window data sets of a desired length, N (length of a time window data set). The time window data sets may be from a single patient or more than one patient. In particular, this applies to the measurement data record and the measurement data as mentioned further above. The data, X, may be from diabetic patients in free-living conditions and may represent a broad range of patient behaviors and results so that it may be representative of a population of diabetic patients. The data, X, may be data from a previous study or may generally come from any large source of glucose measurement data. The data, X, may be centered and normalized, $\hat{X}$, to have a mean of zero and standard deviation of one, and thus may be expressed according to Equation (1) as follows:

$$\hat{X} = \frac{(X - \bar{x})}{\sigma_x}, \tag{1}$$

where X is the M×N matrix of K time window data sets each of length N, $\bar{x}$ is the mean time window data set vector over all K time window data sets, and $\sigma_x$ is the standard deviation time window data set vector over all K time window data sets, K is the length of the compressed reduced-rank vector, and M is the number of sample time window data sets for the initialization algorithm. Data from the time window may be augmented with one or more data tags as discussed above.

Block 920 represents the step of Eigen-decomposition, where the Eigen values and Eigen vectors for the matrix $\hat{X}^T\hat{X}$ is determined, which may be expressed according to Equations (2) and (3) as follows:

$$\lambda = \text{eigenvalues}(\hat{X}^T\hat{X}) \tag{2},$$

$$V = \text{eigenvectors}(\hat{X}^T\hat{X}) \tag{3}.$$

The eigenvectors may be used as the new basis vectors with only the first K vectors, where K is the length of the compressed reduced-rank vector, being used in order to compress the data. The value of K is determined by sorting the Eigen values from largest to smallest, and then calculating the cumulative sum for the sorted list of Eigen values. The Eigen value may be used to show the amount of information explained by its corresponding Eigen vector. The Eigen vectors associated with the smallest Eigen values are removed to compress the data.

Block 930 represents the step of selecting a reduced-rank basis from the Eigen vectors. K may be selected to balance between compressing the data (for algorithm efficiency purposes) and retaining relevant information (level of detail needed in the data). Block 940 represents the step of compressing data into reduced-rank basis vectors. The first K Eigen vectors are used to create a transformation matrix, B, which converts time window data sets to the reduce-rank basis. A vector is compressed according to Equations (4)-(6) as follows:

$$B = [v1, v2, \ldots vK], \tag{4}$$

$$\bar{x}_t = \frac{(x_t - \bar{x})}{\sigma_x}, \tag{5}$$

$$a_t = B^T \bar{x}_t, \tag{6}$$

where vector at represents the reduced-rank version of $x_t$, $x_t$ is the time window data set of length N starting at time t, $B^T$ is the transformation matrix consisting of first K Eigen vectors $[v_1, v_2, \ldots v_K]$, and $v_i$ is the $i^{th}$ Eigen vector that corresponds to $\lambda_i$. The reduced rank vector at can be converted back to the original space $\tilde{x}_t$ by multiplying by B, which may be expressed according to Equation (7) as follows:

$$\tilde{x}_t = Ba_t \tag{7}.$$

Data compression may provide, and not limited thereto, the following two noted benefits: it significantly reduces the size of the data for making comparisons, and functions as a filter for removing noise from the signal. Thus, the compression algorithm may match time window data sets with a similar underlying signal rather than matching noise patterns.

Algorithm Initiation Example

Figure 13:
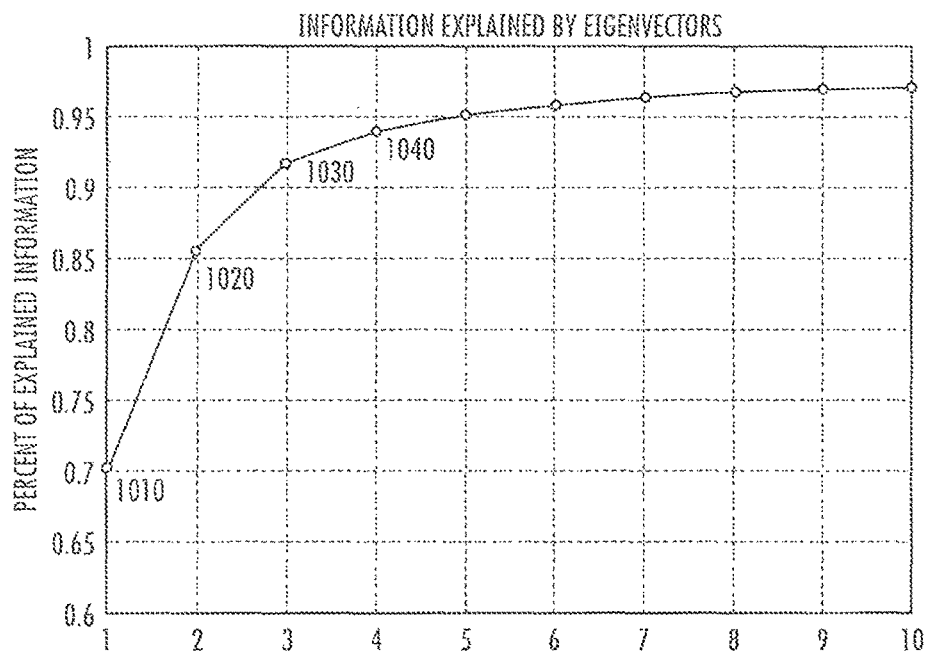
FIG. 13 depicts an exemplary cumulative sum chart of the largest Eigen values.

In some of the experiments performed, the length of each time window data set was four hours. Glucose concentration was measured each minute so each window contained a vector of 240 glucose measurement values. In other experiments performed, the length of each time window data set was two hours. Of course, other time window lengths may be used to collect glucose measurements. In step 1, where a large sample of time window data sets were collected, the length N of each time window data set was 240 minutes, as noted above, and over 100,000 time window data sets were used. The data was centered, normalized, and an Eigen decomposition was performed. The cumulative sum of the Eigen values from the Eigen decomposition was calculated. FIG. 13 depicts an exemplary plot of the cumulative sum of the largest Eigen values divided by the total sum of the Eigen values. The Eigen value may be used to show the amount of information explained by its corresponding Eigen vector. Thus, as shown in the plot on FIG. 13, compressing the time window data sets using the first Eigen vector would retain about 70% of the original data (1010). Using two Eigen vectors would retain about 85% of the original data (1020). Using three Eigen vectors would retain about 91% of the original data (1030). Using four Eigen vectors would retain about 94% of the original data (1040), and so on. In this example, K was selected to be four.

Figure 14:
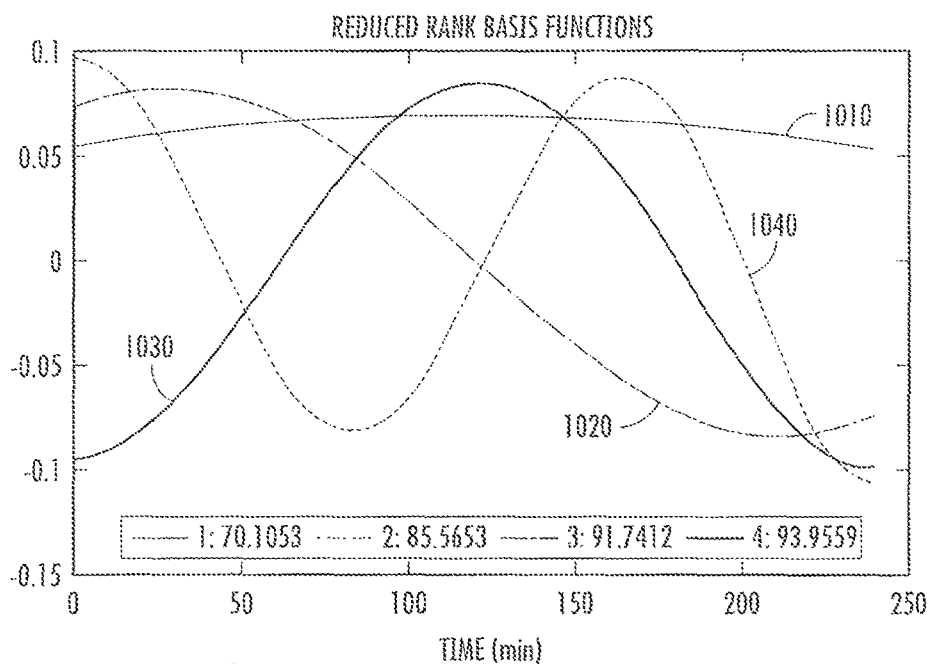
FIG. 14 depicts an exemplary plot of four Eigen vectors.

FIG. 14 depicts a plot of the first four Eigen vectors (1010, 1020, 1030, 1040) calculated using the data from this example, which shows the compressed vectors to be orthogonal. Each vector captures an important type of dynamic found in the raw data. The first Eigen vector 1010 is approximately the mean value of the raw data vector. The second Eigen vector 1020 measures the trend. The third Eigen vector 1030 captures peaks. The fourth Eigen vector 1040 responds to higher frequency components.

Figure 15:
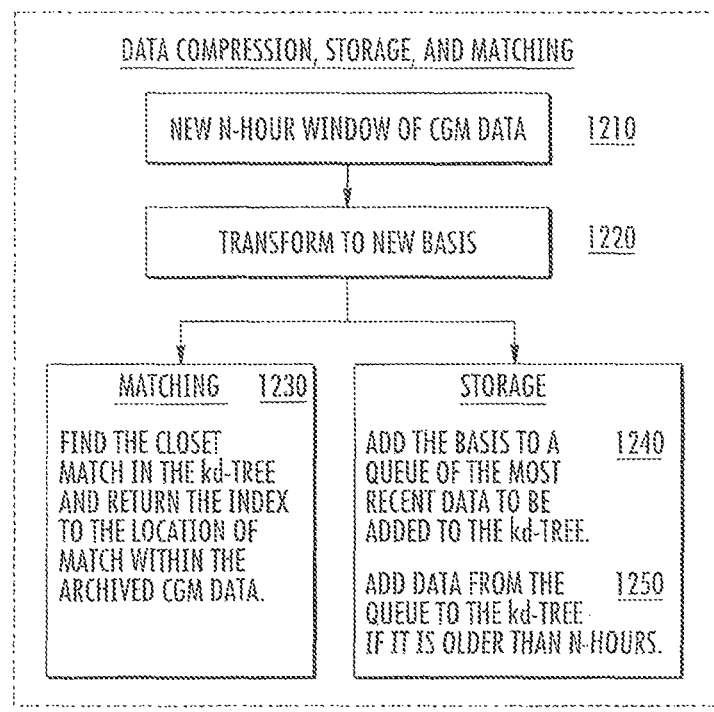
FIG. 15 depicts a flowchart of the match and storage phase of the pattern matching process of FIG. 10.

Referring back to FIG. 10, once the raw data has been compressed, the compressed data may be either pattern-matched by the processor 120 or 185, as represented by block 240, or stored in the database 130 (or alternatively, in memory 135) by the processor 120 or 185, as represented by block 235, both of which are further explained in FIG. 15. Block 245 represents the end of the algorithm.

Referring to FIG. 11, once the raw data has been compressed, the compressed data may be either pattern-matched by the processor 120 or 185, as represented by blocks 830, 835 and 840, or stored in the database 130 (or alternatively, in memory 135) by the processor 120 or 185, both of which are further explained in FIG. 15. Block 870 represents the end of the algorithm.

FIG. 11 also depicts blocks 845, 850, 855, 860, and 865, which generally represent the input and storage of a reference pattern and associated alert to be used during real-time pattern matching. Block 845 represents the input of a reference pattern and/or associated alert into input device 110 using user interface 145.

The reference pattern can be any data set of interest, e.g., historical data (previous day(s), week(s), month(s), year(s), etc.) of the patient 102. The data set can be provided from the input device 110, the database 130, the memory 135, the user interface 145, and/or from any another external source of patient data that the device 105 may communicate with via the data interface 115. It is to be appreciated that as such the reference pattern can be generated from any of the data available to the device 105, and by any method performed by the processor 120, the input device 110 (if provided with processing means), or an external device(s) operating on the data (and provided to the device via the data interface 115), in which to provide a pattern of interest, such as e.g., a glucose curve. Exemplary methods for generating a glucose curve may include: having the processor 120 draw a glucose curve using glucose data measurements provided by the physiological data input device 110, having the processor 120 draw a glucose curve using glucose data measurements read from database 130 and/or memory 135 for the at least one time window or other time periods, having the processor 120 draw a glucose curve using input received via the user interface 145, having the processor 120 select a glucose curve that represents a common behavior or condition (e.g., falling blood glucose during exercise, rise of blood glucose after a meal, etc.) that may be detected in the data of the patient 102, and combinations thereof. In other embodiments, the glucose curve need not be selected from actual glucose data measurements as discussed above in regard to historical and/or external data. The reference pattern can also be generated from data resulting from a query inputted via the user interface 145 and run by the processor 120 on stored data provided in database 130, memory 135 and/or in other external sources that were queried by the processor 120 via data interface 115. The reference pattern may also include any relevant data tags or multi-analyte data, and the generated and/or received reference pattern may be stored in the database 130 and/or memory 135 until needed by the processor 120 for a pattern matching process discussed hereafter in a later section.

The alert is customizable and can be a visual alert, such as a displayed icon or message, or light, an audible alert, such as a beep or music, or a vibrational alert, or a combination thereof. The alert can have single and/or multiple modes of notification. For example, the alert can simultaneously include an audible, visual, and vibrational notification. When an event triggers the alert notification, the user may be notified of the event or condition by feeling the vibration, hearing the audible alert, and/or seeing the visual alert. The alert may be displayed on display 140 of device 105.

In one example, the reference pattern and alert can be used to alert the patient to take specific actions whenever a particular event occurs. For example, the reference pattern can be a post-prandial event, hypoglycemic event, exercise, meals, etc. or any other problematic pattern that has occurred in the patient's past physiological data. Thus, when the event is detected again on a real-time basis, the patient monitoring system 100 will alert the patient to that fact.

Similar to block 825, block 850 represents the processing of the reference pattern to normalize and center the data by the processor to a scale where the distribution of glucose and/or physiological measurements has a mean of zero and standard deviation of one, Block 855 represents the compression of the reference pattern to a reduced-rank basis performed by the processor 120. The processor 120 or 185 may compress the reference pattern and store it for real-time comparison. Block 860 represents the storage of the compressed reference pattern and block 865 represents the storage of the alert in database 130 in a queue or in processor 120 or 185.

Block 830 represents the pattern matching steps which calculate the distance metric between the reference pattern and a real-time (or most current) time window data set. The pattern matching method is further described below in more detail. Block 835 represents the step of determining whether the distance metric is less than a certain value c which may be set by the user. If the distance metric is less than ε, then the alert is activated as shown in block 840. If the distance metric is greater than ε, then no alert is activated and the algorithm repeats the process for the next current time window data set. Block 870 represents the end of the pattern matching algorithm 800.

The pattern-matching algorithm 200, 800 may run on any suitable computing device or system, such as device 105, system 100, or provided on a non-transitory computer-readable medium that stores the pattern-matching algorithm 200, 800 in the form of a program providing instructions that when executed by a processor, such as processor 120 or 185, causes the processor to perform the above described acts of blocks 202-245 of FIG. 10 and blocks 802-870 of FIG. 11. The pattern-matching algorithm 200, 800 may be used for efficiently finding the best match or matches to a reference pattern. FIG. 15 further describes the pattern-matching (block 235 of FIG. 10 and blocks 830, 835 and 840 of FIG. 11) and storage phase of the algorithm (block 240 of FIG. 10). Prior to pattern-matching 1230, the current time window data set 1210 is centered and normalized, then transformed into the reduced-rank space 1220 using the transformation matrix, B, that was calculated previously using the initiation algorithm, and which may be expressed according to Equations (8)-(9) as follows:

$$\hat{x}_t = \frac{(x_t - \bar{x})}{\sigma_x}, \quad (8)$$

$$a_t = B^T \hat{x}_t. \quad (9)$$

The closest match or matches may be determined using a distance metric, $j_i$. In one example, the distance metric is the Euclidean distance where the difference in position of two vectors is calculated within the reduced-rank space 1220. Thus, $a_i$ is found by calculating the value that minimizes Equation (10) as follows:

$$j_i = \sqrt{(a_i - a_t)^T (a_i - a_t)} \quad (10),$$

where $a_i$ is the reduced-rank vector of a stored time window data set selected as a potential match, at is the reduced-rank reference vector, and T is the transpose function. For real-time pattern matching shown in FIG. 8, the alert is displayed if the value of the distance metric, $j_i$, is less than a threshold value, ε. The value for epsilon depends on the distance metric selected, noise penalty, length of time window, etc. In one example, s is selected to, but can be substantially close to zero. In a general case, ε may be selected using common statistical tests, for e.g., regression analysis, so that the probability that the matches are measurements of the same physiological data is at least 0.95 or in a more stringent case 0.98.

$$j_i \leq \varepsilon \quad (11).$$

In another example, the distance metric is the Mahalanobis distance, which also takes into account the correlations of the data set.

$$j_i = \sqrt{(a_i - a_t)^T \Sigma^{-1} (a_i - a_t)} \quad (12),$$

where $\Sigma^{-1}$ is the inverse of the covariance matrix. Of course, other distance metrics may be used to perform pattern matching and will be apparent to those of ordinary skill in the art in view of the teachings herein.

A modified Euclidean distance metric may be used, where the Euclidean distance is modified with an error penalty function to penalize raw data that is too distorted. In one example, the distortion over a raw data window may be estimated by calculating the sum of the absolute error between the compressed data and its raw data, which may be expressed according to Equation (13) as follows:

$$e_i = \Sigma |g_i - \tilde{g}_i|, \text{ where } \tilde{g}_i = B^{a_i} \quad (13),$$

where $e_i$ is the sum of the absolute error, $g_i$ is the absolute error of the raw data, and $\tilde{g}_i$ is the absolute error of the compressed data that may be determined to find the closest match or matches that are both close and have less distortion. The closest match or matches may be determined using the Euclidean distance within the reduced-rank space, for example, by calculating the value that minimizes Equation (14) as follows:

$$j_i = \sqrt{(a_i - a_t)^T (a_i - a_t)} + \mu e_i \quad (14),$$

where μ is a parameter used to tune the balance between minimizing the distance and error. This distance metric will tend to find patterns that are both similar and with lower distortion. The value of $j_i$ can be used to evaluate the quality of the match. For example, if $j_i$ is less than some threshold then the match could be qualitatively described as "excellent," "good," or "poor." The distance metric may include components representing the difference between tags associated with the data.

$$e_{tag} = f(k_i, k_t) \quad (15).$$

In operation, when the pattern-matching algorithm 200 is executed by a processor, e.g., processor 120 or 185, it can cause the processor to further perform the pattern match by determine the distance metric between the nearest neighbour and the reference pattern. In another example, when the pattern-matching algorithm 200 is executed by the processor 120 or 185, it can cause the processor to further perform the pattern match by determine the distance metric between the nearest d neighbours and the reference pattern. In another example, when the pattern match algorithm is executed by a processor, e.g., processor 120 or 185, it can cause the processor to further perform the pattern match by determine the distance metric between at least one data point within some range r of the reference pattern, where r is the desired distance from the reference pattern. Pattern-matching algorithm 800, when executed by a processor 120 or 185, it can cause the processor to pattern-match using the most recent or current time window data set and the reference pattern. When the most recent or current time window data set matches the reference pattern, the device 105 triggers an alert, which can include the display of an alert message containing therapy information.

The pattern-matching algorithm 200, 800 may be run on, for example, a continuous glucose monitor system or other patient monitoring systems as described above. The pattern-matching algorithm 200, 800 may also be run on other exemplary continuous glucose monitors manufactured by, for example, Medtronic®, DexCom®, and Abbott Diabetes Care® or any other system that may be used to display and/or analyze raw data from a physiological sensor, and/or reference patterns from actual or generated data, for patterns.

In one example, a patient monitoring system runs a pattern matching algorithm. The patient monitoring system comprises an input device which receives a biological sample and acquires a plurality of physiological measurements of a patient within a time window thereby generating at least one time window data set, a memory storing a pattern matching algorithm, a database to store the at least one time window data set, and a processor in communication with said input device to receive said generated at least one time window data set and in communication with the memory in order to execute the pattern matching algorithm. When the pattern matching algorithm is executed by the processor, it causes the processor to compress the at least one time window data set into a reduced-rank space and perform a pattern match between a reference pattern and the stored at least one time window data set using a distance metric. The memory may further store a data pre-processing algorithm. The data pre-processing program, when executed by said processor, may cause said processor to normalize and center the at least one time window data set to a scale where the distribution of the plurality of physiological measurements has a mean of zero and a standard deviation of one.

The generated at least one time window data set may be compressed into a reduced-rank space using a transformation matrix. The transformation matrix may be determined by an initialization algorithm, which when executed by the processor, causes the processor to perform an Eigen-decomposition on a large, representative physiological measurement dataset to determine $\lambda$ eigenvalues and V eigenvectors, calculate the cumulative sum of the eigenvalues, and select a subset K of the largest Eigen vectors. By way of example only, K can be six or less. In another example, K can be five or less. In another example, K can be four or less. By way of example only, K may also be preselected to retain up to about 90% of the original data from the at least one time window data set. In another example, K may be preselected to retain up to about 95% of the original data from the at least one time window data set. In another example, K may be preselected to retain up to about 98% of the original data from the at least one time window data set.

When the pattern matching algorithm is executed by said processor, it may cause the processor to pattern match by determining the distance metric within the reduced-rank space. It may also cause the processor to pattern match by determining the closest match that calculates the value that minimizes the distance metric within the reduced-rank space. The pattern matching algorithm, when executed by said processor, may further cause the processor to determine the absolute error of a pattern match using the distance metric within the reduced-rank space or of the closest match that minimizes the distance metric within the reduced-rank space. The processor may perform the pattern match using a Kd-tree search or a naïve exhaustive search.

The patient monitoring system may further comprise a database and one or more storage algorithms. When the one or more storage algorithms are executed by said processor, it may cause the processor to store a compressed dataset in a Kd-tree structure in the database. It may also cause the processor to add the compressed dataset to a queue, and then add the compressed dataset from the queue to the Kd-tree structure. By way of example only, data sets may be stored in the database at a regular interval, based on an event, based on a data tag, based on the pattern of the data, or when requested by the user.

In another example, a patient monitoring comprising a sensor and a processor may use the pattern-matching algorithm for processing at least one time window data set. In operation, the patient monitoring automatically receives via the sensor a biological sample into the patient monitoring, acquires a plurality of physiological measurements automatically generates at least one time window data set, and automatically has the processor process the generated at least one time window data set to normalize and center the at least one time window data set to a scale where the distribution of physiological measurements has a mean of zero and a standard deviation of one, compress the normalized at least one time window data set into a reduced-rank space, and perform a pattern match between a reference pattern and the compressed at least one time window data set using a distance metric within a reduced-rank space.

During the pattern match, the processor may automatically find the closest match by calculating the smallest distance metric value between the reference pattern and one of the stored at least one time window data set (i.e., potential match) to find the closest match within the reduced-rank space. This may be done by performing a Kd-tree search or by performing a naïve exhaustive search. The processor may also automatically finds the absolute error of the pattern match or closest match.

The processor may automatically compress the generated or normalized dataset into a reduced-rank space by performing an eigen-decomposition via decomposing an $X^TX$ matrix into $\lambda$ eigenvalues and V eigenvectors. Then the processor may automatically calculate the cumulative sum of the eigenvalues, determine the corresponding eigenvector for each eigenvector, and select a subset of eigenvectors by balancing between data compression and preservation of relevant information. the may occur by automatically applying an orthogonal transform matrix to said subset of eigenvectors to provide a compressed reduced-rank vector. The processor may also automatically store the compressed dataset in a Kd-tree.

In another example, a non-transitory computer-readable medium may store the pattern matching algorithm in the form of a program. When the program is executed by a processor, it causes the processor to perform at least a pattern match of a reference pattern to a stored data time window data set collected via a patient monitoring system using a distance metric. The program may cause the processor to perform the pattern match by finding the nearest neighbour to the reference pattern. In another example, the program causes the processor to perform the pattern match by finding the nearest d neighbours, where d is the number of neighbours of interest. In a further example, the program causes the processor to perform the pattern match by finding at least one data point within some range r of the reference pattern, where r is the desired distance from the reference pattern. The program may cause the processor to further perform the pattern match by determine the absolute error between the nearest neighbour and the reference pattern, between the nearest d neighbours and the reference pattern, and/or between the at least one data point within some range r of the reference pattern, where r is the desired distance from the reference pattern.

As noted above, when running a pattern matching algorithm, the reference pattern can be the most recent at least one time window data set (except for where a real-time pattern matching algorithm is running) and/or can be any other pattern of interest, e.g., a diabetes patient's past data, another source of glucose data, a generated glucose curve, etc. Exemplary methods for generating a glucose curve may include: drawing a glucose curve using, for example, a mouse, a keyboard, a touch screen, etc., selecting a glucose curve that represents a common behavior or condition (e.g., falling blood glucose during exercise, rise of blood glucose after a meal, etc.), etc. The glucose curve need not be selected from actual glucose data measurements, but can be selected from actual glucose measurement data. The reference pattern may also include relevant data tags.

The pattern matching algorithm can be used in a variety of ways. For example, pattern matching can be performed to identify problematic meals. At times, diabetic patients are face with the challenge of controlling post-prandial (i.e., after a meal) hyperglycemic excursions. Diabetic patients can monitor their post-prandial glucose behavior by glucose testing at a distinct time after a prandial event. This, however, may neglect the dynamics of the glucose excursion, that is, the change in glucose or other relevant data (e.g., carbohydrate intake, other meal information, insulin levels, etc.) after a meal. The pattern matching algorithm may be used by a diabetic patient or health care provider to draw quickly a reference pattern of the hyperglycemic post-prandial event that corresponds to the dynamics of the meals a patient has consumed. Finding patterns in the patient system that are similar to the reference pattern may allow for identification of problematic meal events. A health care provider or diabetic patient may correct these events in the future by more accurately estimating the carbohydrate content or modifying treatment appropriately. The pattern matching algorithm may also be used to identify multiple instances where hyperglycemia was most severe and determine patterns that may have caused these deviations. The pattern matching may be used to identify similar meals. A search of past data may be made for similar glucose patterns and/or behavioral patterns to assist a diabetic patient to recollect past decisions and outcomes. In operation, a user may draw or select a pattern, and the system calculates the percentage of time that a diabetic patient's closest match data is similar to the reference pattern within certain boundaries.

In another example, pattern matching can be performed to identify hypoglycemic events. Diabetic patients are also sometimes faced with undetected nocturnal hypoglycemic episodes. Undetected hypoglycemic episodes are possible on account of both meal-influenced glucose-insulin dynamics and physical activity. A reference pattern may be used by a user to identify periods where the patient experienced hypoglycemia to analyze these episodes to provide a framework for identifying hypoglycemia causes and providing solutions. For example, the combination of closest match patterns and meal, insulin, and physical activity information may serve as a useful tool in analyzing patient hypoglycemic behavior. It may also indicate strategies to avoid hypoglycemia. In operation, a user may draw or select a pattern, and the system calculates the percentage of time that the diabetic patient's closest match data is similar to the reference pattern within certain boundaries.

In another example, pattern matching can be performed to estimate proactively bolus or meal intake. A reference pattern and meal information may be used by a user to search through a meal database and observe past glycemic behavior. The user may then analyze post-prandial behavior based on the past event, and make insulin bolus changes to avoid a post-prandial hyperglycemic excursion. Similarly, a user can use past physical activity, insulin and meal information to correct for impending hypoglycemic episodes before exercising or other physical activity.

In another example, pattern matching may be used in a real-time patient monitoring system (running the real-time pattern matching algorithm) to notify a patient if a most recent or current time window data set is substantially similar to a reference pattern. The reference pattern is input into the device along with an alert that will display when the monitoring system identifies a most recent or current time window data set that is substantially similar to the reference pattern. When the most recent or current time window data set matches the reference pattern, an alert will be triggered. The reference pattern can be any problematic pattern in the patient's physiological data (e.g., post-prandial behavior, hypoglycemic events, hyperglycemic events, exercise, etc.)

Referring to FIG. 15, during the storage phase, data that is available and compressed may be added to a queue 1240. The queue contains the most recent compressed vectors waiting to be added to the kd-tree. The compressed vectors are moved from the queue to the kd-tree when they are older than N, where N is the length of the current time window 1250. Thus, the compressed vectors are moved to the kd-tree when they are no longer overlapping with the current time window. The time windows are represented in the kd-tree by their k-dimensional compressed vector and a time parameter that links the compressed vector to a location in the saved raw data.

Pattern Match Examples

Exemplary pattern match results were generated by finding the closest match in a database containing 138,489 stored four-hour data windows compressed into 4-dimensional vectors. For each time window, the closest match was found in the reduced-rank space. The searches were performed using a naïve exhaustive search and the efficient kd-tree search. Details of the exemplary pattern match results will be discussed in more detail below using FIGS. 16(a) and 16(b), 17(a) and 17(b), 18(a)-18(c), 19(a)-19(e) and 20.

Figure 16A:
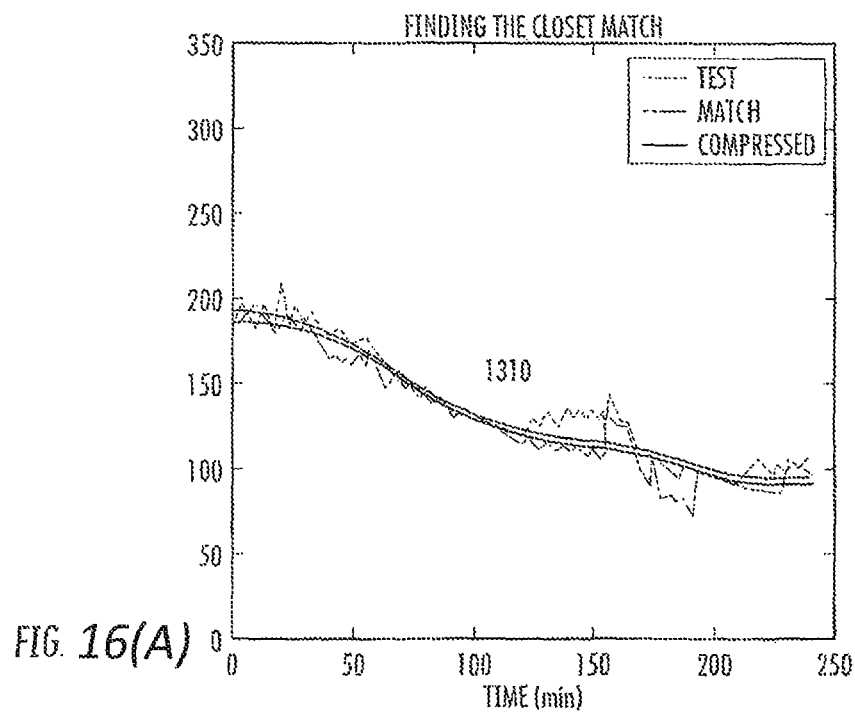
FIGS. 16(a) and 16(b) depict exemplary pattern match plots having a downward trend.
Figure 16B:
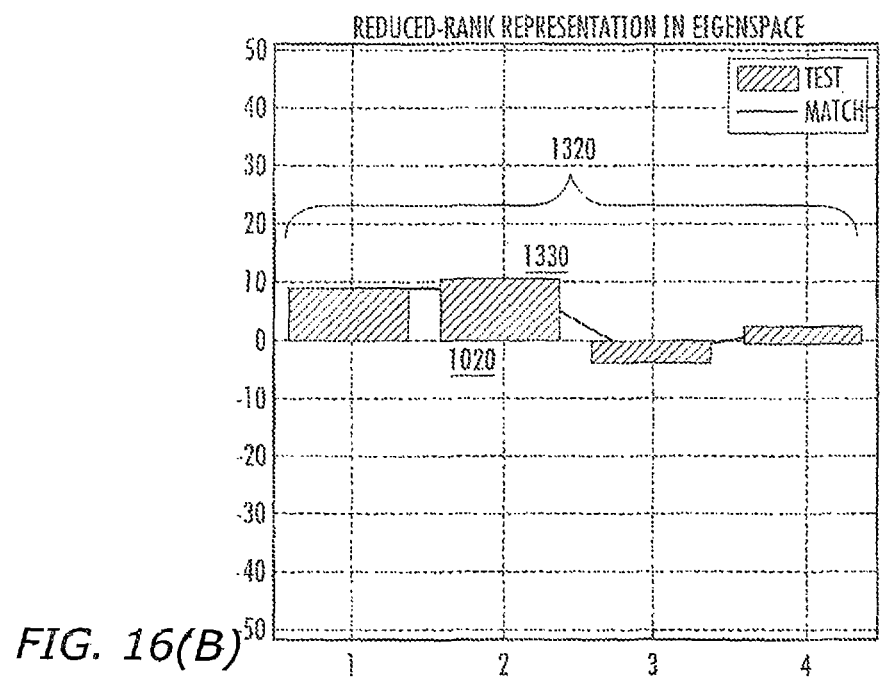
Figure 17A:
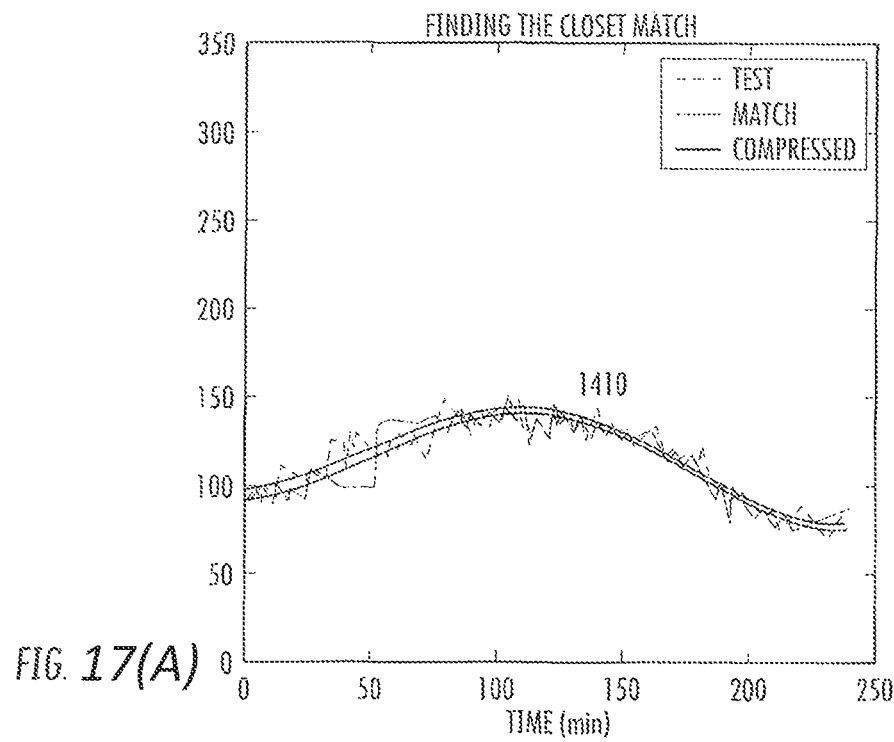
FIGS. 17(a) and 17(b) depict exemplary pattern match plots having a peak.
Figure 17B:
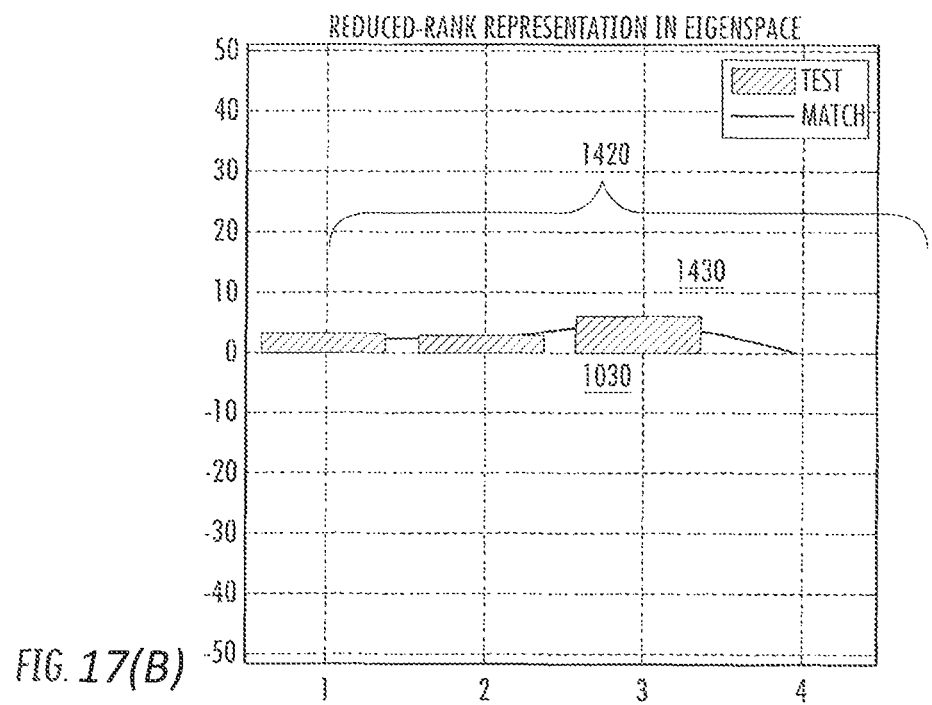

FIGS. 16(a), 16(b), 17(a) and 17(b) depict two results from an exemplary pattern-match search for the closest match. FIGS. 16(a) and 17(a) show exemplary plots (1310, 1410) of the time window raw data used for the pattern-match search, its compressed version, and the raw data of a match along with its compressed version. FIGS. 16(b) and 17(b) show exemplary plots of the value of the compressed vectors with the time window data plotted as bars (1330, 1430) and the match as a line (1320, 1420). The exemplary plots of FIGS. 16(a) and 16(b) show a downward trend so the second Eigen vector 1020 contains the strongest response. The exemplary plots of FIGS. 17 (a) and 17(b) show a peak so the third Eigen vector 1030 contains the strongest response. The ability to interpret the values in the reduced-rank space could be used for other algorithms, such as hypoglycemia prediction, meal pattern classification, and noise-filtering.

Figure 18A:
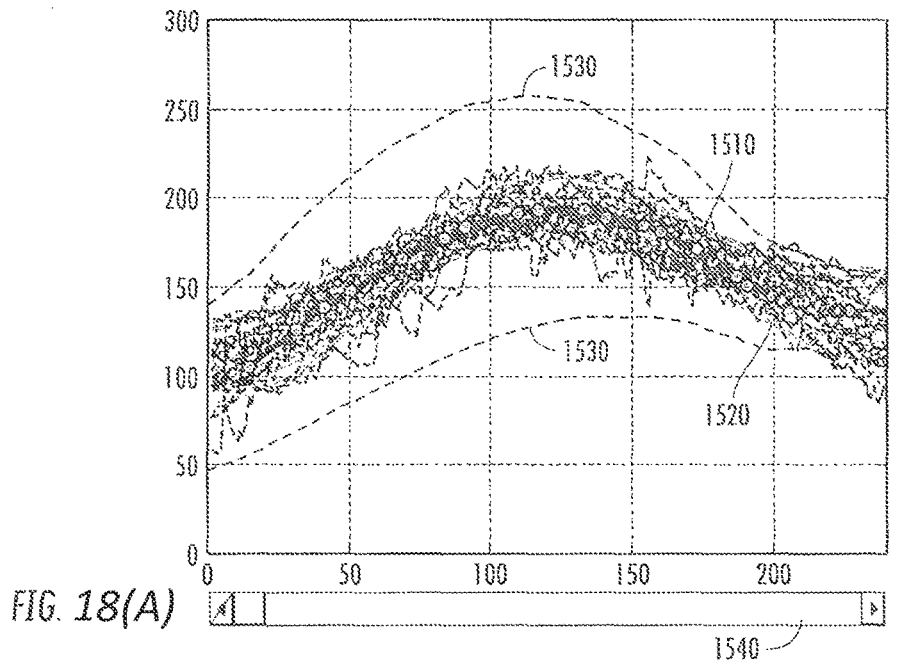
FIGS. 18(a)-18(c) depict exemplary displays of pattern match plots over a 4 hour time period.
Figure 18B:
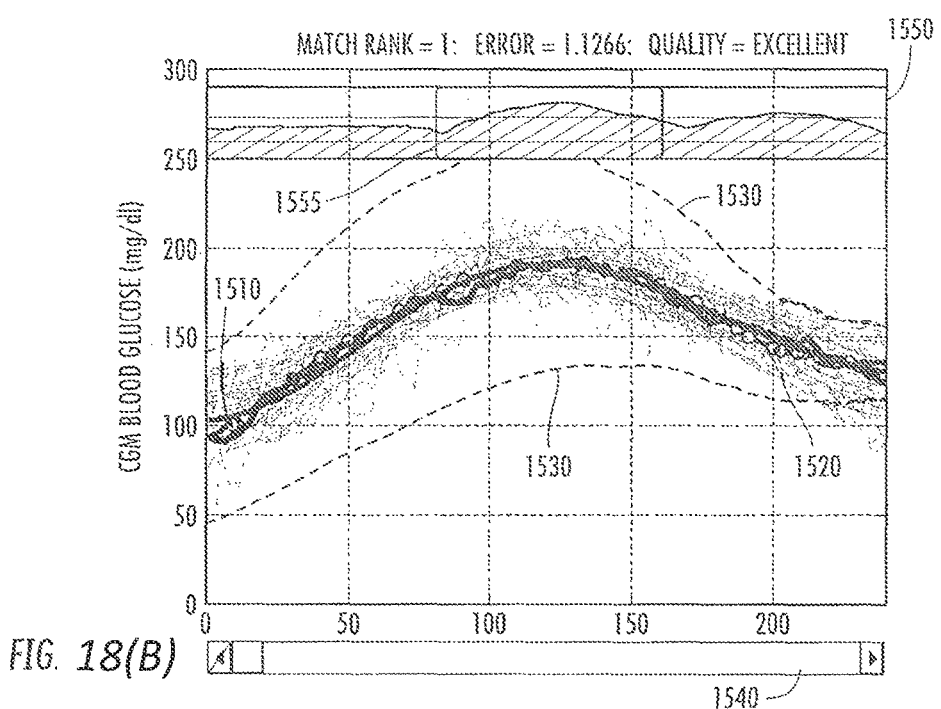
Figure 18C:
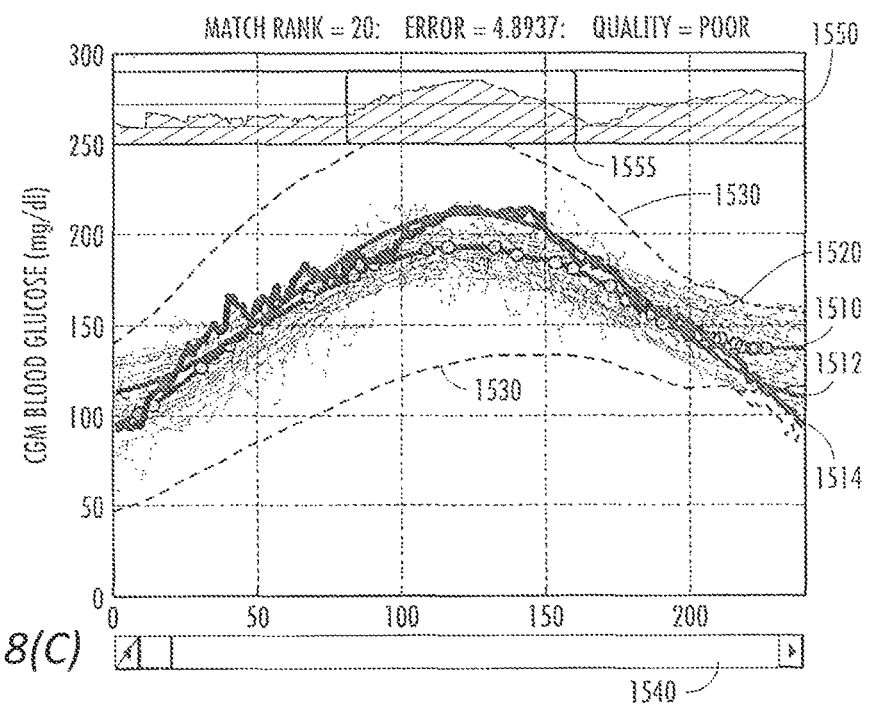

FIG. 18(a) depicts an exemplary display of a reference pattern plot of blood glucose concentration over time. In this example, a four hour reference pattern 1510 (shown as a line with circle points) was drawn and the pattern matching algorithm returned the reduced rank vectors of the top 20 matches 1520 shown as smooth lines. The noisy lines are the top 20 matches shown as raw data vectors. The top 20 matches 1520 were determined using Euclidean distance in the reduced-rank space and the sum of absolute error between the potential match's raw data vector and its reduced-rank vector. As depicted, the plot contains the reference pattern 1510 and all 20 matches 1520. Alternatively, the plot may contain the reference pattern and one or more matches. The plot may also contain error boundaries 1530 that range from about +/−15% to +/−50%. The error boundaries 1530 may be useful for showing a visual comparison. Also, shown is a scroll bar 1540 at the bottom of the screen that may be used to scroll through and/or select a specific match. The scroll bar 1540 may be a touch sensitive display, whereby the scroll bar on the screen is touched with a finger and then moving the finger in a desired direction on the screen. The arrows to the left and right of scroll bar 1540 may be touched with a finger on the screen to scroll through and/or select a specific match. In addition, a mouse may also be used to scroll through using scroll bar 1540 or the left and right arrows. As a specific match is selected, the display changes to highlight the specific match. Matches that are not selected may be dimmed and placed in the background.

FIG. 18(*b*) depicts an exemplary display of a reference pattern plot of blood glucose concentration over time. Similar to FIG. 18(*a*), the plot contains the four hour reference pattern 1510 (shown as a line with circle points), reduced rank vectors of all 20 matches 1520 (shown as smooth lines), raw data vectors of all 20 matches (shown as noisy lines), error boundaries 1530 and scroll bar 1540. Also depicted are two highlighted lines showing the reduced rank vector of a particular match and the corresponding raw data vector (which is the noisy highlighted line) for the match. The display also includes a match rank, which ranks the matches in order from closest to Nth closest match, where N is the number of matches. In this particular example, the match rank can range from 1 to 20. FIG. 18(*b*) shows a match rank of 1 indicating that the highlighted match is the closest match to the reference pattern. The other matches are dimmed and placed in the background. Also depicted is a match error, which shows the absolute error between the match and the reference pattern. The quality assessment label is also depicted and is based on the match error numbers. A quality assessment label may comprise excellent, good, fair, poor, bad, awful, etc. or other label may be used to indicate the quality of a match. The display includes a timeline 1550 at the top of the graph, which depicts the matched section 1555 placed in a timeline that may provide context of the match.

FIG. 18(*c*) depicts another exemplary display of a reference pattern plot of blood glucose concentration over time. Similar to FIGS. 18(*a*) and 18(*b*), the plot contains the four hour reference pattern 1510 (shown as a line with circle points), reduced rank vectors of all 20 matches 1520 (shown as smooth lines), raw data vectors of all 20 matches (shown as noisy lines), error boundaries 1530 and scroll bar 1540. Also depicted are two highlighted lines showing the reduced rank vector of a particular match 1512 and the corresponding raw data vector 1514 (which is the noisy highlighted line) for the match. FIG. 18(*c*) depicts a match rank of 20 indicating that the highlighted match is the 20th closest match to the reference pattern. The other matches are dimmed and placed in the background. Also depicted is the match error and quality assessment label. The display in this example shows a high match error and therefore, the quality assessment label is poor. The display also depicts a timeline 1550 at the top of the graph showing the matched section 1555.

FIG. 19(*a*) depicts an exemplary display of a reference pattern plot of blood glucose concentration over time and includes matching with a meal time tag. In this example, matches 1620 were determined for the two hours of data just prior to a meal in order to assist the user to evaluate possible outcomes for a meal based on past behaviors. Shown in FIG. 19(*a*) is the carbohydrates value for the meal. By way of example only, pattern matching may be done using a reference pattern 1610, a meal time tag and/or a carbohydrate value 1630. The display may include a timeline 1640 at the top of the reference pattern plot, which depicts the 2 hour matched section 1645 placed in a timeline with data shown on either side of matched section 1645 that may provide context of the match. In this example, the actual outcome of the meal may be seen. Reference pattern 1610 was drawn and the pattern matching algorithm returned the top matches 1620. As depicted, the plot contains the reference pattern 1610 and the 7th best match 1620. Of course, the plot may contain the reference pattern and one or more matches. Also, shown is a scroll bar 1650 at the bottom of the screen that may be used to scroll through and/or select a specific match. The scroll bar 1650 may be a touch sensitive display, whereby the scroll bar on the screen is touched with a finger and then moving the finger in a desired direction on the screen. The arrows to the left and right of scroll bar 1650 may be touched with a finger on the screen to scroll through and/or select a specific match. In addition, a mouse may also be used to scroll through using scroll bar 1650 or the left and right arrows. Quality of a match may be evaluated using error metrics (e.g., the absolute error between the match and the reference pattern), and a quality assessment label, for e.g., excellent, good, fair, poor, bad, awful, etc. or any other label that may be used to indicate the quality of a match.

FIG. 19(*b*) depicts an exemplary display of a reference pattern plot of blood glucose concentration over time and includes matching with a meal time tag. In this example, the reference pattern 1610 is drawn to find instances of when a user may have been going into hypoglycemia and/or took carbohydrates to correct for the hypoglycemia. The display may be used to evaluate a patient's ability to correctly recover from hypoglycemia without overshooting into hyperglycemia. Matches 1620 were determined for two hours of data. The carbohydrates value (not shown) for the meal can be plotted. By way of example only, pattern matching may be done using a reference pattern 1610, meal time tag and/or a carbohydrate value 1630. The display may include a timeline 1640 at the top of the reference pattern plot, which depicts the 2 hour matched section 1645 placed in a timeline with data shown on either side of matched section 1645 that may provide context of the match 1620. In this example, the actual outcome of the meal may be seen. Reference pattern 1610 was drawn and the pattern matching algorithm returned the top matches. As depicted, the plot contains the reference pattern 1610 and the best match 1620. Of course, the plot may contain the reference pattern 1610 and one or more matches 1620. Also, shown is a scroll bar 1650 at the bottom of the screen that may be used to scroll through and/or select a specific match 1620. The display also includes a match rank, which ranks the matches in order from closest to Nth closest match, where N is the number of matches. In this particular example, FIG. 19(*b*) shows a match rank of 1 indicating that the highlighted match is the closest match to the reference pattern. Quality of a match may be evaluated using error metrics (e.g., the absolute error between the match and the reference pattern), and a quality assessment label, for e.g., excellent, good, fair, poor, bad, awful, etc. or any other label that may be used to indicate the quality of a match.

FIG. 19(*c*) depicts an exemplary display of a reference pattern plot of blood glucose concentration over time and includes matching with a sleep time tag. In this example, the reference pattern 1610 is selected for the two hour period prior to a subject going to sleep. The display may be used to evaluate the likelihood of nocturnal hypoglycemia based on the current state of the patient and their historical data. Matches 1620 were determined for two hours of data. The carbohydrates value (not shown) can be plotted. By way of example only, pattern matching may be done using a reference pattern 1610, sleep time tag and/or a carbohydrate value 1630. The display may include a timeline 1640 at the top of the reference pattern plot, which depicts the 2 hour matched section 1645 placed in a timeline with data shown on either side of matched section 1645 that may provide context of the match 1620. Reference pattern 1610 was selected and the pattern matching algorithm returned the top matches. As depicted, the plot contains the reference pattern 1610 and a match 1620. Of course, the plot may contain the reference pattern 1610 and one or more matches 1620. Also, shown is a scroll bar 1650 at the bottom of the screen that may be used to scroll through and/or select a specific match 1620. The display also includes a match rank, which ranks the matches in order from closest to Nth closest match, where N is the number of matches. In this particular example, FIG. 19(b) shows a match rank of 3 indicating that the highlighted match is the third closest match to the reference pattern. Quality of a match may be evaluated using error metrics (e.g., the absolute error between the match and the reference pattern), and a quality assessment label, for e.g., excellent, good, fair, poor, bad, awful, etc. or any other label that may be used to indicate the quality of a match.

Figure 19A:
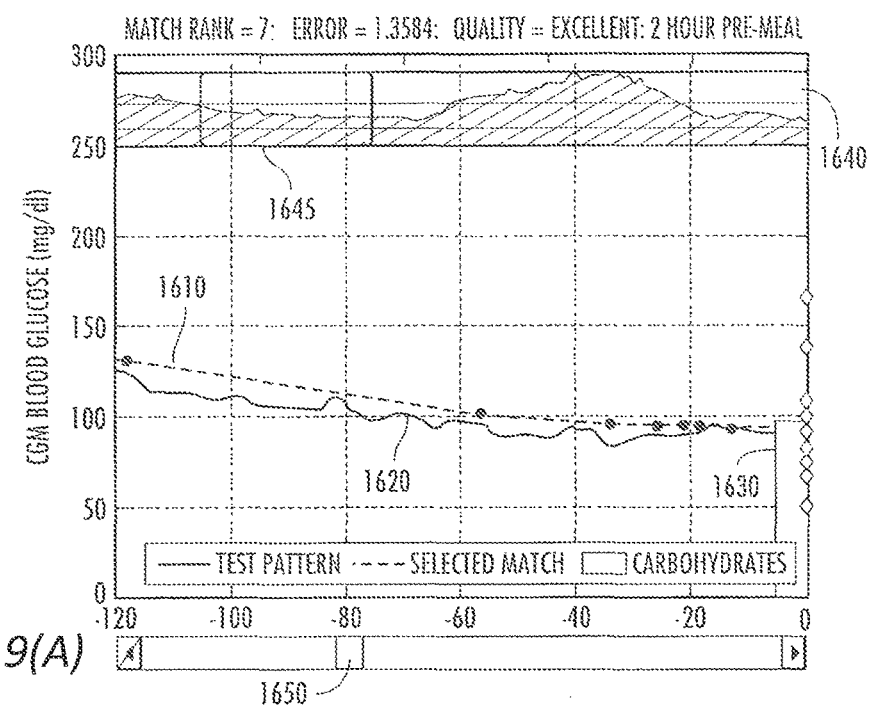
FIGS. 19(a)-19(e) depict exemplary displays of pattern match plots over a 2 hour time period.
Figure 19B:
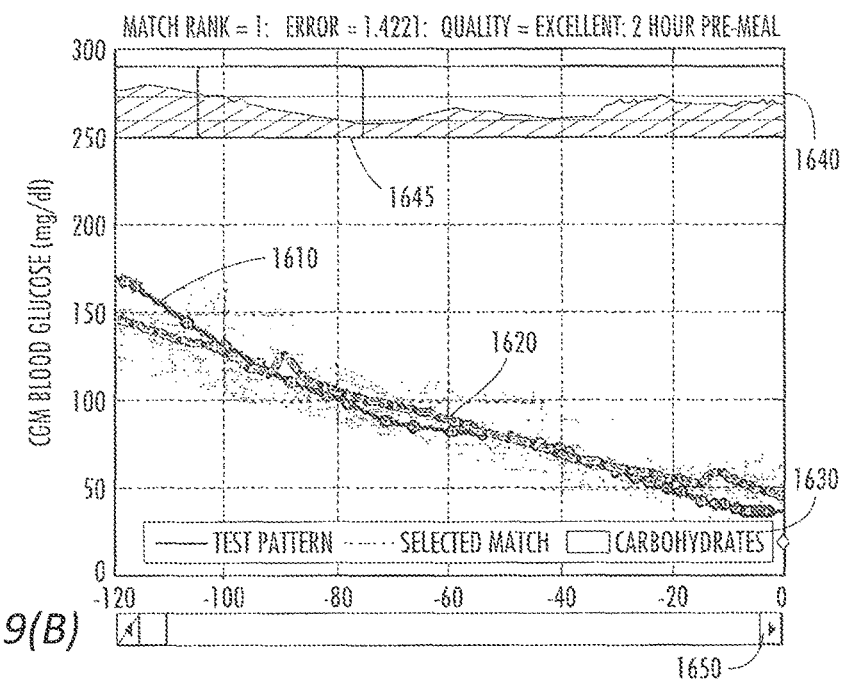
Figure 19C:
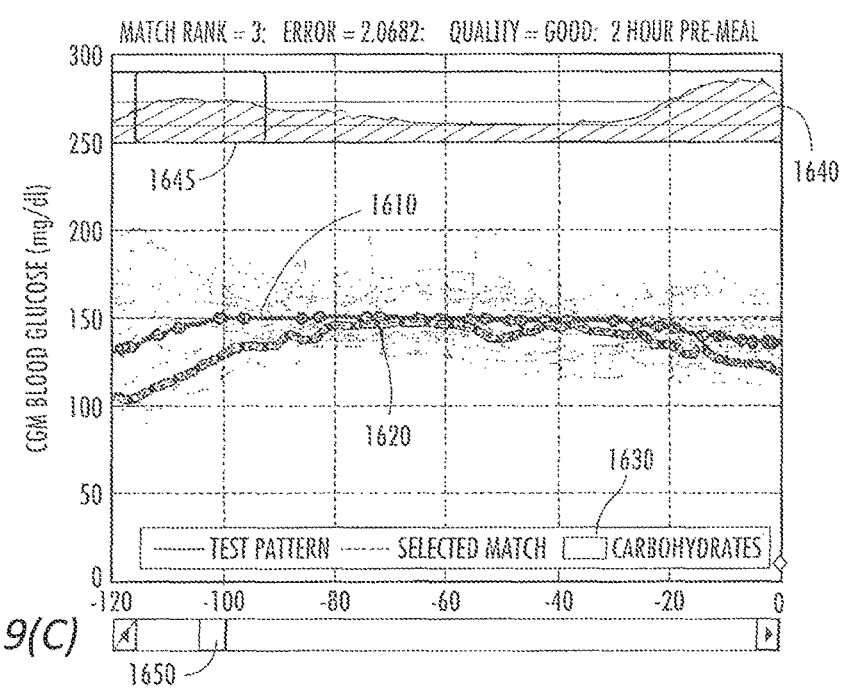
Figure 19D:
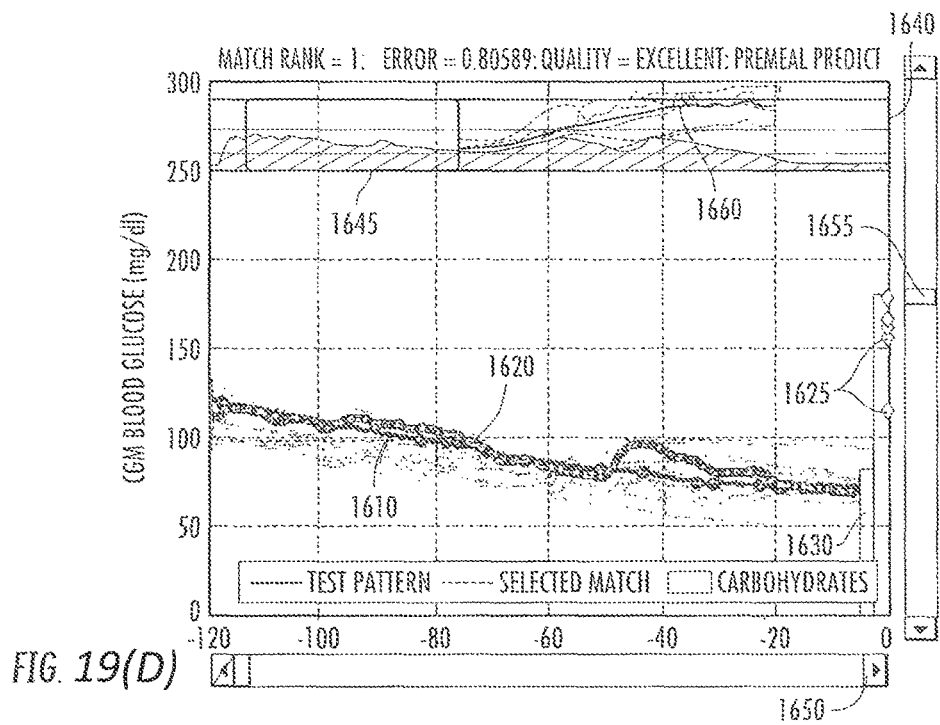
Figure 19E:
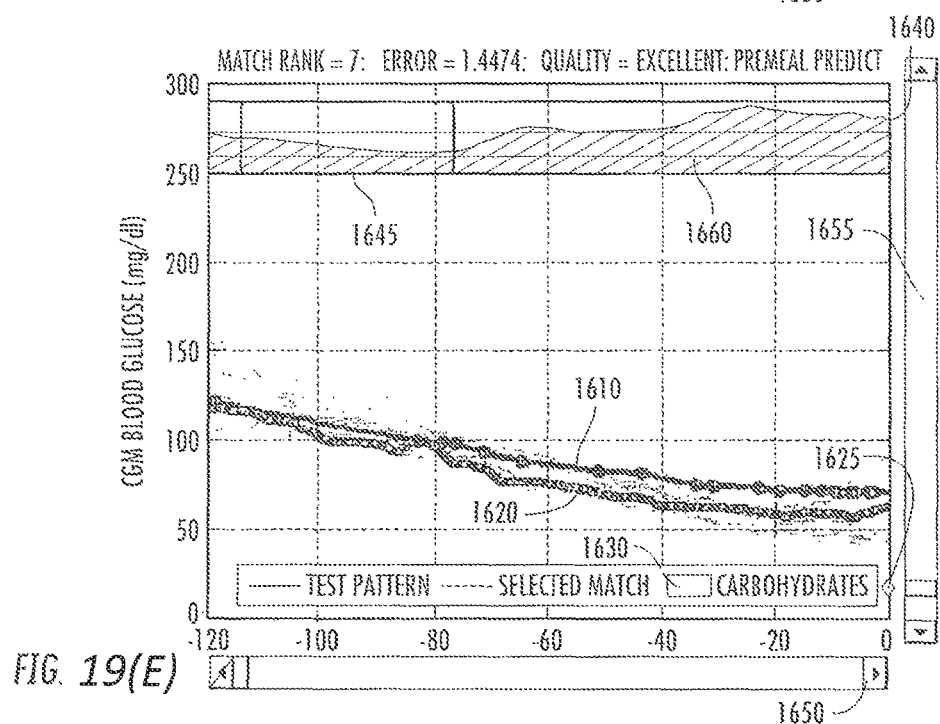

FIGS. 19(d) and 19(e) depict exemplary displays of a reference pattern plot of blood glucose concentration over time and includes matching using glucose levels, meal time tags, and carbohydrate values. Predictions of future glucose concentrations can be generated based on the matched data. The two figures depict a reference pattern 1610 with two different carbohydrate levels 1630 (shown only in FIG. 19(d)). The reference pattern 1610 and carbohydrate levels 1630 may be used to predict future blood glucose levels 1660, which are depicted in the timeline 1640. In this example, the reference pattern 1610 are selected for the two hour period prior to a meal. Reference pattern matches 1620 and carbohydrate matches 1625 were determined and plotted using the pattern matching algorithm. By way of example only, pattern matching may be done using a reference pattern 1610, glucose levels, meal time tags, and/or the current carbohydrate value 1630 that is being displayed. The displays shown include a timeline 1640 at the top of the reference pattern plot, which depicts the 2 hour matched section 1645 placed in a timeline with data shown on either side of matched section 1645 that may provide context of the match 1620. As mentioned above, timeline 1640 may also depict future blood glucose level predictions 1660. Also, shown is a horizontal scroll bar 1650 at the bottom of the screen that may be used to view the entire plot and/or scroll through matches. A vertical scroll bar 1655 may be used to scroll through and select or set the desired carbohydrate value 1630 to include in the reference pattern 1610. It may also be used to select a specific match 1620. The scroll bar 1655 may be a touch sensitive display, whereby the scroll bar on the screen is touched with a finger and then moving the finger in a desired direction on the screen. The arrows above and below scroll bar 1655 may be touched with a finger on the screen to scroll through and/or select a specific match. In addition, a mouse may also be used to scroll through using scroll bar 1655 or the up and down arrows. Quality of a match may be evaluated using error metrics (e.g., the absolute error between the match and the reference pattern), and a quality assessment label, for e.g., excellent, good, fair, poor, bad, awful, etc. or any other label that may be used to indicate the quality of a match.

Figure 20:
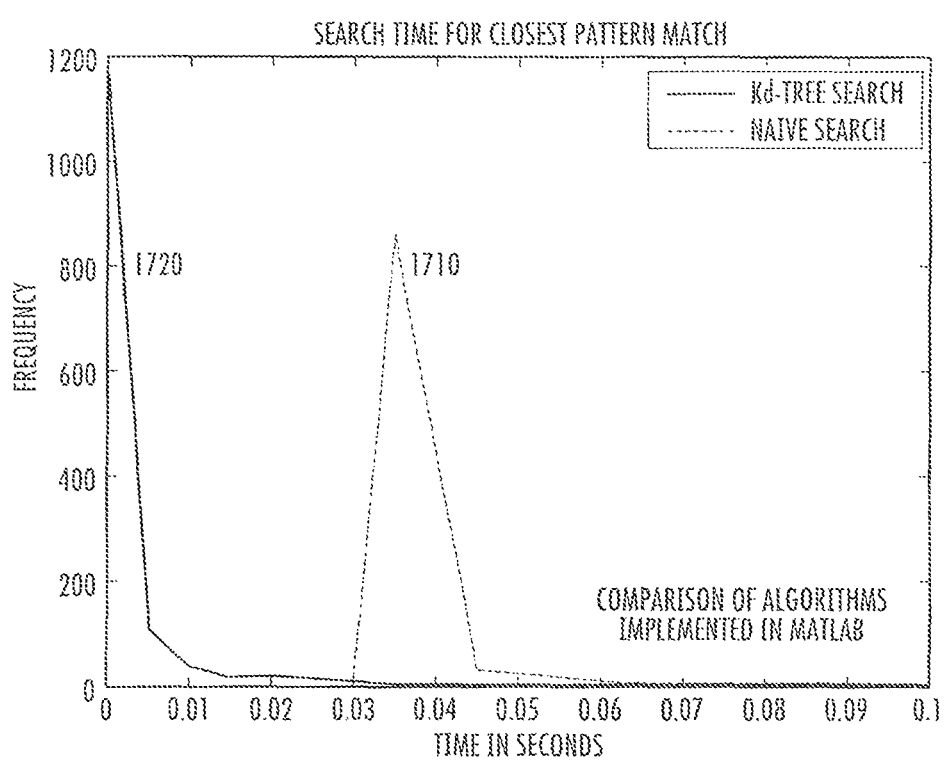
FIG. 20 depicts an exemplary plot of average search time in a pattern matching process.

FIG. 20 depicts an exemplary plot of the average search time for finding the closest match in the reduced-rank space when using two algorithms: a naïve exhaustive search 1710 and the Kd-tree search 1720. Both algorithms may be used for searches and may be relatively efficient due to the compression algorithm; however, in this example, the kd-tree search 1720 significantly reduced the search time from an average of about 0.038 seconds to less than about 0.005 seconds.

While several devices and components thereof have been discussed in detail above, it should be understood that the components, features, configurations, and methods of using the devices discussed are not limited to the contexts provided above. In particular, components, features, configurations, and methods of use described in the context of one of the devices may be incorporated into any of the other devices. Furthermore, not limited to the further description provided below, additional and alternative suitable components, features, configurations, and methods of using the devices, as well as various ways in which the teachings herein may be combined and interchanged, will be apparent to those of ordinary skill in the art in view of the teachings herein.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and understood not to be limited to the details of structure and operation shown and described in the specification and drawings.

In the following, particular embodiments of the invention denoted as embodiment (1)-(42) are given. Any features, functions or properties described herein in the context of the invention can be combined with the embodiments (1)-(42) as given in the following:

Embodiments (1)-(42)

Embodiment (1)

A patient monitoring system for a patient comprising:
a physiological data input device which acquires a plurality of physiological measurements of the patient within a time window thereby generating at least one time window data set;
a memory storing a pattern matching algorithm; and
a processor in communication with said input device to receive said generated at least one time window data set, and in communication with said memory in order to execute said pattern matching algorithm, wherein said pattern matching algorithm when executed by said processor causes said processor to compress the at least one time window data set, store the compressed at least one time window data set, and perform a pattern match between a reference pattern and the stored at least one time window data set using a distance metric provided by the pattern matching algorithm.

Embodiment (2)

The system of embodiment (1), wherein the physiological data input device is a sensor which acquires a plurality of glucose measurements within the time window.

Embodiment (3)

The system of embodiment (1), wherein the reference pattern is another at least one time window data set, at least one transformed time window data set, at least one generated data set, at least one generated glucose curve, one or more data tags, one or more generated data tag values, at least one multi-analyte data set, or at least one generated multi-analyte data set or combinations thereof.

Embodiment (4)

The system of embodiment (1), wherein said processor is caused to compress the at least one time window data set into a reduced-rank space using a transformation matrix.

Embodiment (5)

The system of embodiment (4), wherein the transformation matrix is determined by an initialization algorithm, which when executed by the processor, causes the processor to perform an Eigen-decomposition on a large, representative physiological measurements dataset to determine $\lambda$ eigenvalues and V eigenvectors, calculate the cumulative sum of the eigenvalues, and select a subset K of the largest Eigen vectors.

Embodiment (6)

The system of embodiment (5), wherein K is six or less.

Embodiment (7)

The system of embodiment (5), wherein K is preselected to retain at least about 90% of the original data from the at least one time window data set.

Embodiment (8)

The system of embodiment (1), wherein said memory further stores a data pre-processing algorithm, wherein the data pre-processing program, when executed by said processor, causes said processor to normalize and center the at least one time window data set to a scale where the distribution of the plurality of physiological measurements have a mean of zero and a standard deviation of one.

Embodiment (9)

The system of embodiment (1), wherein the distance metric is selected from Euclidean distance, Mahalanobis distance, and a modified Euclidean distance.

Embodiment (10)

The system of embodiment (1), wherein the processor pattern matches by determining the closest match that minimizes the distance metric within the reduced-rank space.

Embodiment (11)

The system of embodiment (1), wherein the processor pattern matches by finding the nearest d neighbors that minimize the distance metric within the reduced-rank space, where d is the number of neighbors of interest.

Embodiment (12)

The system of embodiment (9), wherein the modified Euclidean distance is modified with an error penalty function that determines the absolute error of a pattern match.

Embodiment (13)

The system of embodiment (1), wherein the database comprises one or more storage algorithms, which when executed by said processor, cause the processor to store a compressed dataset in a Kd-tree structure in the database.

Embodiment (14)

The system of embodiment (13), wherein the one or more storage algorithms, when executed by said processor, cause the processor to add the compressed dataset to a queue, and then add the compressed dataset from the queue to the Kd-tree structure.

Embodiment (15)

The system of embodiment (1), wherein the processor performs the pattern match using a Kd-tree search.

Embodiment (16)

The system of embodiment (1), wherein the processor performs the pattern match using a naïve exhaustive search.

Embodiment (17)

A non-transitory computer-readable medium that stores a program that, when executed by a processor, causes the processor to perform at least a pattern match using a distance metric between a reference pattern and at least one stored time window data set collected via a patient monitoring system.

Embodiment (18)

The non-transitory computer-readable medium of embodiment (17), wherein the reference pattern is at least one time window data set from a patient, at least one time window data set from more than one patient, at least one transformed time window data set, at least one generated data set, at least one generated glucose curve, one or more data tags, or at least one multi-analyte data set, or combinations thereof.

Embodiment (19)

The non-transitory computer-readable medium of embodiment (17), wherein the at least one time window data set is raw data, transformed data, raw data associated with related data tags, transformed data associated with related data tags, or combinations thereof.

Embodiment (20)

The non-transitory computer-readable medium of embodiment (17), wherein the program causes the processor to perform the pattern match by finding the nearest neighbor to the reference pattern.

Embodiment (21)

The non-transitory computer-readable medium of embodiment (17), wherein the program causes the processor to perform the pattern match by finding the nearest d neighbors, where d is the number of neighbors of interest.

Embodiment (22)

The non-transitory computer-readable medium of embodiment (17), wherein the program causes the processor to perform the pattern match by finding at least one data point within some range r of the reference pattern, where r is the desired distance from the reference pattern.

Embodiment (23)

The non-transitory computer-readable medium of embodiment (17), wherein the distance metric is selected from Euclidean distance, Mahalanobis distance, and a modified Euclidean distance.

Embodiment (24)

The non-transitory computer-readable medium of embodiment (23), wherein the modified Euclidean distance is modified with an error penalty function that determines the absolute error of a pattern match.

Embodiment (25)

A method for identifying a diabetes-related event in a patient using a patient monitoring system comprising a physiological data input device and a processor, the method comprising:
receiving automatically from the physiological data input device at least one time window data set indicative of a physiological measurement related to the diabetes-related event;
associating automatically using the processor the at least one time window data set with a data tag;
transforming automatically using the processor the associated at least one time window data set into a normalized at least one time window data set, wherein the normalized at least one time window data set has a mean of zero and a standard deviation of one;
compressing automatically using the processor the normalized at least one time window data set into a compressed at least one time window data set;
storing automatically using the processor the compressed at least one time window data set; and
pattern matching automatically using the processor between a reference pattern and the stored at least one time window data set using a distance metric.

Embodiment (26)

The method of embodiment (25), further comprises automatically using the processor to store the compressed at least one time window data set in a Kd-tree.

Embodiment (27)

The method of embodiment (25), wherein pattern matching comprises, finding automatically using the processor, a closest match by calculating the distance metric between the reference pattern and the closest match within the reduced-rank space, wherein the closest match is one of the stored at least one time window data set that minimizes the distance metric.

Embodiment (28)

The method of embodiment (25), wherein the distance metric is selected from Euclidean distance, Mahalanobis distance, and a modified Euclidean distance.

Embodiment (29)

The method of embodiment (28), wherein the modified Euclidean distance is modified with an error penalty function that determines the absolute error of a pattern match.

Embodiment (30)

The method of embodiment (27), wherein finding the closest match is performed using a Kd-tree search.

Embodiment (31)

The method of embodiment (27), wherein finding the closest match is performed using a naïve exhaustive search.

Embodiment (32)

The method of embodiment (25), wherein the compressed at least one time window data set is compressed automatically by the processor into a reduced-rank space by performing an eigen-decomposition via decomposing an $\hat{X}^T\hat{X}$ matrix into $\lambda$ eigenvalues and V eigenvectors.

Embodiment (33)

The method of embodiment (32) further comprising automatically calculating using the processor the cumulative sum of the eigenvalues, determining the corresponding eigenvector for each eigenvector, and selecting a subset of eigenvectors by balancing between data compression and preservation of relevant information.

Embodiment (34)

The method of embodiment (33) further comprising automatically applying using the processor an orthogonal transform matrix to said subset of eigenvectors to provide a compressed reduced-rank vector.

Embodiment (35)

A method for real-time identification of a diabetes-related event in a patient using a monitoring system comprising a physiological data input device, a user input device and a processor, the method comprising:
receiving automatically from the user input device at least one reference pattern and associated alert signal;
receiving automatically from the physiological data input device at least one time window data set indicative of a physiological measurement related to the diabetes-related event;
associating automatically using the processor the at least one time window data set with a data tag;
transforming automatically using the processor the associated at least one time window data set into a normalized at least one time window data set, wherein the normalized at least one time window data set has a mean of zero and a standard deviation of one;

compressing automatically using the processor the normalized at least one time window data set into a compressed at least one time window data set;

storing automatically using the processor the compressed at least one time window data set; and pattern matching automatically using the processor between the reference pattern and the stored at least one time window data set using a distance metric, wherein when the distance metric is less than ε, the processor automatically triggers the alert.

Embodiment (36)

The method of embodiment (35), further comprising:

transforming automatically using the processor the reference pattern into a normalized reference pattern, wherein the normalized reference pattern has a mean of zero and a standard deviation of one, and compressing automatically using the processor the normalized reference pattern into a compressed reference pattern.

Embodiment (37)

The method of embodiment (35), wherein ε is selected so that the probability that the matches are measurements of the same physiological data is at least about 0.95.

Embodiment (38)

The method of embodiment (35), wherein ε is selected so that the probability that the matches are measurements of the same physiological data is at least about 0.98.

Embodiment (39)

The method of embodiment (35), wherein the distance metric is selected from Euclidean distance, Mahalanobis distance, and a modified Euclidean distance.

Embodiment (40)

The method of embodiment (35), wherein the compressed at least one time window data set is compressed automatically by the processor into a reduced-rank space by performing an eigen-decomposition via decomposing an $\hat{X}^T\hat{X}$ matrix into λ eigenvalues and V eigenvectors.

Embodiment (41)

The method of embodiment (40) further comprising automatically calculating using the processor the cumulative sum of the eigenvalues, determining the corresponding eigenvector for each eigenvector, and selecting a subset of eigenvectors by balancing between data compression and preservation of relevant information.

Embodiment (42)

The method of embodiment (41) further comprising automatically applying using the processor an orthogonal transform matrix to said subset of eigenvectors to provide a compressed reduced-rank vector.

Finally, particular realizations of the invention could be defined as follows: A patient monitoring system with an efficient pattern matching algorithm, a method, and a computer product thereof, in particular as disclosed herein. The system may include a physiological data input device or sensor which receives a plurality of physiological measurements within a time window thereby generating at least one time window data set, a memory which stores a program, and a processor. The program when executed by the processor, causes the processor to compress the at least one time window data set to a reduced-rank basis, and perform a pattern match between a reference pattern and the compressed at least one time window data set using a distance metric.

The invention claimed is:

1. A method for managing glucose levels of a user, comprising:
    a) acquiring glucose concentration values from a glucose sensor at different measurement times and storing the glucose concentration values in a measurement data record;
    b) using data reduction to generate a reduced measurement data record from the measurement data record, wherein the reduced measurement data record is used in at least one of step c) and step d);
    c) selecting a current pattern from the glucose concentration values for a current time interval;
    d) using pattern recognition to identify a historical pattern of the glucose concentration values that is similar to the current pattern;
    e) generating a current profile of glucose concentration from the current pattern and generating a predicted future profile of glucose concentration from the historical pattern;
    f) displaying the current profile and the predicted future profile on a display;
    g) displaying a treatment instruction based upon the predicted future profile; and
    h) the user administering the treatment.

2. The method of claim 1, wherein the treatment instruction is one of: dosing insulin, engaging in physical activity, consuming carbohydrates and seeking medical attention.

3. The method of claim 1, wherein the treatment instruction is dosing insulin.

4. The method of claim 1, further comprising prompting the patient to enter a confirmation into a processor that the treatment instruction has been completed.

5. The method of claim 1, wherein the data reduction used in step b) comprises indexing.

6. The method of claim 5, wherein the indexing comprises checking whether a threshold is crossed between two adjacent measurement values.

7. The method of claim 6, further comprising assigning the adjacent measurement value that is closer to the threshold to the reduced measurement data record.

8. The method according to claim 1, wherein a correspondence between the current pattern and the historical pattern is calculated.

9. The method according to claim 8, wherein the correspondence is a function of differences between individual measurement values in the current pattern and respective measurement values from the historical pattern.

10. The method according to claim 1, wherein one or more boundary conditions are stored in the measurement data record and/or the reduced measurement data record.

11. The method according to claim 1, wherein step d) comprises identifying a group of historical patterns.

12. The method according to claim 11, wherein the group of historical patterns is subjected to an analysis.

13. The method according to claim 12, wherein the analysis is a statistical analysis.

14. The method according to claim 13, wherein the statistical analysis is performed using an averaged pattern and/or an error corridor.

15. A method for managing glucose levels of a user, comprising:
- a) acquiring glucose concentration values from a glucose sensor at different measurement times and storing the glucose concentration values in a measurement data record;
- b) using data reduction to generate a reduced measurement data record from the measurement data record, wherein the reduced measurement data record is used in at least one of step c) and step d);
- c) selecting a current pattern from the glucose concentration values for a current time interval;
- d) using pattern recognition to identify a historical pattern of the glucose concentration values that is similar to the current pattern;
- e) generating a current profile of glucose concentration from the current pattern and generating a predicted future profile of glucose concentration from the historical pattern;
- f) displaying the current profile and the predicted future profile on a display;
- g) displaying an instruction to administer an insulin dose based upon the predicted future profile; and
- h) administering the insulin dose.

16. The method of claim 15, wherein the data reduction used in step b) comprises indexing.

17. The method of claim 16, wherein the indexing comprises checking whether a threshold is crossed between two adjacent measurement values.

18. The method of claim 17, further comprising assigning the adjacent measurement value that is closer to the threshold to the reduced measurement data record.

* * * * *

UNITED STATES PATENT AND TRADEMARK OFFICE
CERTIFICATE OF CORRECTION

| | |
|---|---|
| PATENT NO. | : 10,575,791 B2 |
| APPLICATION NO. | : 13/923357 |
| DATED | : March 3, 2020 |
| INVENTOR(S) | : David Duke et al. |

It is certified that error appears in the above-identified patent and that said Letters Patent is hereby corrected as shown below:

On the Title Page

The Related U.S. Application Data at (63) and continued on page 2 at item (60) should read:
-- Continuation of application No. PCT/EP2011/073084, filed on Dec. 16, 2011, which is a continuation of application No. 12/975,654, filed on Dec. 22, 2010, now Pat. No. 8,774,889. --

Signed and Sealed this
Nineteenth Day of May, 2020

Andrei Iancu
*Director of the United States Patent and Trademark Office*